(12) United States Patent
Schecter

(10) Patent No.: US 10,013,082 B2
(45) Date of Patent: Jul. 3, 2018

(54) OPERATING SYSTEM WITH HAPTIC INTERFACE FOR MINIMALLY INVASIVE, HAND-HELD SURGICAL INSTRUMENT

(71) Applicant: Stuart O. Schecter, Great Neck, NY (US)

(72) Inventor: Stuart O. Schecter, Great Neck, NY (US)

(73) Assignee: Stuart Schecter, LLC, Great Neck, NY (US)

( * ) Notice: Subject to any disclaimer, the term of this patent is extended or adjusted under 35 U.S.C. 154(b) by 1067 days.

(21) Appl. No.: 13/837,132

(22) Filed: Mar. 15, 2013

(65) Prior Publication Data

US 2013/0321262 A1 Dec. 5, 2013

Related U.S. Application Data

(60) Provisional application No. 61/655,804, filed on Jun. 5, 2012.

(51) Int. Cl.
*G06F 3/041* (2006.01)
*G06F 3/01* (2006.01)
(Continued)

(52) U.S. Cl.
CPC ............ *G06F 3/041* (2013.01); *A61B 5/7455* (2013.01); *A61B 34/76* (2016.02); *G06F 3/016* (2013.01);
(Continued)

(58) Field of Classification Search
CPC ........... A61B 17/00; A61B 34/76; A61B 5/00; A61B 5/05; A61B 5/11; G09G 5/00; G09G 5/08; A61M 25/00; A61M 25/01
See application file for complete search history.

(56) References Cited

U.S. PATENT DOCUMENTS

| 3,184,842 A | 5/1965 | Nicholas |
| 4,019,073 A | 4/1977 | Vishnevsky et al. |

(Continued)

FOREIGN PATENT DOCUMENTS

| EP | 0970663 A1 | 1/2000 |
| KR | 20110004401 A | 1/2011 |

(Continued)

OTHER PUBLICATIONS

U.S. Appl. No. 61/628,551, filed Nov. 2, 2011.
(Continued)

*Primary Examiner* — Ilana Spar
*Assistant Examiner* — Nguyen H Truong
(74) *Attorney, Agent, or Firm* — Patterson Thuente Pedersen, P.A.

(57) ABSTRACT

A haptic system for a minimally invasive, hand-held surgical instrument and the system's various parts including a graphical user haptic interface, one or more haptic interfaces associated with a hand-held handle used to control a sensorized end-effector of the surgical instrument or inserted catheters, associated hardware, and an operating system. The system enables users to acquire, read, modify, store, write, and download sensor-acquired data in real time. The system can provide: an open, universally compatible platform capable of sensing or acquiring physiological signals/data in any format; processing of the sensor acquired data within an operating system; and outputting the processed signals to hardware which generates tangible sensations via one or more haptic interfaces. These tangible sensations can be modified by the user in real time as the system ensures the temporal relationship of sensed fiducial events are not altered or shifted relative to the generated and displayed haptic signals.

20 Claims, 27 Drawing Sheets

(51) Int. Cl.
*A61B 5/00* (2006.01)
*A61B 34/00* (2016.01)
*A61B 17/00* (2006.01)
*A61B 18/00* (2006.01)
*A61B 18/14* (2006.01)
*A61B 34/20* (2016.01)
*A61B 90/00* (2016.01)
*A61B 34/30* (2016.01)

(52) U.S. Cl.
CPC ........... *A61B 18/1492* (2013.01); *A61B 34/20* (2016.02); *A61B 2017/00871* (2013.01); *A61B 2018/00297* (2013.01); *A61B 2018/00357* (2013.01); *A61B 2018/00577* (2013.01); *A61B 2034/301* (2016.02); *A61B 2090/064* (2016.02)

(56) References Cited

U.S. PATENT DOCUMENTS

| | | |
|---|---|---|
| 4,210,837 A | 7/1980 | Vasiliev et al. |
| 4,432,372 A | 2/1984 | Monroe |
| 4,844,062 A | 7/1989 | Wells |
| 5,389,865 A | 2/1995 | Jacobus et al. |
| 5,429,604 A | 7/1995 | Hammersmark et al. |
| 5,484,433 A | 1/1996 | Taylor et al. |
| 5,549,650 A | 8/1996 | Bornzin et al. |
| 5,576,727 A | 11/1996 | Rosenberg et al. |
| 5,609,607 A | 3/1997 | Hechtenberg et al. |
| 5,628,777 A | 5/1997 | Moberg et al. |
| 5,693,074 A | 12/1997 | Ferek Petric |
| 5,702,438 A | 12/1997 | Avitall |
| 5,769,640 A | 6/1998 | Jacobus et al. |
| 5,771,902 A | 6/1998 | Lee et al. |
| 5,833,623 A | 11/1998 | Mann et al. |
| 5,836,946 A | 11/1998 | Diaz et al. |
| 5,843,135 A | 12/1998 | Weijand et al. |
| 5,844,392 A | 12/1998 | Peurach et al. |
| 5,916,143 A | 6/1999 | Apple et al. |
| 5,944,022 A | 8/1999 | Nardella et al. |
| 5,959,613 A | 9/1999 | Rosenberg et al. |
| 5,971,931 A | 10/1999 | Raff |
| 6,059,759 A | 5/2000 | Mottola et al. |
| 6,070,100 A | 5/2000 | Bakels et al. |
| 6,077,236 A | 6/2000 | Cunningham |
| 6,096,004 A | 8/2000 | Meglan et al. |
| 6,104,158 A | 8/2000 | Jacobus et al. |
| 6,147,674 A | 11/2000 | Rosenberg et al. |
| 6,203,432 B1 | 3/2001 | Roberts et al. |
| 6,278,439 B1 | 8/2001 | Rosenberg et al. |
| 6,300,936 B1 | 10/2001 | Braun et al. |
| 6,304,777 B1 | 10/2001 | Ben Haim et al. |
| 6,418,346 B1 | 7/2002 | Nelson et al. |
| 6,424,356 B2 | 7/2002 | Chang et al. |
| 6,429,849 B1 | 8/2002 | An et al. |
| 6,442,433 B1 | 8/2002 | Linberg |
| 6,480,745 B2 | 11/2002 | Nelson et al. |
| 6,526,984 B1 | 3/2003 | Nilsson et al. |
| 6,527,683 B2 | 3/2003 | Tolles |
| 6,572,560 B1 | 6/2003 | Watrous et al. |
| 6,574,511 B2 | 6/2003 | Lee |
| 6,622,045 B2 | 9/2003 | Snell et al. |
| 6,628,988 B2 | 9/2003 | Kramer et al. |
| 6,641,480 B2 | 11/2003 | Murzanski et al. |
| 6,685,732 B2 | 2/2004 | Kramer |
| 6,725,091 B2 | 4/2004 | Dal Molin |
| 6,740,033 B1 | 5/2004 | Olejniczak et al. |
| 6,746,972 B1 | 6/2004 | Kim et al. |
| 6,780,183 B2 | 8/2004 | Jimenez, Jr. et al. |
| 6,792,308 B2 | 9/2004 | Corbucci |
| 6,795,732 B2 | 9/2004 | Stadler et al. |
| 6,801,008 B1 | 10/2004 | Jacobus et al. |
| 6,804,559 B1 | 10/2004 | Kraus et al. |
| 6,805,667 B2 | 10/2004 | Christopherson et al. |
| 6,810,281 B2 | 10/2004 | Brock et al. |
| 6,816,301 B1 | 11/2004 | Schiller |
| 6,826,509 B2 | 11/2004 | Crisco, III et al. |
| 6,837,886 B2 | 1/2005 | Collins et al. |
| 6,863,943 B2 | 3/2005 | Wang et al. |
| 6,906,700 B1 | 6/2005 | Armstrong |
| 7,010,347 B2 | 3/2006 | Schecter |
| 7,063,671 B2 | 6/2006 | Couvillon, Jr. |
| 7,065,400 B2 | 6/2006 | Schechter |
| 7,091,948 B2 | 8/2006 | Chang et al. |
| 7,101,347 B2 | 9/2006 | Culhane et al. |
| 7,127,289 B2 | 10/2006 | Yu et al. |
| 7,139,621 B2 | 11/2006 | Gharsalli |
| 7,147,633 B2 | 12/2006 | Chee et al. |
| 7,154,470 B2 | 12/2006 | Tierling |
| 7,168,042 B2 | 1/2007 | Braun et al. |
| 7,176,892 B2 | 2/2007 | Kobayashi |
| 7,183,568 B2 | 2/2007 | Appenzeller et al. |
| 7,191,191 B2 | 3/2007 | Peurach et al. |
| 7,199,790 B2 | 4/2007 | Rosenberg et al. |
| 7,206,633 B2 | 4/2007 | Saba |
| 7,209,117 B2 | 4/2007 | Rosenberg et al. |
| 7,218,310 B2 | 5/2007 | Tierling et al. |
| 7,225,404 B1 | 5/2007 | Zilles et al. |
| 7,257,447 B2 | 8/2007 | Cates et al. |
| 7,266,832 B2 | 9/2007 | Miller |
| 7,316,681 B2 | 1/2008 | Madhani et al. |
| 7,331,967 B2 | 2/2008 | Lee et al. |
| 7,333,643 B2 | 2/2008 | Murphy et al. |
| 7,369,115 B2 | 5/2008 | Cruz-Hernandez et al. |
| 7,386,365 B2 | 6/2008 | Nixon |
| 7,426,412 B1 | 9/2008 | Schecter |
| 7,623,114 B2 | 11/2009 | Rank |
| 7,639,232 B2 | 12/2009 | Grant et al. |
| 7,653,436 B2 | 1/2010 | Schecter |
| 7,656,388 B2 | 2/2010 | Schena et al. |
| 7,689,283 B1 | 3/2010 | Schecter |
| 7,701,438 B2 | 4/2010 | Chang et al. |
| 7,720,529 B1 | 5/2010 | Schecter |
| 7,725,214 B2 | 5/2010 | Diolaiti |
| 7,740,627 B2 | 6/2010 | Gammie et al. |
| 7,751,888 B1 | 7/2010 | Schecter |
| 7,751,889 B1 | 7/2010 | Schecter |
| 7,762,985 B2 | 7/2010 | Kabrick et al. |
| 7,765,333 B2 | 7/2010 | Cruz-Hernandez et al. |
| 7,770,262 B2 | 8/2010 | Schultz et al. |
| 7,779,166 B2 | 8/2010 | Grant et al. |
| 7,780,651 B2 | 8/2010 | Madhani et al. |
| 7,791,588 B2 | 9/2010 | Tierling et al. |
| 7,794,455 B2 | 9/2010 | Abboud et al. |
| 7,805,194 B1 | 9/2010 | Schecter |
| 7,821,493 B2 | 10/2010 | Tierling et al. |
| 7,821,498 B2 | 10/2010 | Kramer et al. |
| 7,843,158 B2 | 11/2010 | Prisco |
| 7,850,642 B2 | 12/2010 | Moll et al. |
| 7,865,269 B2 | 1/2011 | Prisco et al. |
| 7,898,156 B2 | 3/2011 | Wang et al. |
| 7,924,144 B2 | 4/2011 | Makinen et al. |
| 7,931,586 B2 | 4/2011 | Brock et al. |
| 7,942,868 B2 | 5/2011 | Cooper |
| 7,947,050 B2 | 5/2011 | Lee et al. |
| 7,947,051 B2 | 5/2011 | Lee et al. |
| 7,963,288 B2 | 6/2011 | Rosenberg et al. |
| 7,963,925 B1 | 6/2011 | Schecter |
| 7,969,288 B2 | 6/2011 | Braun et al. |
| 7,970,469 B2 | 6/2011 | Schecter |
| 7,972,298 B2 | 7/2011 | Wallace et al. |
| 7,974,681 B2 | 7/2011 | Wallace et al. |
| 7,978,183 B2 | 7/2011 | Rosenberg et al. |
| 7,979,146 B2 | 7/2011 | Ullrich et al. |
| 7,982,588 B2 | 7/2011 | Makinen et al. |
| 7,982,720 B2 | 7/2011 | Rosenberg et al. |
| 8,000,825 B2 | 8/2011 | Ullrich et al. |
| 8,003,982 B2 | 8/2011 | Wang et al. |
| 8,004,229 B2 | 8/2011 | Nowlin et al. |
| 8,010,180 B2 | 8/2011 | Quaid et al. |
| 8,014,864 B2 | 9/2011 | Schecter |
| 8,016,818 B2 | 9/2011 | Ellis et al. |
| 8,026,798 B2 | 9/2011 | Makinen et al. |
| 8,032,212 B2 | 10/2011 | Bornzin et al. |
| 8,039,834 B2 | 10/2011 | Wang et al. |

(56) References Cited

U.S. PATENT DOCUMENTS

| | | | |
|---|---|---|---|
| 8,041,413 B2 | 10/2011 | Barbagli et al. | |
| 8,043,351 B2 | 10/2011 | Yon et al. | |
| 8,050,760 B2 | 11/2011 | Cholette | |
| 8,059,105 B2 | 11/2011 | Rosenberg et al. | |
| 8,090,444 B2 | 1/2012 | Min et al. | |
| 8,156,809 B2 | 4/2012 | Tierling et al. | |
| 8,174,373 B2 | 5/2012 | Makinen et al. | |
| 8,209,012 B2 | 6/2012 | Schecter | |
| 8,211,032 B2 | 7/2012 | Schecter et al. | |
| 8,214,039 B1 | 7/2012 | Schecter | |
| 8,292,797 B2 | 10/2012 | Chapman et al. | |
| 8,663,122 B2 | 3/2014 | Schecter | |
| 2002/0015950 A1 | 2/2002 | Jones et al. | |
| 2002/0026103 A1 | 2/2002 | Norris et al. | |
| 2002/0072784 A1 | 6/2002 | Sheppard et al. | |
| 2002/0120188 A1* | 8/2002 | Brock | A61B 90/36 600/407 |
| 2002/0163498 A1* | 11/2002 | Chang | G06F 3/016 345/156 |
| 2002/0183738 A1 | 12/2002 | Chee et al. | |
| 2003/0006669 A1 | 1/2003 | Pei et al. | |
| 2003/0083702 A1 | 5/2003 | Stadler et al. | |
| 2003/0187362 A1 | 10/2003 | Murphy et al. | |
| 2003/0216620 A1 | 11/2003 | Jain et al. | |
| 2004/0019285 A1 | 1/2004 | Eigler et al. | |
| 2004/0068199 A1 | 4/2004 | Echauz et al. | |
| 2004/0111127 A1 | 6/2004 | Gliner | |
| 2004/0153128 A1 | 8/2004 | Suresh et al. | |
| 2004/0167587 A1 | 8/2004 | Thompson | |
| 2004/0172079 A1 | 9/2004 | Chinchoy | |
| 2004/0176679 A1 | 9/2004 | Murphy et al. | |
| 2004/0176810 A1 | 9/2004 | Stadler et al. | |
| 2004/0186465 A1 | 9/2004 | Francischelli et al. | |
| 2004/0231100 A1 | 11/2004 | Schultz et al. | |
| 2005/0043895 A1 | 2/2005 | Schechter | |
| 2005/0059876 A1 | 3/2005 | Krishnan et al. | |
| 2005/0113886 A1 | 5/2005 | Fischell et al. | |
| 2005/0182447 A1 | 8/2005 | Schecter | |
| 2005/0234339 A1* | 10/2005 | Phillips | A61B 8/462 600/453 |
| 2005/0241026 A1 | 10/2005 | Esler et al. | |
| 2005/0262676 A1 | 12/2005 | Kim et al. | |
| 2005/0280508 A1 | 12/2005 | Mravca et al. | |
| 2006/0059997 A1 | 3/2006 | Kim et al. | |
| 2006/0083720 A1 | 4/2006 | Fraser et al. | |
| 2006/0114088 A1 | 6/2006 | Shachar | |
| 2006/0129719 A1* | 6/2006 | Cruz-Hernandez | G06F 3/0488 710/58 |
| 2006/0142657 A1* | 6/2006 | Quaid | A61N 1/372 600/424 |
| 2006/0159747 A1 | 7/2006 | Schumacher et al. | |
| 2006/0161045 A1 | 7/2006 | Merril et al. | |
| 2006/0167529 A1 | 7/2006 | Schecter | |
| 2006/0276775 A1 | 12/2006 | Rosenberg et al. | |
| 2007/0021977 A1 | 1/2007 | Elsholz | |
| 2007/0043338 A1 | 2/2007 | Moll et al. | |
| 2007/0103437 A1 | 5/2007 | Rosenberg | |
| 2007/0156123 A1 | 7/2007 | Moll et al. | |
| 2007/0173861 A1 | 7/2007 | Strommer et al. | |
| 2007/0191901 A1 | 8/2007 | Schecter | |
| 2007/0197896 A1 | 8/2007 | Moll et al. | |
| 2007/0197939 A1 | 8/2007 | Wallace et al. | |
| 2007/0233044 A1 | 10/2007 | Wallace et al. | |
| 2008/0009750 A1 | 1/2008 | Aeby et al. | |
| 2008/0009759 A1 | 1/2008 | Chetham | |
| 2008/0009791 A1 | 1/2008 | Cohen et al. | |
| 2008/0010705 A1 | 1/2008 | Quaid et al. | |
| 2008/0067618 A1 | 3/2008 | Wang et al. | |
| 2008/0119871 A1 | 5/2008 | Brock et al. | |
| 2008/0218770 A1 | 9/2008 | Moll et al. | |
| 2008/0262513 A1 | 10/2008 | Stahler et al. | |
| 2008/0275367 A1 | 11/2008 | Barbagli et al. | |
| 2008/0288013 A1 | 11/2008 | Schecter | |
| 2008/0290040 A1 | 11/2008 | Kane et al. | |
| 2008/0294984 A1* | 11/2008 | Ramsay | G06F 1/1626 715/702 |
| 2008/0303782 A1 | 12/2008 | Grant et al. | |
| 2009/0012533 A1 | 1/2009 | Barbagli et al. | |
| 2009/0024141 A1 | 1/2009 | Stahler et al. | |
| 2009/0030332 A1* | 1/2009 | Schecter | A61B 5/0031 600/508 |
| 2009/0062602 A1 | 3/2009 | Rosenberg et al. | |
| 2009/0066195 A1 | 3/2009 | Wang et al. | |
| 2009/0076476 A1 | 3/2009 | Barbagli et al. | |
| 2009/0123111 A1 | 5/2009 | Udd | |
| 2009/0138025 A1 | 5/2009 | Stahler et al. | |
| 2009/0167677 A1 | 7/2009 | Kruse et al. | |
| 2009/0177095 A1 | 7/2009 | Aeby et al. | |
| 2009/0179523 A1 | 7/2009 | Wang et al. | |
| 2009/0243997 A1 | 10/2009 | Tierling et al. | |
| 2009/0259280 A1 | 10/2009 | Wilkin et al. | |
| 2009/0299431 A1 | 12/2009 | Schecter | |
| 2009/0301196 A1 | 12/2009 | Wang et al. | |
| 2009/0312814 A1 | 12/2009 | Schecter et al. | |
| 2010/0013761 A1 | 1/2010 | Birnbaum et al. | |
| 2010/0017759 A1 | 1/2010 | Birnbaum et al. | |
| 2010/0045619 A1 | 2/2010 | Birnbaum et al. | |
| 2010/0049060 A1 | 2/2010 | Schecter | |
| 2010/0056851 A1 | 3/2010 | Wang et al. | |
| 2010/0063478 A1 | 3/2010 | Selkee | |
| 2010/0073150 A1 | 3/2010 | Olson et al. | |
| 2010/0114115 A1 | 5/2010 | Schlesinger et al. | |
| 2010/0117488 A1 | 5/2010 | Wang et al. | |
| 2010/0121403 A1 | 5/2010 | Schecter et al. | |
| 2010/0123588 A1 | 5/2010 | Cruz Hernandez et al. | |
| 2010/0152620 A1 | 6/2010 | Ramsay et al. | |
| 2010/0152795 A1 | 6/2010 | Schecter | |
| 2010/0152796 A1 | 6/2010 | Schecter | |
| 2010/0179587 A1 | 7/2010 | Grant et al. | |
| 2010/0228103 A1 | 9/2010 | Schecter | |
| 2010/0234913 A1 | 9/2010 | Schecter | |
| 2010/0283731 A1 | 11/2010 | Grant et al. | |
| 2010/0312129 A1 | 12/2010 | Schecter | |
| 2011/0006286 A1 | 1/2011 | Wang et al. | |
| 2011/0043454 A1 | 2/2011 | Modarres et al. | |
| 2011/0050405 A1 | 3/2011 | Hollis, Jr. et al. | |
| 2011/0090070 A1 | 4/2011 | Modarres et al. | |
| 2011/0121953 A1 | 5/2011 | Grant et al. | |
| 2011/0166513 A1 | 7/2011 | Cohen et al. | |
| 2011/0184406 A1 | 7/2011 | Selkee | |
| 2011/0193824 A1 | 8/2011 | Modarres et al. | |
| 2011/0230896 A1 | 9/2011 | Wallace et al. | |
| 2011/0238083 A1 | 9/2011 | Moll et al. | |
| 2011/0275947 A1 | 11/2011 | Feldman et al. | |
| 2011/0306890 A1 | 12/2011 | Schecter et al. | |
| 2012/0179070 A1* | 7/2012 | Pommer | A61B 5/6843 600/594 |
| 2012/0265076 A1 | 10/2012 | Schecter | |
| 2012/0265083 A1 | 10/2012 | Schecter | |
| 2013/0274712 A1 | 10/2013 | Schecter | |
| 2014/0207010 A1 | 7/2014 | Schecter | |

FOREIGN PATENT DOCUMENTS

| | | |
|---|---|---|
| WO | WO2006081132 A2 | 8/2006 |
| WO | WO 2007/067941 A2 | 6/2007 |
| WO | WO2006081132 A3 | 11/2007 |
| WO | WO2010129892 A2 | 11/2010 |
| WO | WO2011005814 A1 | 1/2011 |
| WO | WO2011022319 A1 | 2/2011 |
| WO | WO2011046714 A1 | 4/2011 |
| WO | WO2011097356 A1 | 8/2011 |

OTHER PUBLICATIONS

U.S. Appl. No. 13/667,644, filed Nov. 2, 2012, Published as Patent Pub. No. 2013/0274712 A1 on Oct. 17, 2013.

U.S. Appl. No. 61/655,804, filed Jun. 5, 2012.

U.S. Appl. No. 14/105,749, filed Dec. 13, 2013, Published as Patent Pub. No. 2014/0207010 A1 on Jul. 24, 2014.

(56) References Cited

OTHER PUBLICATIONS

Makoto Shimojo et al., A High-Speed Mesh of Tactile Sensors Fitting Arbitrary Surfaces, IEEE Sensor Journal, vol. 10, No. 4, Apr. 2010.
Allison M. Okamura et al., Reality-Based Models for Vibration Feedback in Virtual Environments, IEEE/ ASME Transactions on Mechatronics, vol. 6, No. 3, Sep. 2001.
Office Action issued in related U.S. Appl. No. 11/746,752, dated Apr. 5, 2010.
Farrokh Janabi-Sharifi et al., Discrete-Time Adaptive Windowing for Velocity Estimation, IEEE/ASME Transactions on Control Systems Technology, vol. 8, No. 6, Nov. 2000.
Young Qin et al., Microfibre-nanowire Hybrid Structure for Energy Scavenging, School of Materials Science and Engineering, Georgia Institute of Technology, Atlanta, Georgia, USA, vol. 451, Feb. 2008.
S. Stramigioli et al., A Novel Theory for Sample Data System Passivity, IEEE/RSJ, International Conference of Intelligent Robots and Systems, EPFL, Lausanne, Switzerland, Oct. 2002.
Honjie Leng et al., Development of a Novel Deformation-Based Tissue Softness Sensor, IEEE Sensors Journal, vol. 9, No. 5, May 2009.
J. E. Colgate et al., Factors Affecting the Z-Width of a Haptic Display, IEEE, Department of Mechanical Engineering, Northwestern University, 2145 Sheridan Rd., Evanston, Illinois, 1994.
J. E. Colgate et al., Passivity of a Class of Sampled-Data Systems: Application to Haptic Interfaces, IEEE, Department of Mechanical Engineering, Northwestern University, Evanston, IL, Journal of Robotic Systems, John Wiley & Sons Inc, 1997.
Dipen C. Shah et al., Area Under the Real-Time Contact Force Curve (Force-Time Integral) Predicts Radiofrequency Lesion Size in an In Vitro Contractile Model, Journal of Cardiovascular Electrophysiology, vol. No. 10, pp. 1-5, 2010.
Office Action issued in the related U.S. Appl. No. 11/686,602 dated Jun. 24, 2010.
Excerpts, Heart Rhythm, vol. 2, No. 5, May Supplement, 2005 including Schecter S et al. The Effects of Atrial Flutter on Left Ventricular Rotation: A Tissue Doppler Study. Heart Rhythm Society 2005; 2(1S): S134.
Dissertation of Katherine Julianne Kuchenbecker, Characterizing and Controlling the High Frequency Dynamics of Haptic Devices. PhD Thesis Stanford University Department of Mechanical Engineering. 2006.
Giovanni B. Perego et al. "Simultaneous vs. sequesntial biventricular pacing in dilated cardiomyopathy . . . ", The European Journal of Heart Failure, 5, 2003, pp. 305-313.
Carlo Pappone et al."Cardiac Contractility Modulation by Electric Currents Applied During the Refractory Period in Patiens . . . ",The American Journal of Cardiology, V.90, Dec. 2002.
P. Ritter et ai."Determination of the optimal atrioventricular delay in DOD pacing, Comparison between echo and peak endocardial measurements", Europace, 1999, 1, pp. 126-130.
Jaroslav Meluzin et ai."A fast and simple echacardiographic method of determination of the optimal atrioventricular delay in patients after . . . " Pace, Jan. 2004,vol. 27.
Ric Willems et al. "Nonexcitatory stimulation as a novel treatment for heart failure: cause for excitement?" European Heart Journal, 2004, 25, pp. 626-628.
James D. Thomas et al. "Digital Echocardiography 2002: Now is the Time" Journal of the American Society of Echocardiography, Aug. 2002.
C-M Yu et al."High prevalence of left ventricular systolic and diastolic asynchrony in patients with confestive heart failure and normal QRS duration" Heart, 2003;89,pp. 54-60.
Carlo Pappone et al."First Human Chronic Experience With Cardiac Contractility Modulation by Nonexcitatory . . . " Journal of Cardiovascular Electrophysiology, vol. 15, 4, 2004.
Dipla, K. et ai."The Sarcoplasmic Reticulum and the Na+/Ca2+ Exchanger Both Contribute to theCa 2+ Transient of Failing Human Ventricular . . . ", Circulation Research, 1999;84.

Padeletti et al."Digital Technology for Cardiac Pacing" The American Journal of Cardiology, vol. 95, Feb. 15, 2005, pp. 479-482.
Harvey Feigenbaum "Digital Echocardiography", Excerpta Medica, Inc., 2000, 2G-3G.
Burknoff et al. "Electric Currents Applied During rhe Refractory Period Can Modulate Cardiac Cotnractility in Vitro and In Vivo", Heart Failure Previews, 6, 2001, pp. 27-34.
PCT Search Report from International Application No. PCT/US06/01946; search report completed Apr. 27, 2007 and dated Aug. 15, 2007.
Office Action issued in a corresponding U.S. Appl. No. 11/848,346, dated Dec. 22, 2010.
McMahan et al, Tool Contact Acceleration Feedback for Telerobotic Surgery, IEEE Transactions on Haptics, vol. 4, No. 3, p. 210-220, Jul.-Sep. 2011.
Zhong Y et. al. An electromechanical based deformable model for soft tissue simulation. Artificial Intelligence in Medicine. Nov. 2009; vol. 47, 3, pp. 275-288.
Controlling a Heart Simulator with CompactRIO and LabVIEW, http://sine.ni.com/cs/app/doc/p/id/cs-13021, as accessed on Feb. 13, 2013.
Chubb EC et al. ShiverPaD: A Glass Haptic Surface That Produces Shear Force on a Bare Finger. IEEE Transactions on Haptics 2010, vol. 3, No. 3, pp. 189-198.
Gleeson BT et al. Perception of Direction for Applied Tangential Skin Displacement: Effects of Speed, Displacement, and Repetition. IEEE Transactions on Haptics 2010, vol. 3, No. 3 pp. 177-188.
Mafi R, et. al. A parallel Computing Platform for Real-Time Haptic Interaction with Deformable Bodies. IEEE Transactions on Haptics 2010, vol. 3, No. 3. p. 211-223.
Frisoli A. et al. Kinematic Design of a Two Contact Points Haptic Interface for the Thumb and Index Fingers of the Hand. ASME J Mechanical Design, vol. 129, pp. 520-529, 2007.
Proctor RW et al. Implications of Compatibility and Cuing Effects for Multimodal Interfaces. Proc. Int'l Conf. Human-Computer Interaction, vol. 11, 2005.
Easton RD et. al. Transfer between Vision and Haptics: Memory for 2D Patterns and 3D Objects. Psychonomic Bull. and Rev., vol. 4, pp. 322-325, 1997.
Ahmaniemi T, et al. Design of Dynamic Vibrotactile Textures. IEEE Transactions on Haptics, vol. 3, No. 4. p. 245-256, Oct.-Dec. 2010.
Gleeson BT, et al. Design of a Fingertip-Mounted Tactile Display with Tangential Skin Displacement Feedback. IEEE Transactions on Haptics, vol. 3, No. 4. p. 297-298, Oct.-Dec. 2010.
Ikeda A. et al., Electrogram Prameters (Injury current, amplitude, dV/dt) and Impedance are poor predictors of electrode-tissue contact force for Radiofrequency Ablation. Heart Rhythm Society, May 2008, Abstract 4570, PO5-41.
Burdea, GC., Force and Touch Feedback for Virtual Reality. New York: Wiley Interscience, 1996, Abstract.
Nguyen, CTC, IEEE Spectrum Dec. 2009.
Hannaford B. et al. Stable Control of Haptics. In Touch in Virtual Environments: Proceedings USC Workshop on Haptic Interfaces, edited by Margret McLaughlin. Upper Saddle River, JN; Prentice Hall, 2001.
Abbott JJ, Okamura AM, Effects of Position Quantization and Sampling Rate on Virtual Wall Passivity, IEEE Transactions on Robotics 12:5 (2005), 952-964.
Salcudean SE, and Vlaar TD, On the Emulation of Stiff Walls and Static Friction with a Magneticaly Levitated Input/Output Device. 1996.
Immersion, Touchsense Tactile Feedback, http://www.immersion.com/products/touchsense-tactile-feedback/index.html, as accessed on Feb. 13, 2013.
DuraAct™ Piezoelectric Patch Transducers for Industry and Research, http://www.pi-usa.us/pdf/PI_Catalog_DuraAct_Piezo_Patch_Transducer_Piezo_Composite_C1.pdf, as accessed on Feb. 13, 2013.
Otaduy MA., Haptic Rendering; Foundations, Algorithms and Applications. A.K. Peters Ltd. 2008. p. 138-147, 440.
Extending the Hands of the Endoscopic Surgeon, http://actu.epfl.ch/news/extending-the-hands-of-the-endoscopic-surgeon/, Feb. 4, 2012.

(56) References Cited

OTHER PUBLICATIONS

Biosense completes patient enrollment in SMART—AF trial, Medical Device Network, Jan. 13, 2012.
Kawai M., and Yoshikawa T., Haptic Display of Movable Virtual Object with Interface Device Capable of Continuous-Time Impedance Display by Analog Circuit. In IEEE International Conference on Robotics and Automation, pp. 229-234, Washington, DC: IEEE Computer Society 2002.
Bracke, F., Neth Heart J 2008;16(Suppl1): S28-S31.
Coyne KS, Paramore C, Grandy S, Mercader M, Reynolds MR, Zimetbaum P. Assessing the direct costs of treating nonvalvular arterial fibrillation in the United States. *Value Health*, 2006;9:348-356. [PubMed].
Kozak LJ, Lees KA, DeFrances CJ. National Hospital Discharge Survey: 2003 Annual summary with detailed diagnosis and procedure data. *Vital Health Stat*. 2006:1-206.
Go AS, Hylek EM, Phillips KA, Chang Y, Henault LE, Selby JV, Singer DE. Prevalence of diagnosed atrial fibrillation in adults: National implications for rhythm management and stroke prevention. The anticoagulation and risk factors in atrial fibrillation (ATRIA) study. *JAMA* 2001;285:2370-2375.
Miyasaka Y, Barnes ME, Gersh BJ, Cha SS, Bailey KR, Abhayaratna WPS JB, Tsang TSM. Secular trends in incidence of atrial fibrilla-tion in Olmstead County, Minnesota, 1980 to 2000, and implications on the projections for future prevalence. *Circulation*, 2006;114:119-124.
Wattigney WA, Mensah GA, Croft JG. Increasing trends in hospitalization for atrial fibrillation in the United States, 1985 through 1999. *Circulation*. 2003;108:711-716.
Bentkover JD, Stewart EJ, Ignaszewski A, Lepage S, Liu P, Cooper J. *Int J. Cardiol*. Mar. 2003;88(1):33-41. New Technologies and potential cost savings related to morbidity and mortality reduction in Class II/IV heart failure patients in Canada.
Ho KK, Pinsky JL, Kannel WB, Levy D. *J Am Coll Cardiol*. Oct. 1993;22(4 Suppl A):6A-13A. The epidemiology of heart failure: the Framingham Study.
http://www.intertechnology.com/Trans_Tek/TransTek_Series_100.html, as accessed on Feb. 11, 2013.
Tavakoli M. et al. Haptics for Teleoperated Surgical Robotic Systems. pp. 13-30. *World Scientific Publishing Company* 2007.
V Dambrauskaite, et al. "The Evaluation of Pulmonary Hypertension Using Right Ventricular Myocardial Isovolumic Relaxation Time", *J. Am. Soc. Echo*. 2005, 18:1113-20.
P. Caso, et al. "Association between myocardial right ventricular relaxation time and pulmonary atrial pressure in chronic obstructive lung disease analysis by Pulsed Doppler tissue imaging". *J. Am. Echo*. 2001, 14:970-77.
Guido Dehnhardt, Björn Mauck & Horst Bleckmann. *Nature* 394, 235-236 (Jul. 16, 1998) | doi:10.1038/28303.
Ansalone et al., *JACC* 2002.
Bordacher et al., *JACC* Dec. 7, 2004.
Sogaard, *J. Am Coll Cardiol*, 2002. 40: p. 723-720.
Van Gelder, Berry M., Bracke, Frank A., Meijer, Albert, Lakerveld, Lex JM, Pijls, Nico HJ, "Effect of optimiaing the VV interval on left ventricular contractility in cardiac resynchronization therapy." *Am J Cardiol*, 2004. 93: p. 1500-1503.
Villard E, Dubosscq-Bidot L, Charron P, et al. *Eur Heart J* 2005; 26:795-803.
Daruwala RS, Rudra A, Ostrer H, et al., "A versatile statistical analysis algorithm to detect genome copy number variation:" *Proceedings of the National Academy of Sciences of the United States of America*, Nov. 16, 2004; 101 (46): 16292-7.
Breast Cancer Risk Assessment Tool, http://www.cancer.gov/bcrisktool/, as accessed on Feb. 11, 2013.
Gail Model and NSABP Model, http://www.halls.md/breast/riskcom.htm, as accessed on Feb. 11, 2013.
Selker et al., Patient specific predictions of outcomes in myocardial infarction for real-time emergency use: a thrombolytic predictive instrument. *Ann Intern Med* 1997; 127: 538-56.

Zhang Q. et al., "Assessment of the Effect of Cardiac Resynchronization Therapy on Intraventricular Mechanical Sychronicity be Regional Volumetric Changes." *Am J Cardiol* 2005; 95: 126-129.
Saxon LA, Ellenbogen KA. "Resynchronization Therapy for the Treatment of Heart Failure." *Circulation* 2003; 108: 1044.
Santomauro M et al. "Left ventricular pacing in patients with heart failure: evaluation study with Fourier analysis of radionuclide venticulography." *Ital Heart J* 2004; 5 (12): 906-911.
EUROPA—Press Release—Digital Agenda: European robots helping to perform safer, quicker brain surgery, Nov. 28, 2011.
U.S. Appl. No. 60/634,165, filed Dec. 8, 2004.
Sinnamon LJ, Saad MM, Bowman RM, Gregg JM. "Exploring grain size as a cause for "dead-Layer" effects in thin film capacitors." *Appl. Phys. Lett*. 2002. 81, 703-705.
Sai N. Kolpak AM, Rappe AM. "Ferroelectricity in ultra-thin perovskite films." *Phys. Rev*. 2005. B 72, 020101R.
Shiyou Xu et al 2006 Nanotechnology 17 4497-4501, doi:10.1088/0957-4484/17/17/036.
Nanosprings: Helical Piexoelectric Nanostruxtures Could be Actuators & Transducers in Future Nanosystems, Georgia Tech Research News, http://gtresearchnews.gatech.edu/newsrelease/nanosprings.htm, Oct. 16, 2003.
Cardon nanotube, http://en.wikipedia.org/wiki/carbon_nanotubes, as accessed on Feb. 11, 2013.
Nanotubes-101 Presentation, http://www.cheaptubesinc.com/Carbon-Nanotubes-101.htm, as accessed on Feb. 11, 2013.
Yang, S., Researchers create first ever integrated silicon circuit with nanotube transistors, http://www.berkeley.edu/news/media/releases/2004/01/05_nano.shtml, Jan. 5, 2004.
Philip G. Collins and Phaedon Avouris (2000), Nanotubes for Electronics—*Scientific American* Dec. 2000, 62-69.
Wittkampf FHM et al. "LocalLisa, New Technique for Real Time 2 Dimensional Localization of Regular Intracardiac Electrodes." *Circulation* 1999; 99: 1312-1317.
Packer DL, "Three-Dimensional Mapping of Interventional Electrophysiology: Techniques and Technology." Journal of Cardiovascular Electrophysiology 2005; vol. 16, No. 10, 1110-1117.
Packer DL, "Evolution and mapping and anatomic imaging of cardiac arrhythmias." J Cardiovasc Electrophysiol 2004; 15: 839-854.
Gruner, G., "Carbon Nanotube Films for Transparent and Plastic Electronics." *Journal of Materials Chemistry* 2006, vol. 16, No. 35, pp. 3533-3539.
Gruner, G., "Carbon Nanotube Transistors for Biosensing Applications." *Analytical and Bioanaoytical Chemistry* 2006. vol. 384, pp. 322-335.
Ou, Fung Suong; *Applied Physics Letters* Dec. 2006.
http://bios.ewi.utwente.nl/, as accessed on Feb. 11, 2013.
http://www.mic.dtu.dk/, as accessed on Feb. 11, 2013.
http://www.eng.monash.edu.au/mnrl, as accessed on Feb. 13, 2013.
http://www.appchem.t.u-tokyo.ac.jp/index_e.html, as accessed on Feb. 13, 2013.
http://biomems.uwaterloo.ca/index.html, as accessed on Feb. 11, 2013.
Hocini M, Sanders P, Jais P et al. "Techniques for Curative Treatment of Atrial Fibrillation." *Journal of Cardiovascular Electrophysiology*, vol. 15, No. 12, Dec. 2004, p. 1467.
Oral H, Pappone C, Chugh A. "Circumferential Pulmonary Vein Ablation for Chronic Atrial Fibrillation." *NEJM* 354:9, Mar. 2, 2006, p. 934.
Nademmanee K, Mckenzie J, Koar E, et al. "A New Approach for Catheter Ablation of Atrial Fibrillation: Mapping of the Electrophysiologic Substrate." *JACC* vol. 43, No. 11, 2004. p. 2044.
Gonzalez MD, Otomo K, Shah N. "Transeptal Left Heart Catheterization for Cardiac Ablation Procedures." *J Interventional Cardiac Electrophysiology* 2001. 5, 89-95.
Pappone C, Santinelli V. "The Who, What, Why and How-to Guide for Circumferential Pulmonary Vein Ablation." *J Cardiovascular Electrophysiology* 2004. vol. 15, 1226-1230.
*Circulation*. 2001;104:2118.

(56) References Cited

OTHER PUBLICATIONS

Schecter et al. "Guiding Catheters with Side Holes Relieve Pressure Damping and Improve Coronary Blood Flow: Assessment with the Doppler Flowire." *Circulation* 1994; 90: 4, Part 2: 1-164.
Kaneko M, Kanayama N, Tsuji T. "Active Antenna for Contact Sensing." *IEEE Transactions on Robotics and Automation*, vol. 14, No. 2, Apr. 1998. 278-291.
Neimark MA, Andermann JL, Hopfield JJ, Moore CI. "Vibrissa Resonance as a Transduction Mechanism for Tactile Encoding." *J Neurosci*, Jul. 23, 2003. 23(16): 6499-6509.
Hartmann MJ, Johnson NJ, Towal RB, Assad C. "Mechanical Characteristics of Rat Vibrissae: Resonant Frequencies and Damping in Isolated Whiskers and in the Awake Behaving Animal." *J Neurosci*, Jul. 23, 2003. 23(16): 6510-6519.
Krupa DJ, Matell MS, Brisben AJ, Oliveira LM, Nicolelis MAL. "Behavorial Properties of the Trigeminal Somatosensory System in Rats Performing Whicker-Dependent Tactile Discriminations." *J Neurosci*, Aug. 1, 2001, 21(15): 5752-5763.
Solomon JH, Hartmann MJ. "Robotic whiskers used to sense features." *Nature* 2006, vol. 443, 525.
Hsu, JWR et al. "Directed spatial organization of zinc oxide nanorods." *Nano Lett.* 5, 83-86 (2005).
Yoshida N et al. "Validation of Transthoracic Tissue Doppler Assessment of Left Atrial Appendage Function." *J Am Soc Echocardiography* 2007; 20: 521-526.
Dubin et al. "Carbon nanotube Fibers are Compatible With Mammalian Cells and Neurons." *IEEE Transactions on Nanobioscience*, vol. 7, No. 1, Mar. 2008.
Berkelmann PJ, Whitcomb L, Taylor et al. A miniature microsurgical instrument tip force sensor for enhanced force feedback during robot-assisted manipulation. *IEEE Transactions on Robotics and Automation* 2003, 19 (5), 917-922.
Ezhilvalavan S. et al. *J. Phys* 2006. Conf. Ser. 34 979-984.
Stampfer, D.; Jungen, A.; Hierold, C. Sensors, 2004. *Proceedings of IEEE*. vol. , Issue , Oct. 24-27, 2004, pp. 1056-1059 vol. 2.
Singh et al. *Nanotechnology* 2007, 18 475501, abstract.
Hwang, J.D.; Williams, M.D.; Niemeyer, G. Proceedings. 12th International Symposium on Haptic Interfaces for Virtual Environment and Teleoperator Systems, 2004. Haptics apos; vol. 4, Issue, Mar. 27-28, 2004 pp. 24-31.
Sharifi F, Hayward V, Chen CJ. "Discrete-Time Adaptive Windowing for Velocity Estimation." *IEEE Transactions on Control Systems Technology* 8:6 (2000), 1003-1009.
Rougeron, M. et al. "A Control Approach for Real Time Human Grasp Simulation with Deformable Fingertips." *Intelligent Robots and Systems*, 2006 IEEE/RSJ International Conference Oct. 9-15, 2006 pp. 4634-4640.
Demersseman R et al. "Magnetorhelogical Brake for Haptic Rendering Haptics: Perception, Devices and Scenarios." 6th International Conference, Eurohaptics 2008, Madrid, Spain, Jun. 2008 Proceedings, pp. 940-945.
Khuri-Yakub et al. "Next-Gen Ultrasound." IEEE Spectrum, vol. 46, No. 5, p. 44-54, May 2009.
Campion G, and Hayward V. "Fundamental Limits in the Rendering of Virtual Haptic Textures." In Proc of the World Haptics Conference. pp. 263-270. Washington DC. IEEE Computer Society 2005.
McNeely et al. "Six Degree of Freedom Haptic Rendering using Voxel Sampling." In Proceedings of SIGGRAOH 99, Computer Graphics Proceedings, Annual Conference Series, Edited by Alyn Rockwood. pp. 401-408. Reading, MA: Addison Wesley Longman 1999.
Moreau JJ, and Jean M. "Numerical Treatment of Contact and Friction: The Contact Dynamics Method." Engineering Systems Design and analysis 4 (1996), 201-208.
Chuang J et al. Embeddable wireless strain sensor based on resonant RF carivites. Rev. Sci. Instrum., vol. 76, No. 9, p. 094703, 2005.
Rizzoli V, et al. A New Wireless Displacement Sensor Based on Reverse Design of Microwave and Millimeter-Wave antenna Array. IEEE Sensors Journal, vol. 9, No. 11, Nov. 2009. p. 1557.

Pulmonary Vein Stenosis Complicating Ablation for Atrial Fibrillation: Clinical Spectrum and Interventional Considerations. David R. Holmes, JrJ Am Coll Cardiol Intv, 2009; 2:267-276.
Pulmonary Vein Anatomy in Patients Undergoing Catheter Ablation of Atrial Fibrillation: Lessons Learned by Use of Magnetic Resonance Imaging. Kato R et al. Circulation. 2003; 107: 2004-2010.
Incidence and Predictors of Pulmonary Vein Stenosis Following Catheter Ablation of Atrial Fibrillation using the Anatomic Pulmnoary Vein Ablation Approach: Results from Paired Magnetic Resonance Imaging. Dong J et al. J Cardiovasc Electrophysiol 2005, vol. 16, pp. 845-852.
Dill T et al. Circulation 2003;107, 845-850.
Sorgente, A. et al. Europace (2011) 13 (2): 205-212.
Tomotsugu T et al. J Am Coll Cardiol, 2003; 41:1243-1250.
Robbins IM, Colvin EV, Doyle TP, et al. Pulmonary vein stenosis after catheter ablation of atrial fibrillation. Circulation. 1998; 98:1769-1775.
Gibson DN et al. Stiff left atrial syndrome after catheter ablation for atrial fibrillation: Clinical characterization, prevalence and predictors. Heart Rhythm, vol. 8, No. 9, 2011.
Tsao HM et al. J Cardiovasc Electrophysiol 2010; 21: 270-277.
Buber J. et al. J Am Coll Cardiol, 2011; 58:1614-1621.
S. Sherrit, G. Yang, H.D. Wiederick and B.K. Mukherjee, Temperature Dependence of the Dielectric, Elastic, Piezoelectric Material Constants of Lead Zirconate Titanate Ceramics, http://mastersonics.com/documents/mmm_basics/general_info/ultrasonics_faq/ferro29.pdf, 1999.
Hansoo Kim and Wolfgang Sigmund. Zinc oxide nanowires on carbon nanotubes. Appl. Phys. Lett. 81, 2085 (2002).
Kern TA. Engineering Haptic Devices. (Ed.) 2009, XXXI, 472 p. 243-276.
Tanaka, Y.; Doumoto, K.; Sano, A.; Fujimoto, H.; , "Development of a sensor system with syringe based on tactile sensing using balloon expansion," Robotics and Automation (ICRA), 2010 IEEE International Conference on , vol., No., pp. 4861-4866, May 3-7, 2010.
Tabata, T. et al. J Am Coll Cardiol, 2003; 41:1243-1250.
Friedman, PA. Heart Rhythm 2012; 9: 1046; "Hitting a Moving Target".
2012 HRS/EHRA/ECAS Expert Consensus Statement on Catheter and Surgical Ablation of Atrial Fibrillation published in Heart Rhythm, vol. 9, No. 4, Apr. 2012, 632-696, Europace Advance Access published Mar. 1, 2012.
ROBOCAST, ROBOt and sensors integration for Computer Assisted Surgery and Therapy, Dec. 31, 2010.
Indian Pacing Electrophysiol. J. 2012; 12(2): 39-53.
Andrade JG et al. Heart Rhythm 2011; 8(9): 1444-1451.
United States Army Research Laboratory: A Review and Meta Analysis of Vibrotactile and Visual Information Displays, Elliott et al, ARL-TR-4955, Sep. 2009.
Chun KR et al. J Cardiovasc Electrophysiol. 2009; 20(11)1203-1210.
Sarabanda AV et al. JACC 2005;46(10):1902-1912.
Chiba S et al. Electroactive Polymer "Artificial Muscle" Operable in Ultra-High Hydrostatic Pressure Environment. IEEE Sensors Jounral, vol. 11, No. 1, Jan. 2011, p. 3.
Wu J et al. Proc. IMechE vol. 220 Part D: Automobile Engineering. p. 313, 2006.
KurzweilAI, Accelerating Intelligence.news, Tactile technology guaranteed to send shivers down your spine, Aug. 9, 2011.
Leitmann G. Applied Mathematics and Computation 1995 70: 247-259.
Han Y et al. Smart Mater. Struct 20 (2011) 075019, Abstract.
Kesner, S.B.; Howe, R.D.; , "Discriminating tissue stiffness with a haptic catheter: Feeling the inside of the beating heart," World Haptics Conference (WHC), 2011 IEEE, pp. 13-18, Jun. 21-24, 2011.
"Growth and replication of ordered ZnO nanowire arrays on general flexible substrates" Su Zhang, Yue Shen, Hao Fang, Sheng Xu, Jinhui Song and Zhong Lin Wang, J. Mater. Chem., J. Mater. Chem., Sep. 2010.

(56) References Cited

OTHER PUBLICATIONS

"Cellular Level Biocompatibility and Biosafety of ZnO Nanowires" Zhou Li, Rusen Yang, Min Yu, Fan Bai, Cheng Li and Zhong Lin Wang, J. Phys. Chem. C, 112 (2009) 20114-20117.
"Piezoelectric-Potential-Controlled Polarity-Reversible Schottky Diodes and Switches of ZnO Wires", Jun Zhou, Peng Fei, Yudong Gu, Wenjie Mai, Yifan Gao, Rusen Yang, Gang Bao, and Z.L. Wang, Nano Letters., 2008.(8),11. 3973-3977.
"Elastic Properties and Buckling of Silicon Nanowires", Cheng-Lun Hsin, Wenjie Mai, Yudong Gu, Yifan Gao, Chi-Te Huang, Yuzi Liu, Lih-Juann Chen, and Z.L. Wang, Advanced Materials., 2008 (20) 20, 3919-3923.
"Flexible Piezotronic Strain Sensor", J. Zhou, Y.D. Gu, P. Fei, W.J. Mai, Y.F. Gao, R.S. Yang, G. Bao and Z.L. Wang Nano Letters, 2008, 8(9),3035-3040.
"Mechanical-Electrical Triggers and Sensors Using Piezoelectric Micowires/Nanowires", J. Zhou, P. Fei, Y.F. Gao, Y.D. Gu, J. Liu, G. Bao and Z.L. Wang Nano Letters, 2008, 8(9), 2725-2730.
"Fabrication of ZnO Nanowire Devices via Selective Electrodeposition", Min Zhang, Zhaoying Zhou, Xing Yang, Xiongying Ye, and Zhong Lin Wang. Electrochemical and Soild-State Letters,11(9) D69-D71 (2008).
Electrostatic Potential in a Bent Piezoelectric Nanowire. The Fundamental Theory of Nanogenerator and Nanopiezotronics, Y.F. Gao and Z.L. Wang Nano Lett., 7 (2007) 2499-2505.
The new field of nanopiezotronics, Z.L. Wang, Materials Today, 10 (2007) 20-28.
Nanowire Piezoelectric Nanogenerators on Plastic Substrates as Flexible Power Sources for Nanodevices, P.G. Gao, J.H. Song, J. Liu and Z.L. Wang Adv. Mater., 19 (2007) 67-72.
Piezoelectric Nanogenerators Based on Zinc Oxide Nanowire Arrays, Z.L. Wang and J.H. Song Science, Apr. 14, 2006: 242-246.
"Pattern and Feature Designed Growth of ZnO Nanowire Arrays for Vertical Devices", J. H. He, J. H. Hsu, C. H. Wang, H. N. Lin, L. J. Chen and Z. L. Wang, J. Phys. Chem. B, 110 (2006) 50-5.
Heart Rhythm, vol. 9, No. 1, Jan. 2012 p. 18-23.
Kim MH et al. Circ Cardiovasc Qual Outcomes 2011; DOI:10.1161/CIRCOUTCOMES.110.951865; AHA.
NEJM 2002; 347: 1825-1833.
Dagres N. et al. J Cardiovasc Electrophys Sep. 2009; 20(9): 1014-1019.
Dong, J et al, J Cardiovasc Electrophysiol, vol. 16, pp. 845-852, Aug. 2005.
J Am Coll Cardiol, 2006; 47:2498-2503, doi:10.1016/j.jacc.2006.02.050.
Vibrotactile Rendering for a Traveling Vibrotactile Wave Based on a Haptic Processor. Sang-Youn Kin and Jeong Cheol Kim. IEEE Transactions on Haptics, vol. 5, No. 1, Jan.-Mar. 2012.
Smooth Vibrotactile Flow Generation using two Piezoelectric Actuators. Kang J. et al. IEEE Transactions on Haptics, vol. 5, No. 1, Jan.-Mar. 2012, pp. 21-32.
Andreu, D, Displacement of the target ablation site and ventricles during premature ventricular contractions: Relevance for radiofrequency catheter ablation, Heart Rhythm, vol. 9, Issue 7 , p. 1050, Jul. 2012.
Kesner, S.B.; Howe, R.D.; , "Discriminating tissue stiffness with a haptic catheter: Feeling the inside of the beating heart," World Haptics Conference (WHC), 2011 IEEE Abstract, Jun. 29, 2011.
Yuen, S. et al, Robotic Tissue Tracking for Beating Heart Mitral Valve Surgery, Medical Image Analysis, p. 1-11, Jun. 14, 2010.
Yuen, S. et al, Force Tracking with Feed-Forward Motion Estimation for Beating Heart Surgery, IEEE Transactions on Robotics, vol. 26, No. 5, Oct. 2010, p. 888-896.
Yuen, S. et al, Robotic Motion Compensation for Beating Heart Intracardiac Surgery, The International Journal of Robotics Research, p. 2-18, 2009.
Kesner, Samuel et al, Design of a Motion Compensated Tissue Resection Catheter for Beating Heart Cardiac Surgery, Proceeding of the 2011 Design of Medical Devices Conference, DMD2011-5271, Apr. 12-14, 2011 Minneapolis, MN USA, p. 1-6.
Kesner, S. et al., Position Control of Motion Compensation Cardiac Catheters, p. 1-10, Oct. 28, 2010.
Zorcolo, A. et al, Catheter Insertion Simulation with Combined Visual and Haptic Feedback, 1999.
Haruta, M et al., Development of Remote-Type Haptic Catheter Sensor System using Piezoelectric Transducer, Extended Summary, p. 5, 2007.
Bethea, B. et al., Application of Haptic Feedback to Robotic Surgery, J Laparoendosc Adv Surg Tech A. Jun. 2004; 14(3): 191-195.
Ouellette, Jennifer, Smart Fluids Move into the Marketplace, The Industrial Physicist, Dec. 2003/Jan. 2004, p. 14-17.
Patel, Nikunj Manubhai, Design of Haptic Force Feedback for Catheter Insertion Mechanism, Dec. 2006.
Pare, Michel; Joseph E. Mazurkiewicz, Allan M. Smith, and Frank L. Rice (Sep. 15, 2001). "The Meissner Corpuscle Revised: A Multiafferented Mechanoreceptor with Nociceptor Immunochemical Properties". The Journal of Neuroscience, Sep. 15, 2001, 21(18): 7836-7246.
Kumar, Saurabh et al., Effect of respiration on catheter-tissue contact force during ablation of atrial arrhythmias, Heart Rhythm 2012; 9: 1041-1047.
Howe, E., The Plymouth Student Scientist, 2009, 2, (1), 90-107.
Savazzi, S. et al., Interhemispheric transfer following callosotomy in humans: Role of the superior colliculus, Neuropsychologia 45 (2007) 2417-2427.
Zhu R, Zhou Z. A Small Low Cost Hybrid Orientation System and Its Error Analysis, IEEE Sensors Journal, vol. 9, No. 3, Mar. 2009.
Han J, Shannon MA. Smooth Contact Capacitive Pressure Sensors in Touch and Peeling-Mode Operation. IEE Sensors Journal, vol. 9, No. 3, Mar. 2009.
Metzner A, et al. Heart Rhythm, vol. 9, No. 9, Sep. 2012.
U.S. Appl. No. 60/647,102, filed Jan. 1, 2005.
U.S. Appl. No. 60/660,101, filed Mar. 9, 2005.
U.S. Appl. No. 11/334,935, filed Jan. 19, 2006, Published as Patent Pub. No. 20060167529A1 on Jul. 27, 2007, Abandoned.
U.S. Appl. No. 11/584,465, filed Oct. 20, 2006, Abandonded.
U.S. Appl. No. 11/686,602, filed Mar. 15, 2007, now U.S. Pat. No. 7,963,925 on Jun. 21, 2011.
U.S. Appl. No. 11/746,752, filed May 1, 2007, Abandoned.
U.S. Appl. No. 11/771,233, filed Jun. 29, 2007, Abandoned.
U.S. Appl. No. 11/848,346, filed Aug. 31, 2007, Abandoned.
U.S. Appl. No. 12/245,058, filed Oct. 3, 2008, Published as Patent Pub. No. 20090030332A1 on Jan. 29, 2009, Abandoned.
U.S. Appl. No. 12/836,636, filed Jul. 15, 2010, Published as Patent Pub. No. 20100312129A1 onDec. 9, 2010, Abandoned.
U.S. Appl. No. 13/337,807, filed Dec. 27, 2011, Published as Patent Pub. No. 20120265076A1 on Oct. 18, 2012.
U.S. Appl. No. 13/448,879, filed Apr. 17, 2012, Published as Patent Pub. No. 20120265083A1 on Oct. 18, 2012.
U.S. Appl. No. 60/855,820, filed Nov. 1, 2006.
U.S. Appl. No. 61/270,924, filed Jul. 15, 2009.
U.S. Appl. No. 61/396,575, filed May 29, 2010.
U.S. Appl. No. 61/341,129, filed Mar. 27, 2010.

\* cited by examiner

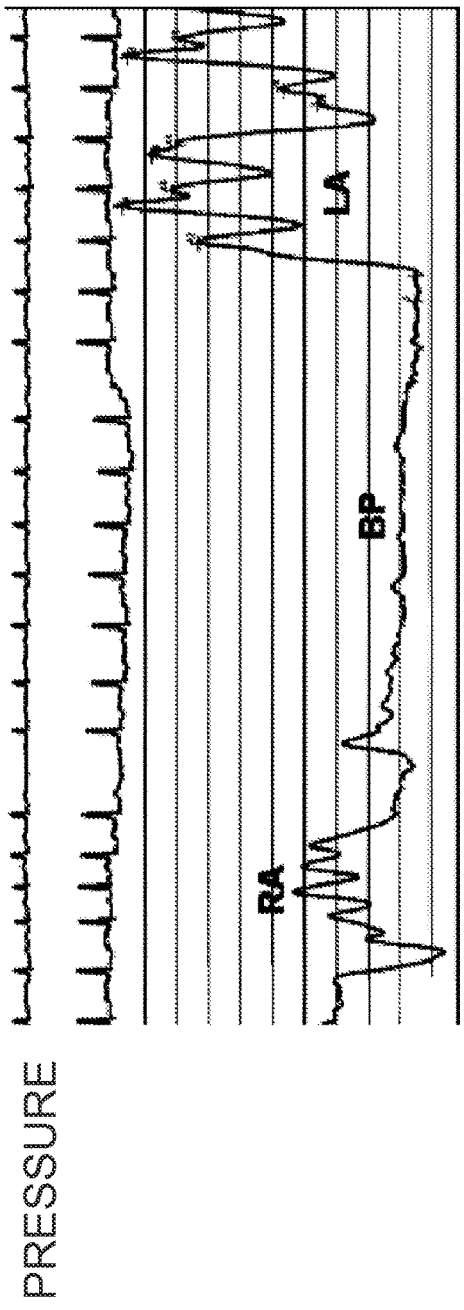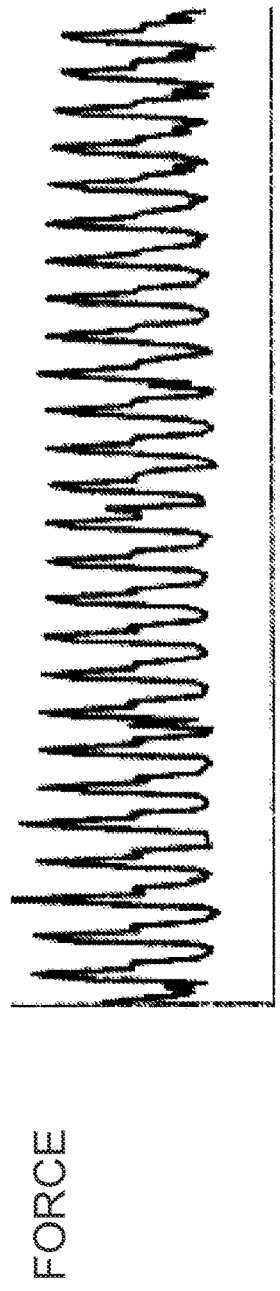

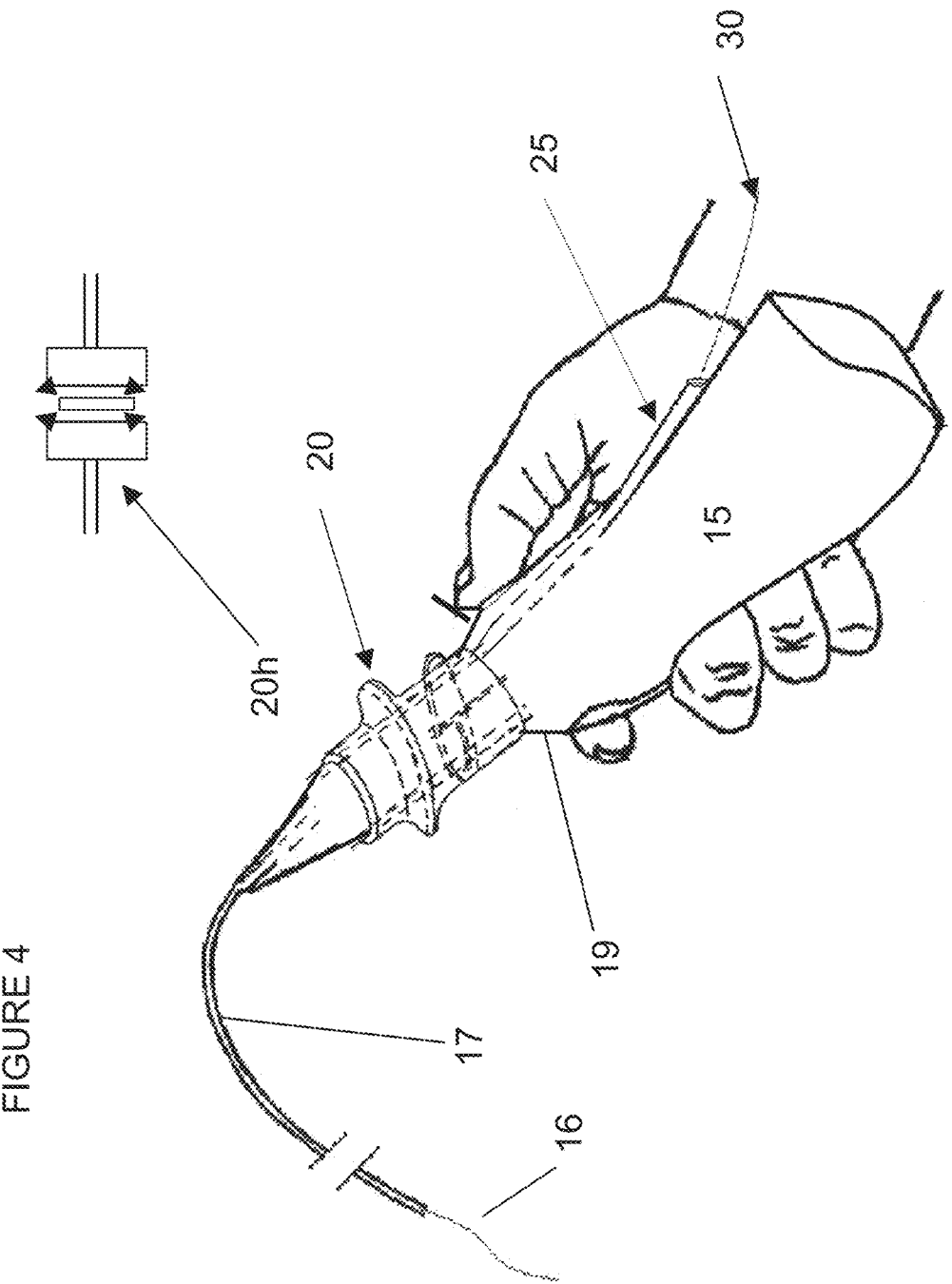

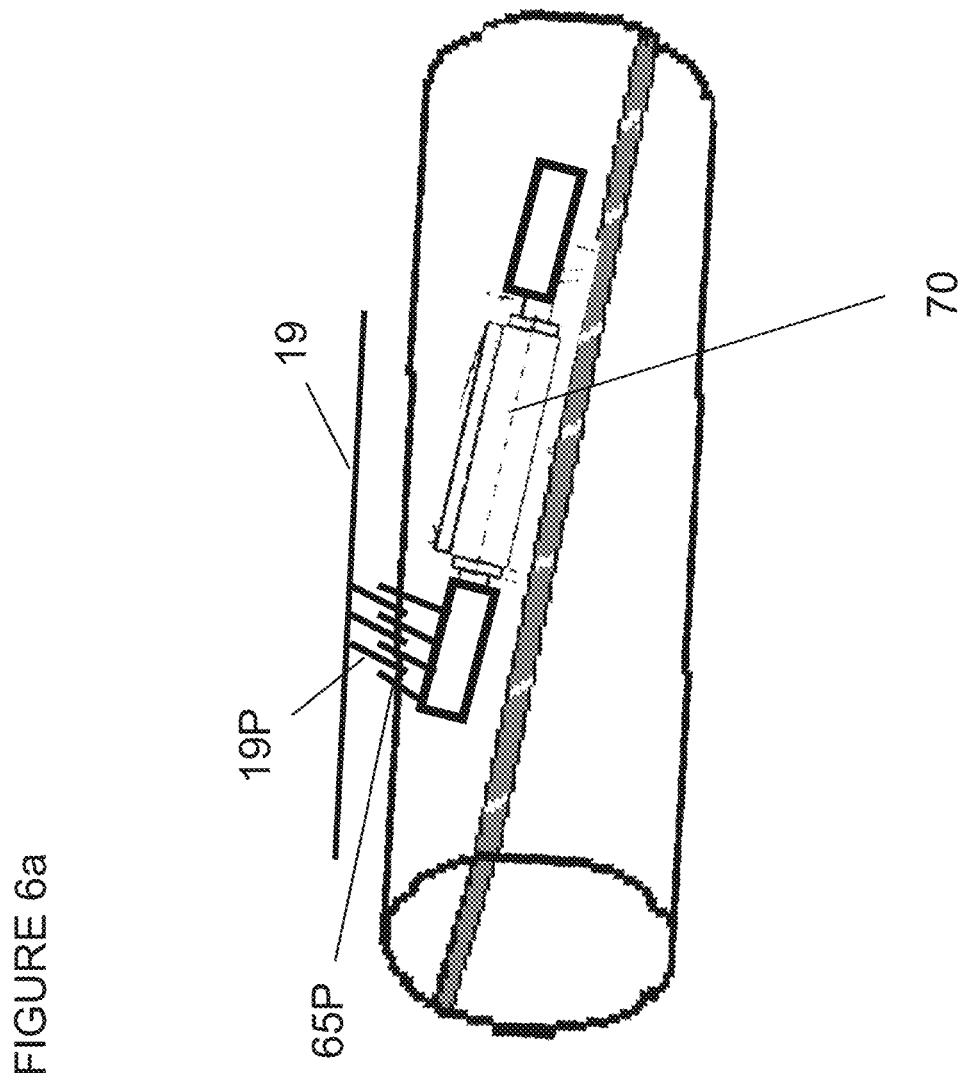

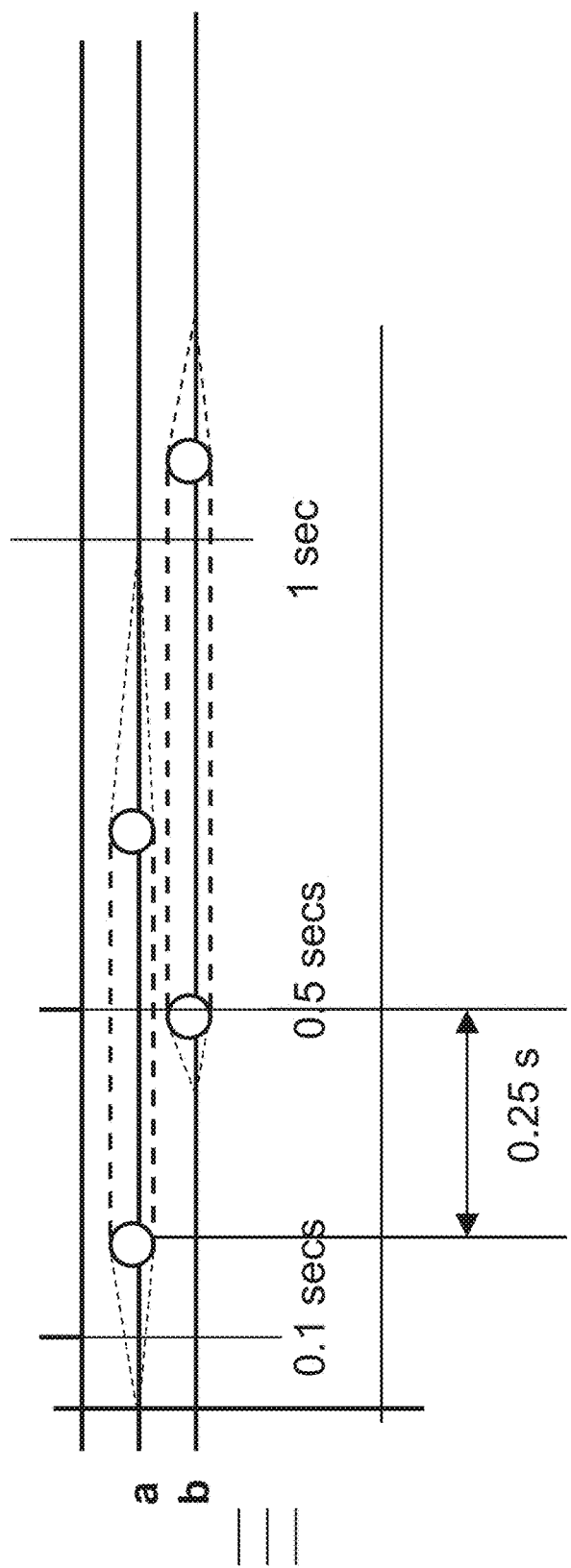

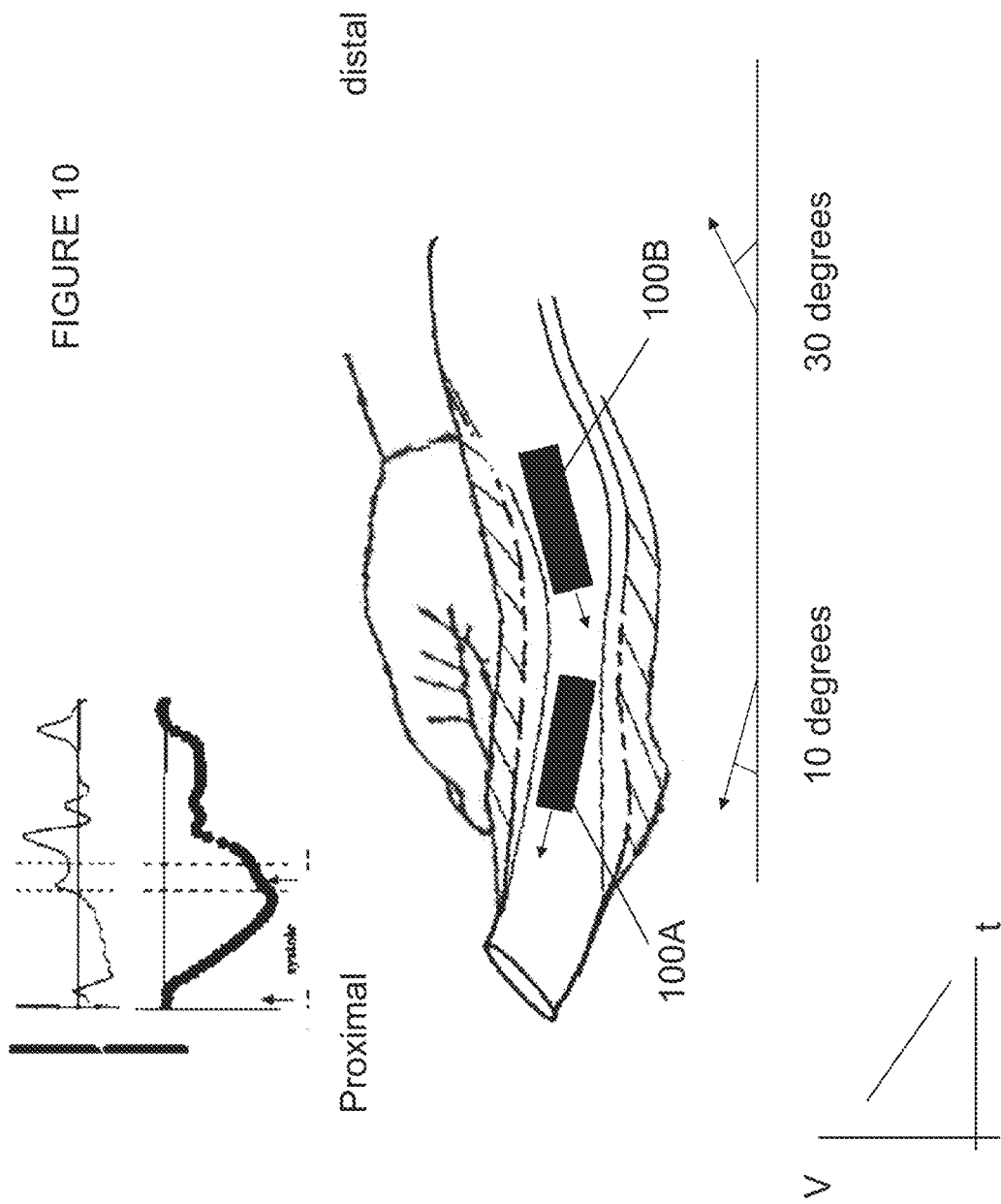

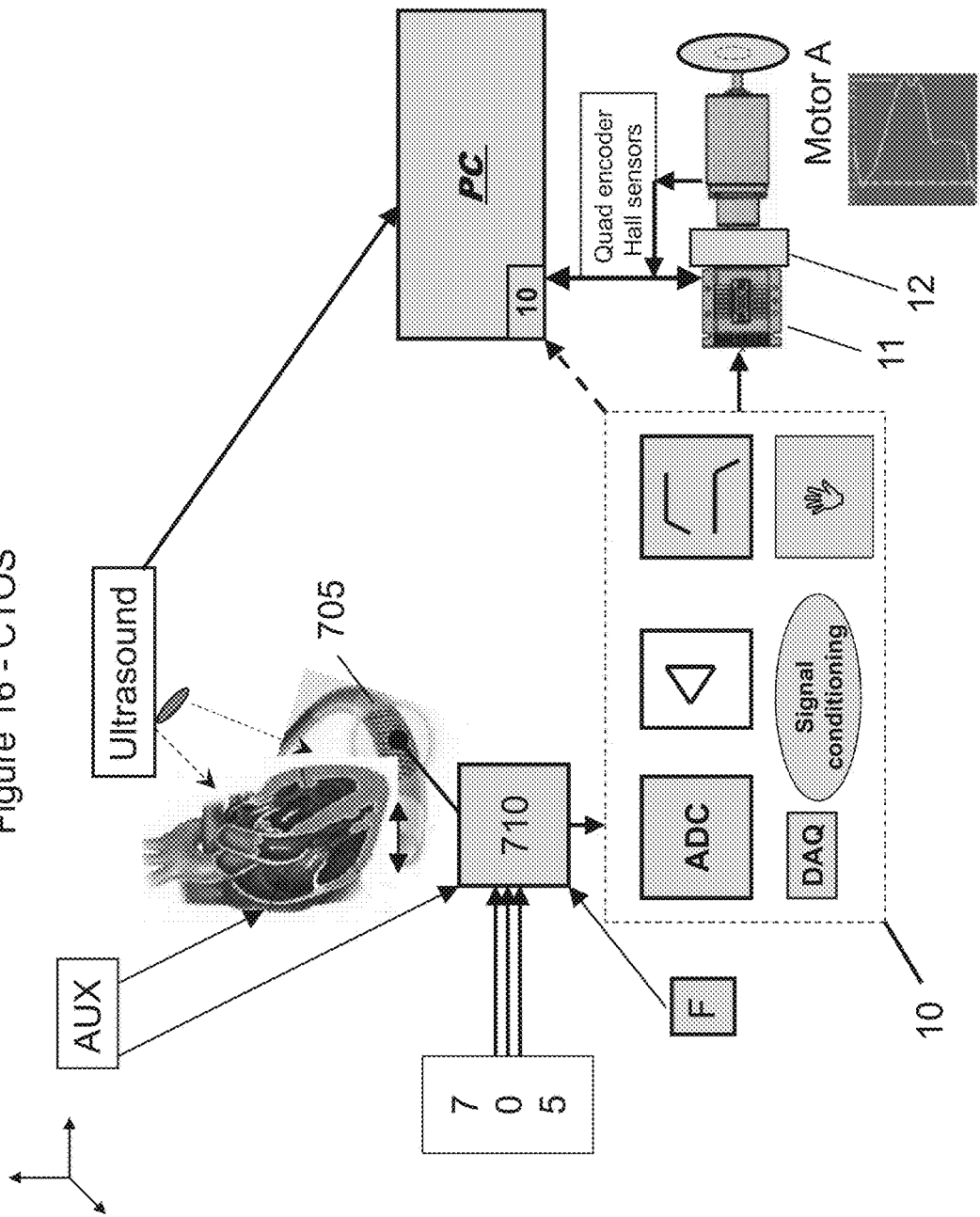
Figure 16 - CTOS

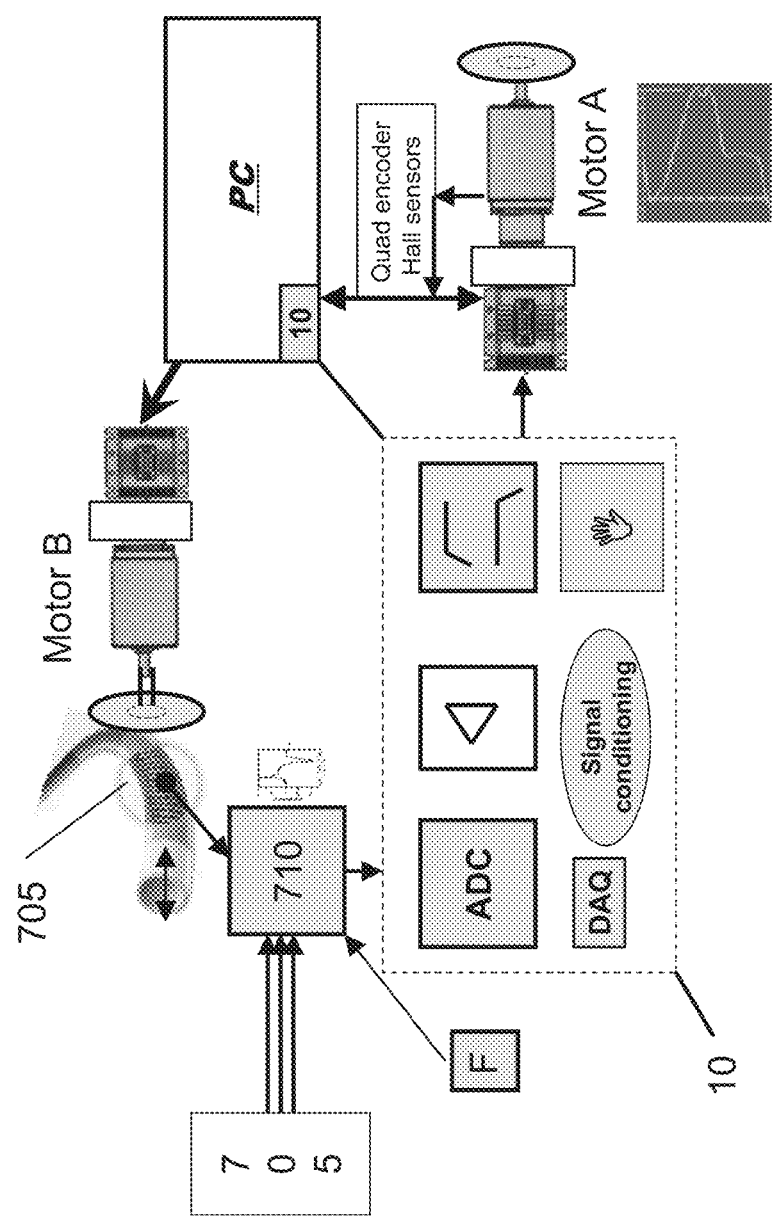
Figure 17 – CTOS Testing

OPERATING SYSTEM WITH HAPTIC INTERFACE FOR MINIMALLY INVASIVE, HAND-HELD SURGICAL INSTRUMENT

The present application claims the benefit of U.S. Provisional Application No. 61/655,804 entitled OPERATING SYSTEM WITH HAPTIC INTERFACE FOR MINIMALLY INVASIVE, HAND-HELD SURGICAL INSTRUMENT and filed Jun. 5, 2012, which is incorporated herein in its entirety by reference.

FIELD OF THE INVENTION

The inventions herein relate to operating and control systems and methods for a minimally invasive, hand-held surgical interface. More particularly, the present inventions relate to various embodiments that allow a user to control the position and functioning of an end-effector of a minimally invasive, hand-held surgical instrument while sensing organ characteristics, motion of moving biological organs, characteristics of blood flow, and physiologically relevant properties of biological tissues. Moreover, the present invention enables the user to control his or her own interactive experience (user programmability) through haptic and graphical user interfaces while performing diagnostic and therapeutic interventions. Some such interventions may include cardiac catheterization, therapeutic delivery of endovascular or coronary stents, electrophysiology/ablation procedures, deployment or extraction of pacing or defibrillation leads and electrodes, delivery of devices for left atrial appendage closure, transeptal puncture, and valvular replacement or repair. In some embodiments, user based modifications are implemented to formulate and define specific haptic formats that can be chosen as a default haptic interface from a list of optional settings which do not affect the timing of salient sensed signals.

BACKGROUND OF THE INVENTION

In the relatively brief history of minimally invasive surgery (MIS) and percutaneous procedures, the clinician has always been at a relative disadvantage with regard to anatomical visibility and real-time tactile feedback. As a result, such MIS procedures typically require one or more extra incisions to accommodate a camera or endoscope to facilitate the success of the procedure. The additional incisions and apparatus deployed into a patient can cause unwarranted issues that ideally would be minimized if possible and do not provide for touch feedback. Procedures done with MIS or via percutaneous approaches do not enable the operator to tactually appreciate relevant physiological information upon instrument contact with biological tissues and blood. Furthermore, there is no available means for controlling the methods for data acquisition, data processing or the modes for presenting such data to the user via a haptic interface. Accordingly, the ability to convey information and control a user's interactive experience through a haptic interface while operating surgical instruments and diagnostic devices through a common control and user interface arrangement is desirable.

One approach to a common control user interface for MIS surgical instruments utilizes some form of haptic or tactile feedback technology. Currently available haptic technologies include, for example, programmable haptic keyboards, augmented mice, trackballs, joysticks, multi-dimensional point and probe-based interactions, exoskeletons, vibrotactor arrays, gloves, and isometric devices.

Simplified tactile haptic interface devices have long been used in game controllers. In the context of the medical field, haptic technology has been used principally to simulate medical procedures in the virtual world, for example, for teaching purposes.

In some cases, medical companies have implemented haptic feedback systems that provide notification signals and vibrotactile sensations as an alert when too much force is applied or to direct a user controlling robotic and tele-surgical operative systems. However, these systems do not provide the operator with tangible sensations that are physiologically relevant, nor do they provide a corresponding visual user interface that conveys such tactile information while providing a means for the operator to control their interaction and experience with the haptic interface and inserted instrumentation.

Prior work of the present inventor, Dr. Stuart O. Schecter, in the area of haptics includes: U.S. Pat. No. 7,963,925, entitled "Method and Apparatus for Defining the Effect of Atrial Arrhythmias on Cardiac Performance And Directing Therapy Using a Plurality of Intrinsically and Extrinsically Derived Signals," which discloses a catheter with a sensor and handle arrangement that provides real-time, proportional haptic feedback, U.S. Pat. Pub. No. 2009-0030332 A1, entitled "Microfabricated Cardiac Sensor with Tactile Feedback and Method and Apparatus for Calibrating the Same Using a Plurality of Signals," and U.S. Pat. Pub. No. 2010-0312129 A1, entitled "Cardiovascular Haptic Handle System."

While these patents and applications provide new and novel systems and methods for minimally invasive, hand-held surgical interfaces with haptic feedback, it would be desirable to provide improvements that can allow a user to monitor and control his or her own interactive experience through haptic and graphical user interfaces during diagnostic and therapeutic interventions.

SUMMARY OF THE INVENTION

Embodiments of the present invention relate to an integrated, haptic system for a minimally invasive, hand-held surgical instrument that can include a graphical user haptic interface (GUHI), one or more haptic interfaces associated with a hand-held handle used to control a sensorized end-effector of the surgical instrument or inserted catheters, and associated hardware and operating system. Various embodiments enable users to acquire, read, modify, store, write, and download sensor acquired data in real time, and can provide: an open, universally compatible platform capable of sensing or acquiring physiological signals/data (referred to as sensor acquired data) in any format; processing of the sensor acquired data within an operating system; and output of processed signals to hardware which generates tangible sensations via one or more haptic interfaces. These tangible sensations are able to be modified by the user in real time via the GUHI, while the system ensures that the temporal relationship of sensed fiducial events are not altered or shifted relative to the generated and displayed haptic signals.

In various embodiments, the GUHI communicates with the operator using a symbolic language descriptive of biological tissues physical properties and the characteristics of motors and actuators that constitute the interactive components of one or more haptic interfaces (e.g., haptic handle). In one embodiment, the GUHI is a touch screen interface (e.g., as a glass display upon a hand-held handle) which can provide haptic signals to the user and is thus an active display with touch and/or force feedback that programs the one or more haptic interfaces (e.g., hand-held controller/handle). The GUHI can include haptic signals that confirm programming (e.g., palpable click) and provide additional sensor feedback that is descriptive of the events occurring in the haptic interfaces in real time (e.g., vibrotactile feedback, haptic rendering of physiologic events, audible and visual cues). The haptic interface(s) is at least and preferably in the form of a hand-held handle connected to an elongated member used to perform surgical procedures and in a preferred embodiment, the elongated member also generates haptic signals. The handle, in one embodiment, not only provides haptic feedback, but also functions as a user interface for programming purposes.

In various embodiments, the symbolic language communicated by the GUHI creates a new paradigm which provides a universal approach for describing and communicating haptic signals that are based on sensor acquired data in the frequency and time domains and enables a user-friendly means for understanding, interacting with and controlling hardware, firmware and programming software in real time. The Operating System (OS) utilizes the handheld haptic interfaces that may comprise motors, actuators, and haptic elements. In one embodiment, these components are located within a plug-in attachment that connects and functions with disposable, exteriorized equipment (e.g. medical instrumentation, sensorized catheter), and the associated hardware (e.g. processors/computers). The plug-in attachment is ideally hermetically sealed and isolated from having contact with the external environment thereby protecting it from inclement conditions and exposure to bodily fluids and at the same time maintaining sterility, though in one embodiment the entire unit is disposable. The plug-in attachment reflects the inner workings of the haptic handle interface and connects with the display or GUHI enabling the user to modify their haptic experience to suit their personal preferences without altering the data's temporal relationship with physiological and physical events (e.g. time of tissue-catheter contact, time of onset of tissue motion during the cardiac cycle).

In one embodiment, modification of the haptic experience of a user can be accomplished in real time (e.g. during procedures). This can be accomplished via the GUHI that can be used to modify code and program software to optimize system functionality for an individual operator or enable multiple operators to modify a finalized system that is optimized based on their user group's preferences. In some embodiments, visual icons, and secondary notations comprise a simplified graphical format similar to that commonly seen with the notations and symbols used with musical scores and is augmented with haptic feedback that reflects relevant physiological information as described in more detail below. A preference list consisting of default options can be made available to other operators if the user group desires. Research surveys based out of different institutions can be conducted to create and identify the best programs and operating system features to choose from. The GUHI serves as a commonly used interface and communicates with a language that enables clinicians to communicate and understand a variety of features and differing haptic formats both quantitatively and qualitatively.

The programmable GUHI and haptic handle interfaces provide a means to display data acquired from one or more sensors and control the corresponding actions of one or more actuators or haptic elements within the haptic handle interfaces which are designed to recreate the sensor acquired data. These technologies bridge the gap between sensor acquired data and haptic display.

Embodiments of the invention can include a haptic handle interface with both a palm facing haptic element and a non-palm facing haptic element. In other embodiments, one or more haptic elements are provided in a handle that is adapted to be held in one hand and at least another haptic element is provided associated with a shaft of a catheter or inserted surgical instrumentation and adapted to be held in the other hand.

One embodiment of the present invention is an operating system providing user customization of a haptic handle interface. The operating system includes a computer processor operatively coupled to a non-transitory data storage medium containing instructions that when executed cause the computer processor to receive real time sensor acquired data from a catheter or surgical instrument and process the sensor acquired data to create a plurality of processed signals. The instructions further cause the processor to output the plurality of processed signals to hardware configured to recreate tangible sensations via at least one haptic handle interface and a graphical user haptic interface configured in response to user customized programming. Further, the instructions cause the processor to modify the processed signals in real time based on the user customized programming received from the graphical user haptic interface without altering the temporal relationship of the real time sensor acquired data and the sensed physiological and physical events while enabling adjustments to the tangible sensations recreated on the haptic handle interface.

A further embodiment of the invention includes a method for operating a system including a haptic handle with a user customizable haptic handle interface, an elongate medical device with sensorized distal end, and a graphical user haptic interface. The method includes receiving sensor acquired data with the elongate medical device, processing the sensor acquired data to create a plurality of processed signals, and outputting the plurality of processed signals to hardware that communicates tangible sensations to an operator via one or more haptic displays on a haptic handle interface and a graphical user haptic interface. The method further includes implementing customized programming changes received from the graphical user haptic interface that do not alter the temporal relationship of sensor acquired data and associated physiological and physical events.

Another embodiment of the invention includes a method for operating a system including a haptic handle with a user customizable haptic handle interface coupled to an elongate member. The method includes obtaining sensor data from distally located sensors on the elongate member, utilizing the sensor data to provide a haptic recreation of sensed information on a haptic handle interface of the haptic handle, and using a graphical user interface to customize a haptic display of the haptic handle interface by permitting adjustments to one or more of the: amplitude of the tangible sensations; quality of the tangible sensations; and subjective haptic preferences of a user; without altering the temporal relationship of the sensor data with associated physiological and physical events.

Another embodiment of the invention includes a user interface. The user interface includes a haptic handle interface and a graphical user haptic interface. The haptic handle interface is configured to couple with an elongate member having distally located sensors which acquire data from moving biological tissue. The haptic handle interface includes at least one component that provides real time tangible sensations that supply haptic recreations of physical, physiological, and anatomical data. In this embodiment, the graphical user haptic interface permits user customization of the real time tangible sensations of the haptic handle interface without altering the temporal relationship of the sensor data with associated physiological and physical events.

BRIEF DESCRIPTION OF THE DRAWINGS

The invention may be more completely understood in consideration of the following detailed description of various embodiments of the invention in connection with the accompanying drawings, in which:

FIGS. 3c and 3d illustrate sensor-acquired data in real time that is input into the operating system, including pressure and force time curves, respectively.

FIG. 4 illustrates another view of a haptic-enabled medical device handle having haptic feedback for an operator, according to an embodiment of the invention.

FIG. 4a illustrates a spring-loaded piezoactuator that provides haptic control and mechanical control of interlocking catheters, according to an embodiment of the invention.

FIG. 6a illustrates an example of haptic feedback relay to an operator via the haptic handle, according to an embodiment of the invention.

FIG. 9 depicts an exemplary 'musical score' type depiction of haptic response from more than two haptic transducers, according to an embodiment of the invention.

FIG. 10 depicts in a compound view a relationship between the response of a deformable haptic-enabled medical device handle and a distal catheter disposed within the heart chambers of a mammal, according to an embodiment of the invention.

FIG. 16 illustrates an embodiment of the OS having Hall Effect sensors/encoders and appropriate circuitry, according to an embodiment of the invention.

FIG. 17 provides an illustration of a testing system for a OS of FIG. 16, according to an embodiment of the invention.

DETAILED DESCRIPTION OF THE PREFERRED EMBODIMENTS

The invention may be embodied in other specific forms without departing from the essential attributes thereof. The illustrated embodiments should be considered in all respects as illustrative and not restrictive.

Figure 1:
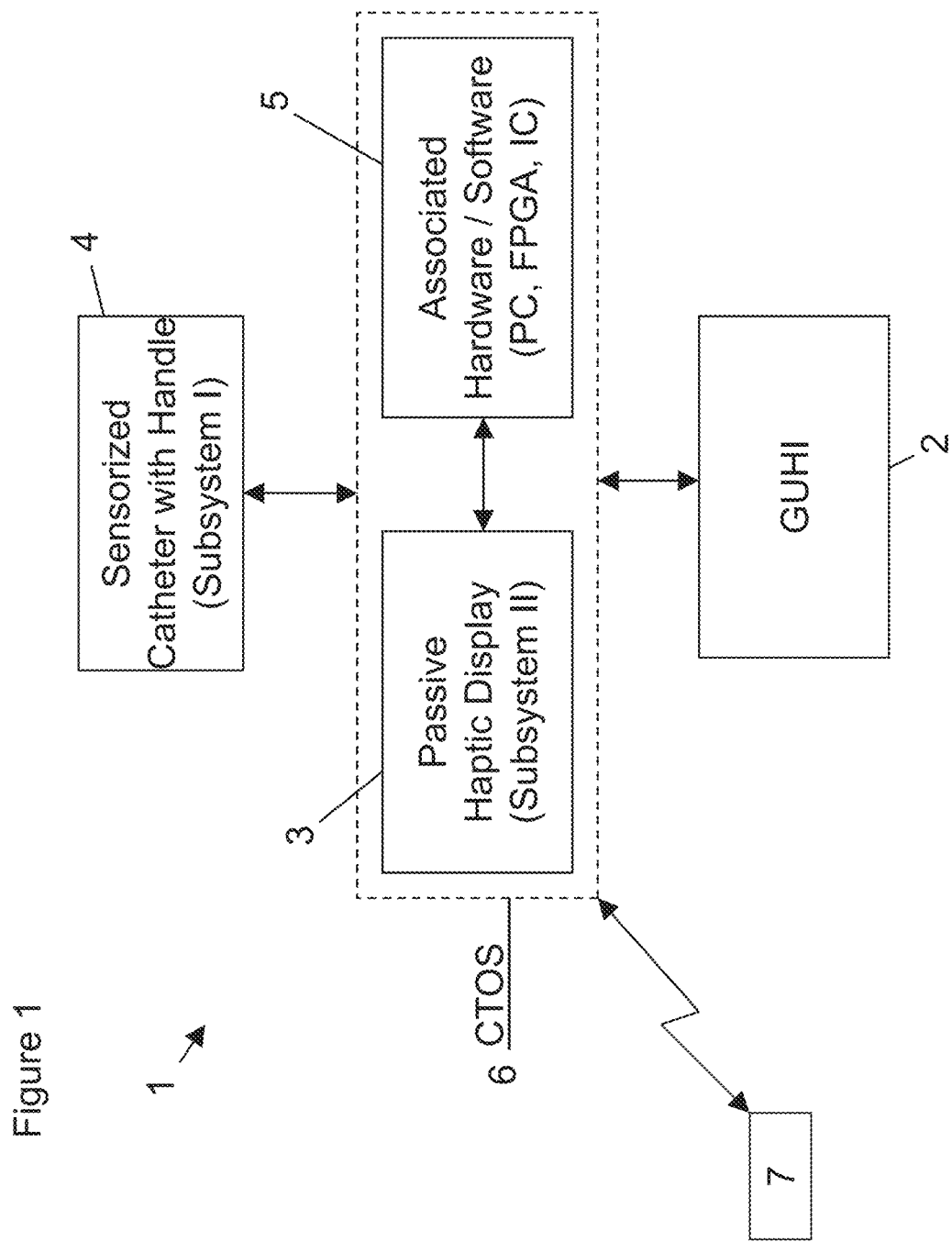
FIG. 1 depicts a schematic representation of the relation of a GUHI, and OS having a sensorized catheter coupled thereto, according to an embodiment of the invention.

As depicted in FIG. 1, one embodiment of the invention includes a vertically integrated, haptic system 1 including a graphical user haptic interface (GUHI) 2 that is an active display for controlling a user's haptic experience, one or more haptic handle interfaces 3 in the form of a hand held handle used to control a sensorized attachment 4, associated hardware 5, and an operating system 6 (OS) that together enable users to acquire, read, write, modify, store, and download sensor-acquired data in real time. The final programming changes made by any individual operator or groups of operators can be uploaded, stored, and transmitted to any other OS 7 that can also used by other users as a default haptic format.

One application for the system is for medical diagnostic and therapeutic procedures (e.g., cardiac interventions). It provides an open, universally compatible platform capable of sensing or acquiring physiological signals/data (sensor-acquired data) in any format, processing of the sensor acquired data within an operating system, and outputting of processed signals to hardware which generates tangible sensations via one or more haptic displays. These tangible sensations can be modified by the user in real time via the GUHI, while the system ensures that the temporal relationship of sensed fiducial events are not altered or shifted relative to the sensed haptic signals. Because of the variations in sensor designs and varying nature of the sensed signals (e.g. force information, motion information), different methods for processing and displaying the acquired data/signals are needed. Processing techniques and modes of display can be automatically determined based on the nature of the acquired signals, based on default settings programmed by the user (e.g., dependent on the type of procedure being performed), or modified in real time using a GUI or GUHI to suit the individual operator's preferences.

The GUHI communicates with the operator in a symbolic language and serves as a user interface that controls one or more haptic interfaces. In one embodiment, the GUHI is a touch screen interface that also provides haptic signals to the user and is thus an active display that programs haptic handle interfaces and also offers touch and or force feedback. The GUHI haptic signals confirm programming (e.g., palpable click) and provide additional sensor feedback that is descriptive of the events occurring in the haptic handle interface in real time (e.g., vibrotactile feedback, haptic rendering of physiologic events). The haptic interface preferably is in form of a hand held handle connected to an elongated member used to perform surgical procedures, which in one embodiment also generates haptic signals. The symbolic language communicated by the GUHI creates a new paradigm which provides a universal means of describing and communicating haptic signals that are based on sensor acquired data in the frequency and time domains and enables a user-friendly means for understanding, interacting with, and controlling hardware, firmware and programming software in real time.

The Operating System (OS) of various embodiments utilizes the haptic handle interfaces and can comprise one or more of, motors, actuators and haptic elements. In one embodiment, these components are located within a plug-in attachment that connects and functions with disposable, exteriorized equipment (e.g. medical instrumentation, sensorized catheter), and the associated hardware (e.g. processors/computers) as depicted in FIG. 1. The plug-in attachment is ideally hermetically sealed and isolated from having contact with the external environment thereby protecting it from inclement conditions and exposure to bodily fluids and at the same time maintaining sterility, though in one embodiment the entire unit is disposable. The plug-in attachment reflects the inner workings of the haptic handle interfaces and connects with the active haptic display or GUHI enabling the user to modify their haptic experience to suit their personal preferences without altering the data's temporal relationship with physiological and physical events (e.g. time of tissue-catheter contact, time of onset of tissue motion during the cardiac cycle). The system is designed to optimize the time delay between the presentation of clinically relevant signals (e.g., of an inserted sensorized catheter) and the time for a user to perceive and react to tangible sensations from the haptic handle. This time will depend on the mechanical characteristics of the catheter/sensor, system processing, haptic actuators, handle design and user experience. Preferably, this total time delay is less than the time of one cardiac electrical systolic time frame.

In some embodiments, modification of the haptic experience can be accomplished in real time (e.g. during procedures). This can be accomplished via the GUHI that can modify code and program software to optimize system functionality for an individual operator. In some embodiments, visual icons, and secondary notations comprise a simplified graphical format similar to that commonly seen with the notations and symbols used with musical scores. By way of example, the location of notes on a staff denote pitch (cycle length) and duration, note lengths relate to signal amplitude, double bar lines delineate time of transition (anatomical and/or physiological). For example, the GUHI would insert a double bar line when the signals input into the OS are characteristic of the catheter moving from the LAA to the pulmonary vein and the OS would drive a different set of actuators. Any type of symbol can be used including novel signs and symbols or those commonly known by those trained in music theory (e.g., tempo commands, tempo signatures, clefs). These symbols indicate specific features of the acquired signals, the action of the actuators and tangible sensations at the haptic display. The graphical format or display is augmented with haptic feedback (e.g. vibration or other palpable effect) that reflects relevant physiological information (e.g., signal amplitude, cardiac cycle dependent frequency of tissue motion).

The active programmable GUHI and haptic handle interfaces provide a means to display data acquired from one or more sensors and control the corresponding actions of one or more actuators or haptic elements within the haptic handle interface(s) which are designed to recreate the sensor acquired data. These technologies bridge the gap between sensor acquired data (sensor acquired data) and haptic display.

Graphical User Haptic Interface with Surround Sound Audio Feedback

A Graphical User Interface or GUI allows users to interact with electronic devices using images rather than text based commands. Two-dimensional display screens similar to that known in the gaming industry utilize GUIs. Graphical icons and visual indicators known as secondary notation are implemented rather than typed commands or text navigation. In some embodiments, a HUD or heads up display provides a transparent display of vital data allowing the user to see information without looking away.

In one embodiment of the present invention, the GUI can be available in the format of a HUD with a touch screen interface capable of acquiring commands from the user. In one embodiment of the invention, the touch screen provides tactile feedback and is a graphical user haptic interface (GUHI). Another mode of the invention is in the format of a transparent HUD projected or superimposed on a radio-opaque, transparent screen shield. The operator's controls, comfort and control haptic handle, catheter supply and associated hardware are readily available, stored and incorporated within a semi-circular console protecting the users from radiation exposure, obviating the need for leaded aprons and allowing for full connectivity between the operator and patient as well as full control of the operating theatre at the patient's bedside rather than using expensive telerobotic systems away from the patient and operating arena.

Audio enhancement is provided by surround sound effects that are true recreations of sensed physiological impulses, vibrations or other sensor acquired data and serve to augment the haptic feedback providing the user with multimodal sensory feedback. When the detected vibrations are within the range of human hearing (e.g. 20 Hz-20 kHz), they may not need to be adulterated. When the sensor data consists of vibrations outside of that range they can be modified, rendered or transposed into an audible range (e.g., similar to conventional Doppler echocardiography equipment). In a preferred embodiment, as an inserted catheter or instrument courses through different anatomic sites that possess different properties (e.g., vibrational frequencies, emitted sounds) the sensed shift in sensor data is communicated to the operator in both haptic and audio formats that preserve the temporal and spatial aspects of the sensed data in real time all of which can be displayed by the GUHI.

By way of example, this can be noted as a transition in palpable and audible vibratory frequency and amplitude as the sensor at the distal end of a catheter moves from the pulmonary vein where blood flow is biphasic and laminar to the LAA where there is chaotic and erratic blood flow/tissue motion. If the distal most aspect of the catheter is located at the pulmonary veins, blood flow sensors (e.g., Doppler flowire) acquire and input that data into the OS while a more proximally located sensor (e.g., strain gauge) detects LAA blood flow or tissue motion. The front aspect of the handle will display an organized laminar haptic feedback from the pulmonary vein while the rear aspect of the handle will display the more erratic signals from the LAA. Likewise, audio in the front end of the operating arena will produce sound consistent with PV blood flow while audio in the rear of the arena will be indicative of LAA blood flow or tissue motion (and the sound due to the mitral valve can be located on the left side of the operator, etc.). As the sensors are positioned with different orientations, the sound field will change and instantaneously reflect these changes simultaneously with changes in the haptic effects in a surround sound format.

The GUHI format allows for secondary notation or visual formal notation display of properties such as frequency, tone, pitch, position, velocity, acceleration sensor acquired data at the end of the sensor (or end-effector) as well as properties at the level of the audio transmitter and actuator (s) within a haptic handle interface (e.g. position, velocity, acceleration). These data can be superimposed upon any visual display including navigational and positioning systems known by those experienced in the art. This format provides syntax highlighting for programming code as will be described in more detail below. Likewise, control over the amplitude and frequency response of the audio feedback can be accomplished with the graphical user interface as well.

Sensors

In various embodiments, sensors used for gathering sensor-acquired data include electromagnetic (e.g. fiberoptic laser), magnetic, thermal, electric (e.g., intracardiac signals), ultrasonic, mechanical, deformation, compliance, piezoelectric, piezotronic, capacitive, impedance, admittance, resistive, strain, positioning/navigational system based, microfabricated and nanosensors based sensor technologies. Nor are they limited in the sense that indices that are in any way dependent on such sensor-acquired data as part of their formulation can also be implemented, in part or whole, as sensor-acquired data. By way of example, complex impedance data or other data related to catheter tip-to-tissue interface (used to derive the electrical coupling index; Ensite Navigational System, St. Jude Medical, CRMD) can be input into the operating system for processing and output of signals used to provide haptic feedback.

For example, piezoelectric force sensors that detect contact pressure along vertical and horizontal axes using oxide metal films may be utilized for the system design. In one embodiment, this design is spring-loaded where the sensor material or sensor-catheter construct is flexible and able to both dampen applied force and apply force to minimize risk of perforation and ensure contact when the applied force is inadequate to make contact, respectively. Preferably the haptic interface is likewise composed of similar or the same material and provides a real feel of the sensor-catheter construct. The haptic interface can be both actuating and/or provide haptic feedback representative of the action and reaction of the spring-loaded sensor in real time.

Other designs include a wiring structure for a tri-axial piezo-resistive force sensor placed in multiple directions to sense a contact force with respect to X and Y axes in parallel with a substrate and the Z axis perpendicular to the substrate. Other sensors may include MEMS based sensors. Further, wireless piezoelectric sensors exist which use resonant radiofrequency cavities to convert mechanical properties of attached structures into electrical signal changes. Wireless displacement sensors based on reverse design of microwave and millimeter-wave antenna arrays have recently developed for structural monitoring purposes. These types of sensors and similar sensor technology can be implemented to obtain physiologically relevant signals characteristic of tissue motion, health, pathology, anatomy etc.

In one embodiment of the GUHI, the sensor-acquired data is visibly displayed and likewise, one or more actuators designed to generate tangible sensations is visibly represented (e.g. by more than one line in a staff of a musical score). Intervals, scales, steps and the like may be representative of temporal and frequency information that is based on sensor acquired data and describes the characteristics (e.g. displacement, velocity, acceleration, vector of motion, duration of motion) of the actuators used to recreate the sensor acquired data over specified time intervals or cycle lengths. Sensor input to one or more processors is output to one or more actuators as described in more detail below.

In one embodiment, the GUHI automatically displays a graphical representation of the sensed data and actuator output and assigns which sensors' sensed data is represented by which actuator(s) without operator commands. The symbolic language is capable of providing a universal means of describing and communicating haptic signals that are based on sensor acquired data of tissue motion and blood flow properties in the frequency and time domains. Haptic effects in both the haptic handle interfaces and the GUHI can be provided by actuators, electroactive polymers, piezoelectric components, linear resonant actuators, psychophysical haptic rendering techniques, shape memory alloys, smart materials, smart fluids, simulated vibrotactile flow, active control of vibrational frequency and amplitude, or other technologies known by those experienced in the art. Methods for adapting and connecting haptic components as a subsystem to existing catheters and catheter controllers are provided for as described below.

Sensor Acquired Data

Sensor acquired data can relate to any physical, mechanical or physiological signals generated in nature that are to be communicated to the user using a haptic display (e.g. with tactile and/or force feedback). Examples include but are not limited to fluid flow, air flow, body movement, and physical or physiological properties. Sensor technology is not limited in scope or spirit and includes sensors suited for the evaluation of fluid dynamics (e.g. means of detecting blood flow, biofluidic flow, hydraulic conditions in a pre-defined apparatus, water flow in nature) and non-contact sensors that use electric (e.g. impedance, resistive, capacitive), electromagnetic, magnetic, ultrasonic or alternate technologies that can acquire the needed data in the absence of contact and even be implemented with robotic systems such as robotic magnetic navigational systems that could benefit most from tactile feedback. Sensor acquired properties in this regard include but are not limited to indices of laminarity, turbulence, velocity, flow, inertia, pressure etc. Examples of physiological properties include tissue motion (e.g. cardiac tissue motion, motion of muscles of respiration such as the diaphragm), intravascular blood flow and changes in blood pressure as different vessels or cardiac chambers are entered and tissue planes traversed (e.g., transeptal puncture). Pressure recordings can be made with more than one transducer or manometer, such as end-hole and side-hole manometers along the distal aspect of an inserted guiding catheter. In one embodiment, each pressure transducer generates signals that are processed in the OS and output to separate actuators at the haptic interface (e.g., different motors within a haptic handle housing). This will provide a blend of haptic effects that change as the anatomic location of each pressure transducer changes (e.g., from right to left atrium during transeptal puncture) and provide both temporal and spatial information in a haptic format. This can be performed with any sensor modality and provide similar feedback to the operator. By way of example, flow sensors can be used to detect an ablation catheter's proximity to the LAA and left upper pulmonary vein, or a stent deployment apparatus can provide blood flow information on both sides of a stenosis, or a hemodynamic index such as fractional flow reserve. Preferably, differential haptic effects representative of the gradient in sensed indices (e.g., blood flow velocity, laminarity, amplitude, frequency) are provided by two or more actuators along the length of the haptic interface.

Graphical User Haptic Interface—GUHI

In one application of the GUHI, the interface provides the operator with information about sensed data acquired from one or more sensors that sense anatomic and physiologic properties of cardiac tissue and blood. For example, these sensors acquire information about force, pressure, velocity, flow, acceleration and displacement, torsion, strain, texture, deformation, strain rate, anatomy. The sensors can be positioned within the heart (e.g., contact sensors on the distal aspect of inserted catheters or instruments) and/or outside the heart (e.g., non-contact sensors, radiographic, ultrasonic, electromagnetic, electric (e.g., impedance)) or inside the heart, within the vasculature or other anatomic structure/cavity with or without contacting tissue (e.g., intravascular ultrasound). Such data represent indices (e.g., of cardiac function) in both frequency and time domains and also define the effect of and interaction between inserted instrumentation and anatomic tissue on such indices. This data is then processed and either stored for diagnostic purposes and/or displayed for the user (e.g., visibly, haptically, audibly). One type of display that can be implemented is a haptic display that is used to communicate the sensor-acquired data to the operator in real time during diagnostic (e.g. angiography) and therapeutic procedures (e.g. coronary interventions, tissue ablation, percutaneous valve replacement/repair). Other types of displays such as audio and visual displays (multimodal) can be implemented as well.

Figure 2:
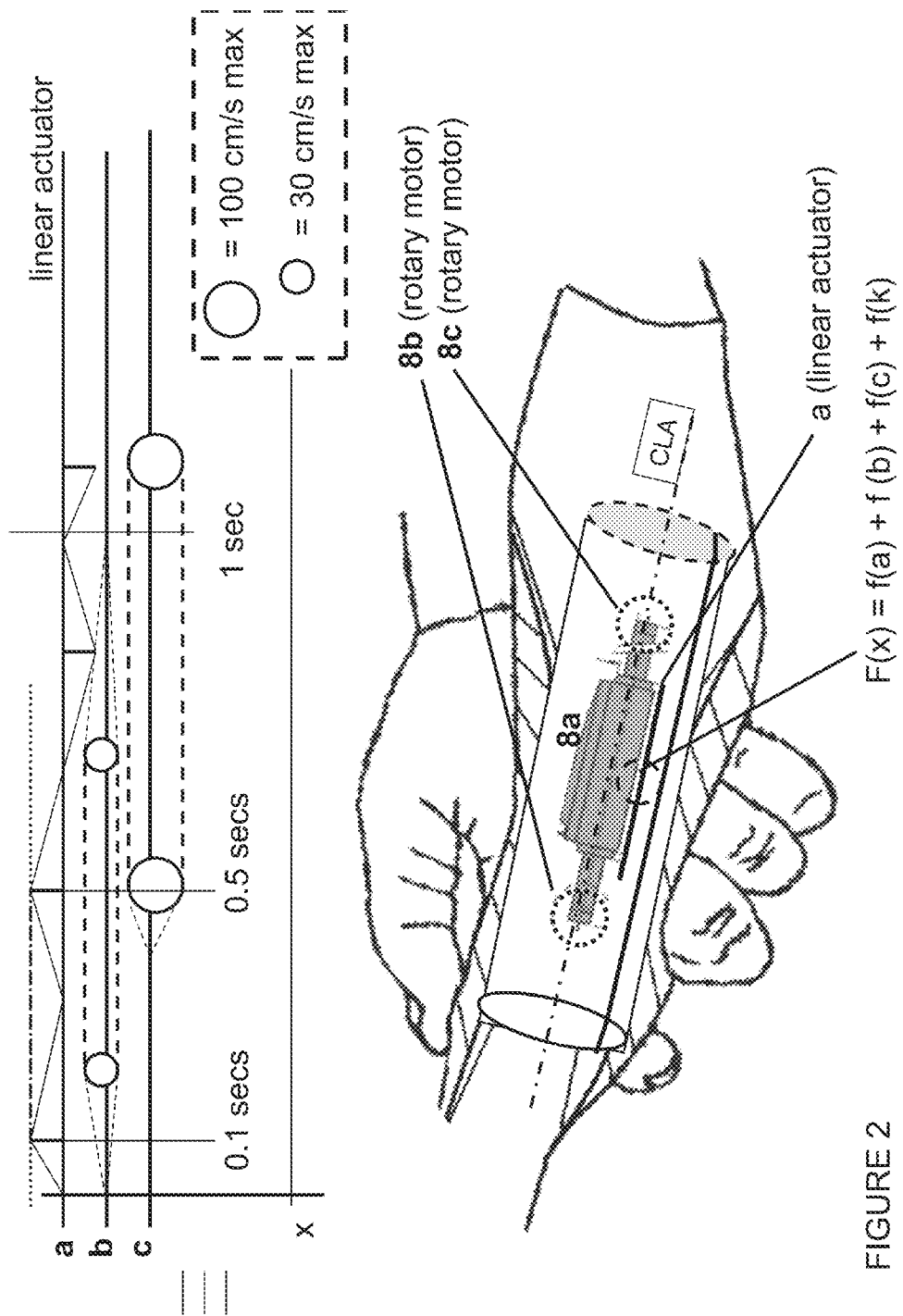
FIGS. 2 and 3a depict a combined view of an exemplary catheter handle and a representative display of haptic feedback therefrom, according to an embodiment of the invention.

An example of how the GUHI functions, in the context of this application, is provided in FIG. 2. Though the symbols and notations used in these examples can be implemented in the final form of the GUHI, other means of displaying the data and providing an interface to the user are within the scope and spirit of the invention and those detailed herein are presented to allow the reader to fully grasp the utility and workings of the GUHI.

Referring to the bottom of FIG. 2, a linear motor $8a$ (or motor "a"), a rotary motor $8b$ (or motor "b"), and a rotary motor $8c$ (or motor "c") are disclosed. At the top of FIG. 2, the ordinate represents displacement distance for linear motor $8a$, rotational velocity for motor $8b$ and/or motor $8c$. The abscissa represents time. The linear DC brushless servomotor, $8a$, moves fully forward (line a with symbol 100% above line at 0.1 seconds). Its acceleration (and velocity) is dictated by the time it takes to reach full displacement from baseline and time zero (e.g. 10 mm at 0.1 secs). The value of displacement is based on the properties of the motor which in this case=10 mm maximal in forward and reverse directions. Rotary motor $8b$ initiates rotation at time zero and reaches maximal rotational velocity at time 0.25 seconds. Thus, there is angular acceleration between time zero and 0.25 seconds at which time it reaches a constant velocity and acceleration=zero. The motor then decelerates to a complete stop at 0.9 secs. Rotary motor $8c$ begins rotation at time 0.4 seconds, accelerates until it reaches and maintains a constant velocity at 0.5 through 1.2 seconds and then stops virtually instantaneously. Rotary motor $8b$ rotates at a lower maximal velocity (30 cm/s) than rotary motor $8c$, which is symbolized by the smaller radius of the circle. Pivot point X is located at the center of gravity of the linear motor. It has an adjustable coefficient of friction, which can be mechanically or electrically modified. Thus, the linear motor rests upon a shelf that can rotate and is mounted with pivot point mount x on the inner casing of a handle. The shelf has a limited range of motion (e.g. +/−20 degrees) and provides additional haptic feedback to a user holding the handle as the combined motion of the other actuators cause the shelf to rotate. The rotational position of the linear motor $8a$ is a function of this coefficient of friction k and the properties of motors $8a$-$c$. Thus, in this embodiment it is not programmable, but is dependent on $8a$, $8b$, $8c$, and $k$.

Figure 3A:
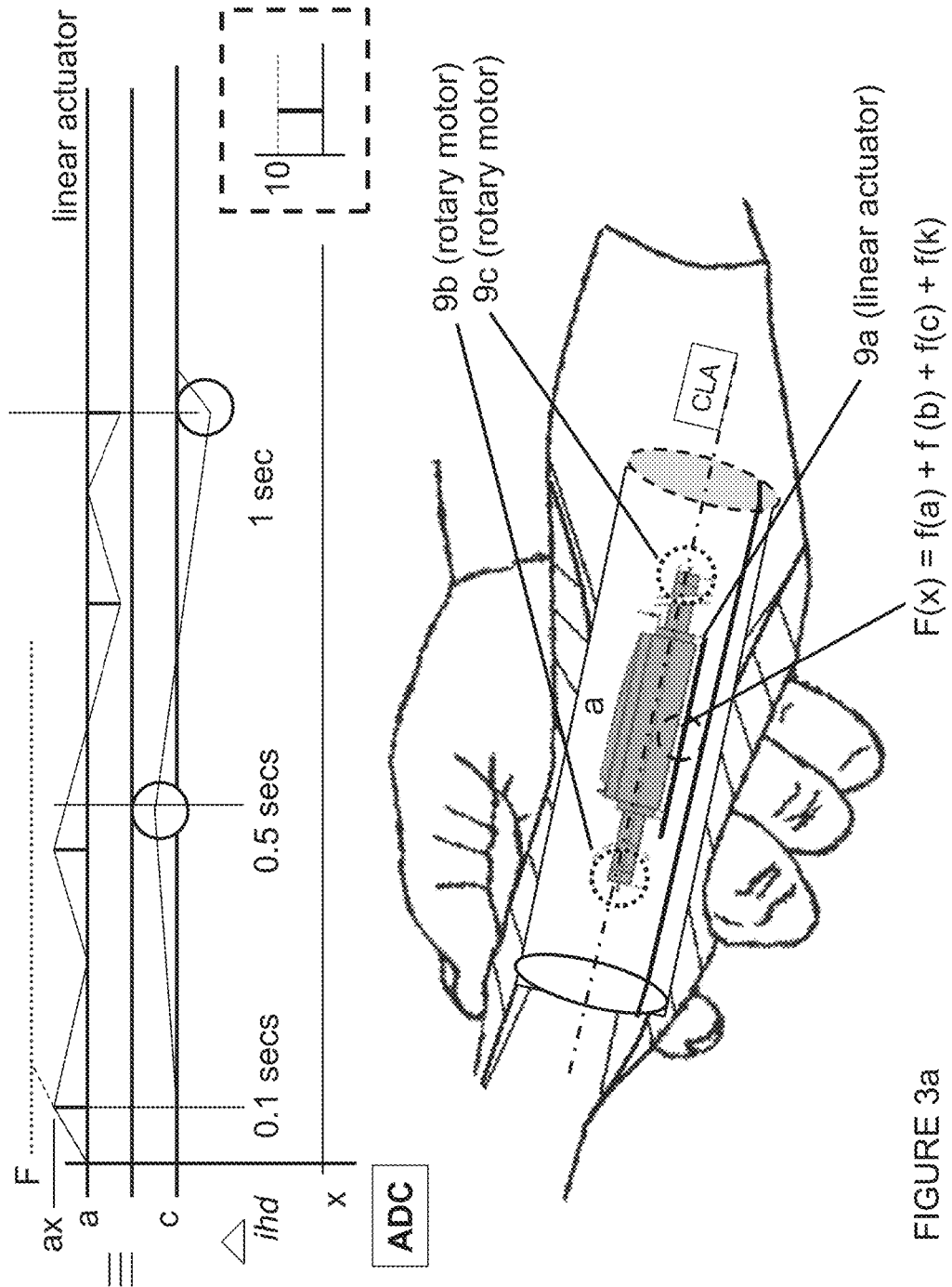

Another example of a GUHI is provided in FIG. 3a. Linear motor $9a$ moves forward to position $a_x$ at 0.1 seconds. At this velocity it would have reached a fully forward position F (10 mm-top dotted line) at 0.15 seconds. Thus, its position at 0.1 seconds is forward at $0.1/0.15 \times F$, where F=10 mm.

Rotary motor $9b$ is in a fixed position and serves as a counter weight for motor $9c$ which is the same weight and size (density) and is not represented in the GUHI.

Rotary motor $9c$ begins to move in a clockwise rotation (above line) at time 0.1 secs, reaching its peak velocity at 0.5 secs. It then rotates in a counter-clockwise rotation (negative slope of line) up until 1 second where it reaches its peak counterclockwise velocity and then abruptly rotates back to its starting rotational position at just after 1 second.

Each motor icon is representative of sensed data from one or more sensors (sensor acquired data). The input to each actuator can be determined simply by assigning each actuator to an individual sensor as a default setting or having characteristic sensed signals from one or more sensor(s) "innervate" an individual motor based on frequency spectrum, temporal characteristics, sensor locations and operator preference, etc. By way of example, force sensors have data processed using admittance haptic interfaces and presented as motion information using a specified DC linear servomotor housed within a hand held haptic handle (e.g., sensed force proportionate to motor displacement). The degree of motor displacement is palpable as a tangible sensation in the hand held handle and directly relates to the sensed forces between inserted instrumentation and contacted tissue. The ratio of sensed force to linear displacement (or velocity, acceleration) can be adjusted by the operator using the GUHI. Mathematical algorithms can be programmed (e.g., via changes in software/code) to create haptic feedback suitable for a given user. By way of example, an index that is a function of one or more physical events (e.g., absolute force, first or second differential of force waveform data, etc.) can be used to drive haptic actuators in part or in whole.

Simple band pass filtering can determine which signals of a specific frequency range are directed to a specific actuator (s), or more complex data acquisition and processing techniques may be used to drive one or more haptic actuators. This data assignment can be displayed for the operator to evaluate using a graphical interface. Signals characteristic of specific events (e.g. vibratory signature representative of initial catheter tissue contact) are represented at the most appropriate actuator (e.g. haptic elements situated upon the catheter proper, in closest proximity to the patient's body surface). This is discussed in more detail below.

Thus, the user's palpable sensation (and actuator's action) can be a reflection of the baseline signal (e.g., real time force at the tissue-catheter interface) multiplied (or divided, etc.) by another factor (or constant) such as the change in force over a specified time frame (first-order derivative at a pre-specified time or based on a value of a sensed parameter (e.g., acceleration, peak derivative of force as a function of time)). Constants or other mathematical functions can be introduced to alter the relative contribution of any specific parameter (force or otherwise) to the final haptic effect.

In one embodiment, the visual icons are on a touch screen and provide haptic effects to the user that are representative of sensed events and the tangible sensations occurring at the haptic handle interface.

Figure 3B:
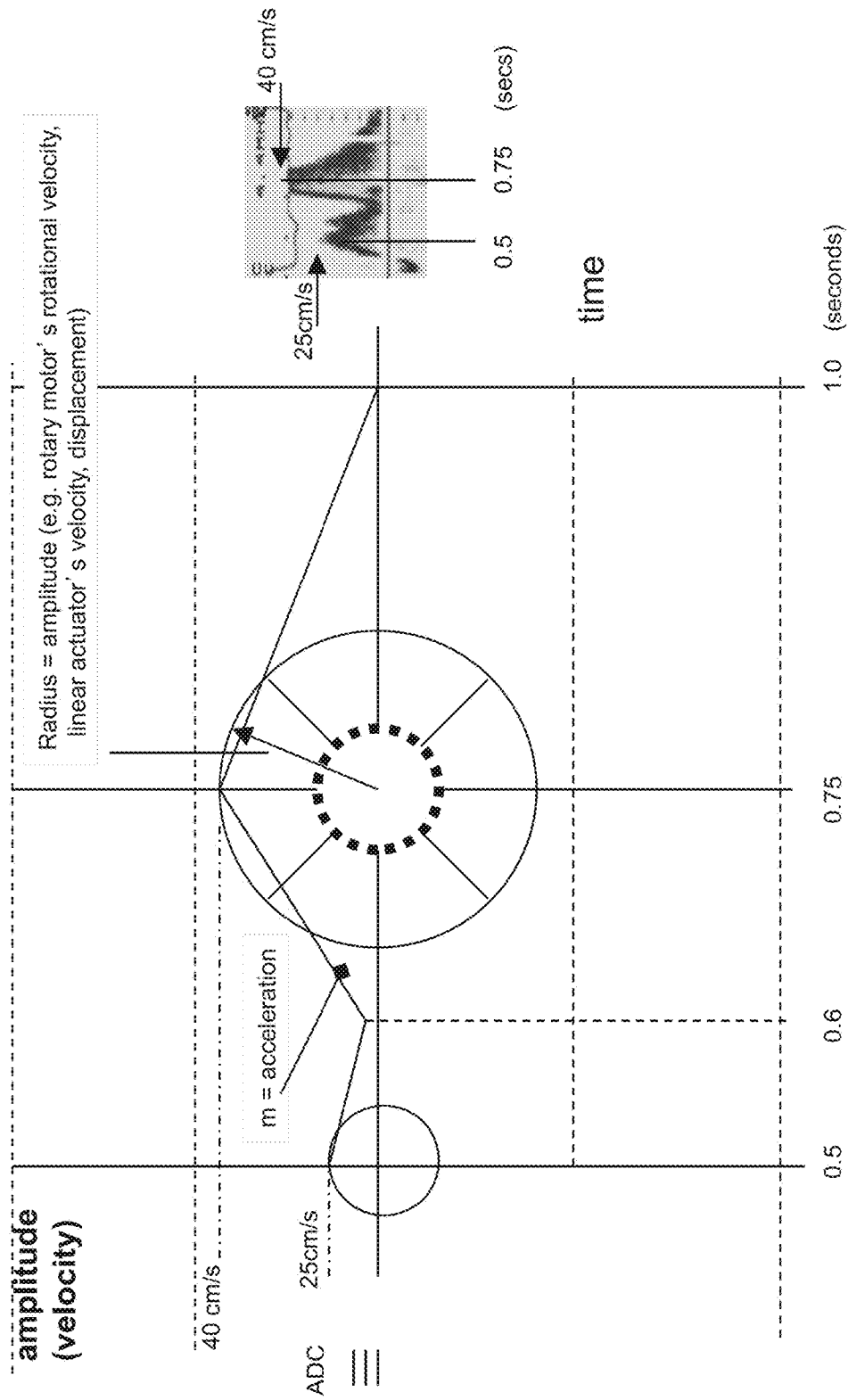
FIG. 3b illustrates how a graphical user interface with haptic features conveys (GUHI) physiological relevant signals, amplitude and frequency information about tissue and blood flow properties.

In one embodiment of the GUHI, a circle serves as a visual representation of sensed physical events of specific regions of cardiac tissue (e.g. left ventricular myocardial displacement, left atrial appendage tissue velocity, velocity of blood flow) and conveys information about the frequency and amplitude of tissue motion as depicted in FIG. 3b. For example, the radius of the circular icon represents the amplitude of the sensed event (pulmonary venous blood flow velocity) at a specific time.

If you touch the circle and rotate your finger about the perimeter of the circle clockwise you will increase the radius of the visual icon, increase the amplitude of the haptic motor's displacement (or velocity, etc.) relative to the sensed event, thereby controlling the amplitude of the tangible sensations indicative of specific sensed physical events. If you rotate your finger counter clockwise you will decrease the ratio between the amplitude of the haptic sensation and the amplitude of the sensed events. You cannot change where the circular icon (secondary notation) is along the abscissa as you can not modify the timing of the peak amplitude of such an event.

The amplitude of the sensed event may vary depending on where the sensor is located (near or far away from the left atrial appendage) or how much force is applied (degree of contact between tissue and sensorized catheter) but preferably the frequency characteristics of the sensed cardiac tissue motion will not change (left atrial appendage fibrillatory motion, pulmonary venous blood flow), nor will its location along the abscissa (in this eg. peak velocity at time 0.5 seconds).

In this example, the cycle length of the circle's rotation would be equivalent to the (variable) cycle length of the LAA's contraction. Its radius would be equivalent to the velocity of the LAA tissue motion (cm/sec) and scaled accordingly. The slope of line m is acceleration if the radius of the circle is velocity (or velocity if the radius is displacement).

The user can touch the circle and reduce the amplitude of the haptic effect in the handle by rotating it counter clockwise. Each interval decrease (e.g. ⅛th) would lead to a palpable click (tactile feedback) and an audible click and a visual decrease in the radius of the circle (multimodal haptic feedback). The scalar range of the ordinate would change in range or scale accordingly as this represents the actual or true value of the sensed tissue velocity (e.g., 40 cm/s), while the radius of the circular icon represents the palpable tangible sensation being adjusted by the operator. Different icons or secondary notations would represent different haptic actuators and correspond to different sensed events (tissue displacement, velocity, blood flow, velocity) and those used as examples herein are purely exemplary.

If the sensed signals are recreated at the haptic interface (e.g., handle) an equivalent sign is seen. If there is "significant" modification of the sensed event (haptic rendering) then a delta sign is seen. If the sensed signal is force (e.g. Enclosense or BioSense Webster Smarttouch force sensor) and the degree of force is proportionate to the amount of displacement of a linear motor (e.g. in millimeters), a delta sign would be visible. The latter type of haptic rendering can relate to use of an admittance haptic interface or display (AHD) in the Operating System. The input is force and the output is an index of motion such as velocity (or its first integral, displacement, in this example). An impedance haptic display would sense tissue velocity and output force (e.g. of a haptic element striking the palm).

If an analog signal is sensed and maintained as an analog signal out, an AA is seen and if AD conversion occurs an ADC is seen (in this example). No haptic rendering occurs in this example and thus an equivalent sign is seen (under ADC in FIG. 3b).

By way or example, referring to FIG. 3b, at time 0.5 seconds, peak blood flow velocity equals 25 cm/sec. At 0.75 seconds there is a higher peak in the sensed velocity of pulmonary venous blood flow (e.g. 40 cm/sec), which then decreases to a zero value at t=1 second. This is palpable in the handle. For example, between 0.5 seconds and 0.6 seconds, the blood flow velocity decreases and the corresponding rotary (or linear) motor decelerates from 25 cm/s to a nadir at 0.6 seconds. Then as blood flow accelerates, the motor likewise increases in velocity, until it is moving at 40 cm/sec at time 0.75 seconds and then decreases to a standstill at time=1 second. These time dependent changes (i.e., during one cardiac cycle) in blood flow velocity are also represented in the insert image of pulmonary venous blood flow as detected by Doppler ultrasound on the right side of FIG. 3b where there is an initial peak velocity of 25 cm/sec and secondary peak in velocity of 40 cm/sec at the same time frames.

Some users may desire a subtle haptic effect and others may desire a more pronounced effect. They can modify their haptic experience by touching the circle on a touch screen and rotating it like a volume knob. In one embodiment, a vibratory signal is present on the touch screen that is indicative of a physical parameter such as tissue velocity. Higher frequency vibration represents higher frequency tactile feedback (haptic rendering). The touch screen is interactive, allows programming of certain parameters and provides haptic feedback as well, but never changes the timing of fiducial events. The operating system maintains this temporal relationship even if there are changes in the amplitude of the tangible sensations relative to the sensed events.

Processing

In various embodiments, Operating System (OS) supports haptic recreation of sensed data is shown in FIG. 2 with an equivalent sign on the left side of the score. When haptic rendering techniques that do not provide recreations of true sensed physical properties are used in the haptic display this is represented by having a delta sign on the left side of the score. If both haptic recreation and rendering are applied, both symbols are used. As an example, the sensor-acquired data is a measurement of force or pressure. An admittance type haptic display (and) can be implemented and the measured force is displayed as linear velocity at the level of linear motor 8a. An example of a symbol used for this type of processing is a delta sign with subscript ahd. Likewise, the sensor acquired data can be a measurement of velocity or displacement and an impedance type haptic display (e.g. force feedback) is used and the notation would be a delta sign with subscript ihd. As the sensor acquired data and displayed data are maintained as proportionate and are linearly correlated, an equivalent sign is used as well and this is shown in FIG. 3a. Alternatively, the measurement of pressure can be made with conventional fluid filled catheters/manometry and not require additional sensors. This would be particularly advantageous during procedures such as transeptal puncture and in this example the symbol would simply be a value of pressure or pressure time curve display superimposed on the graphical user interface as illustrated in FIG. 3C. RA is pressure during multiple cardiac cycles when a distally located pressure sensor at the end of an inserted catheter is within the right atrium, BP reflects blunted pressure when the distal portion of the catheter (or bore tipped needle) contacts the interatrial septum and LA reflects left atrial pressure in real time. Actuators in the handle provide a qualitatively and quantitatively similar tangible sensation to the user when the catheter transitions from one anatomic location to another. The OS and GUHI enable any sensor type to be used and integrated into the system by providing the appropriate signal processing (e.g., signal conditioning, haptic rendering) and allowing both automatic and manual programming that is adaptive on the fly as one or more types of sensors are used to acquire data as input into the haptic system.

By way of example, during a single procedure, a guiding catheter used for transeptal puncture can acquire blood pressure data (FIG. 3C) and then the system can switch to using force data (FIG. 3D) that tactually confirms tissue contact during delivery of radiofrequency energy about the pulmonary veins for atrial fibrillation ablation procedures. Both force and pressure data are displayed by the haptic interface (e.g., haptic handle). In various embodiments, the operating system may function with any contact or non-contact sensor type and sensors may include those using ultrasound, impedance, and magnetic, electromagnetic, radiographic, navigational systems as some examples. The OS can define the type of sensor(s) being used based on the nature of the signal(s) input into the OS. Alternatively, and additionally, the OS can define the type of sensor being used and adjust system function (e.g., signal processing and delivery of output signals to the respective actuators) based on the nature of the signal and/or anatomic location of the treating member of the inserted catheter/instrumentation as defined by signal properties or information obtained from non-contact sensors (e.g., navigational systems). For example, pressure waveforms differ from force waveforms and the type of signals input into the OS may vary (e.g., voltage, current) depending on the type of sensor employed.

In one embodiment, real-time sensed force (FIG. 3D) can be displayed at the GUHI and/or generated at the haptic handle interface as force and/or motion data (e.g. velocity, acceleration, displacement). Force and pressure can be displayed using piezoactuators, as described below, that provide force feedback to the palm of the user via a hand held haptic interface (haptic handle). Low frequency motion data can be displayed using linear servomotors with haptic elements that impart tangible sensations to the user and high frequency motion data with rotary motors with offset weights that cause vibrotactile feedback. In another embodiment sensed motion (velocity, displacement, acceleration) is displayed the GUHI and/or generated at the haptic handle interface as force and/or motion data. In still yet another embodiment, sensed strain is displayed at the GUHI and/or generated at the haptic handle interface as motion, strain, pressure, and/or force. Any type of sensor acquired data can be displayed as the same (e.g. force as force), or as physically different data (e.g. force as velocity, etc) in form of tangible sensations as will be described in more detail below.

Digital signal processing (DSP) techniques that are applied are likewise represented by specific signals. When analog digital conversion is utilized an ADC is visible on the GUHI (FIG. 3a). The GUHI can also have haptic features, such that when a specific icon or graphical symbol is touched on a touch sensitive screen one or more tangible sensations with gradients in intensity can be generated to confirm that the symbol is being interacted with (e.g. using an electroactive polymer, LRA, piezoactuators) and that an action or programming change has occurred. By way of example, the user can touch a Boolean icon that can modify the haptic experience to be purely analog, digital (ADC in FIG. 3a), or a combination of both and a palpable click is appreciated when the icon is touched.

The user in these examples can touch an icon on the GUHI and then modify the settings. For example, the maximal displacement, velocity, rotation can be limited to specific values and type of signal processing being used denoted. The amplitude and/or frequency of the haptic effect from the GUHI are proportionate to the programmed setting and/or sensor-acquired data. Once an icon is activated a meter can appear on the right side of the screen with specific programmable values indicated (box with dashed lines in FIGS. 2 and 3). Any type of microprocessor can be programmed using the GUHI including but not limited to conventional microprocessors, integrated circuitry and field programmable gate arrays. Communication of data can be via any means including but not limited to Ethernet, USB, fiberoptic, wireless or Bluetooth telemetry.

The GUHI system, in one embodiment, is a vertically integrated system where one or more hardware and software subsystems are designed to function in unison and are physically connected to one another, though wireless communication is within the scope and spirit of the invention. Modifications in hardware and software do not interfere with functionality and provide for easy upgrades in either or both subsystems as they are detachable.

Figure 5:
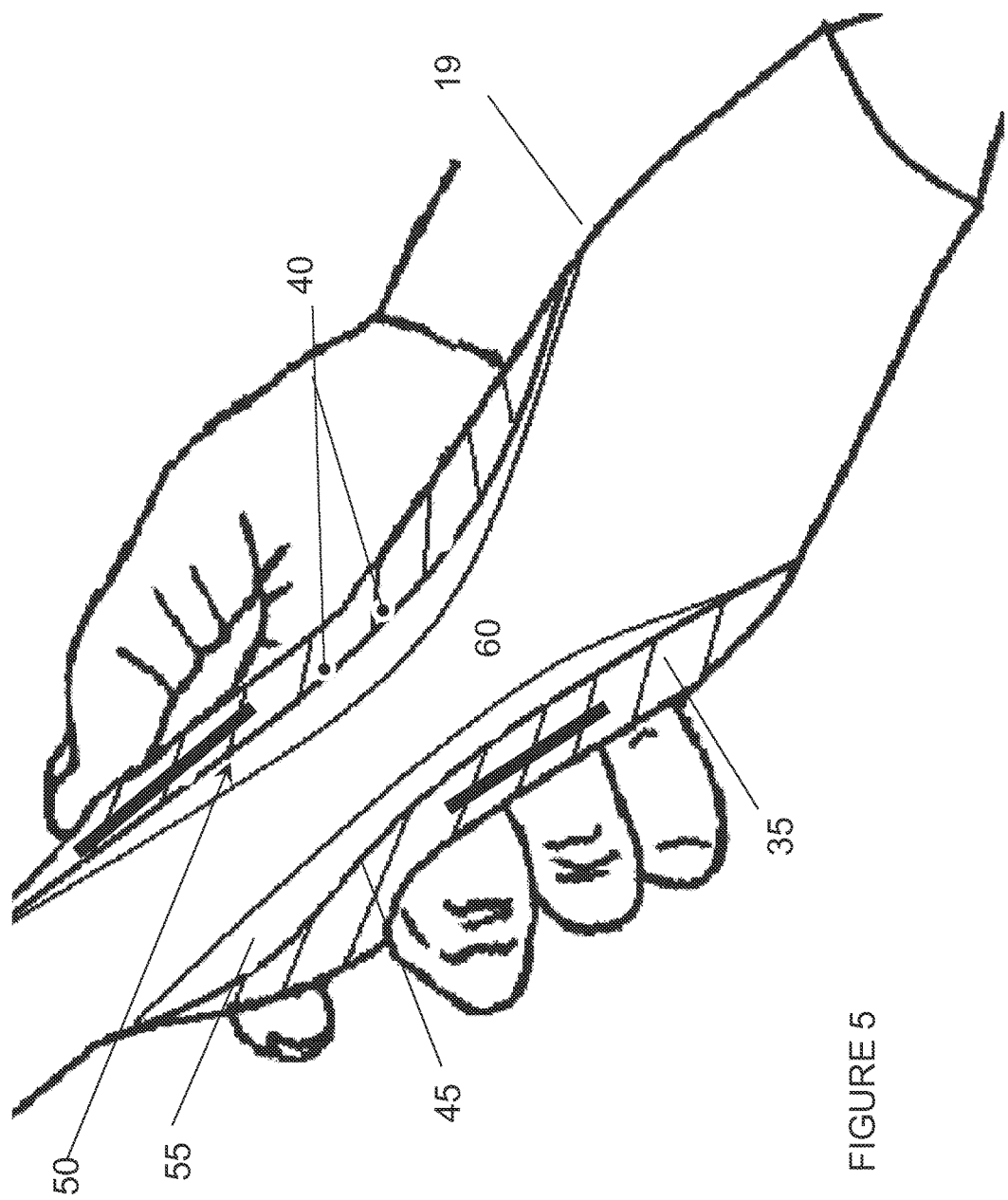
FIG. 5 is an enlarged view of a haptic feedback-enabled medical device handle that is deformable to provide additional comfort and control for the operator, according to an embodiment of the invention.
Figure 13:
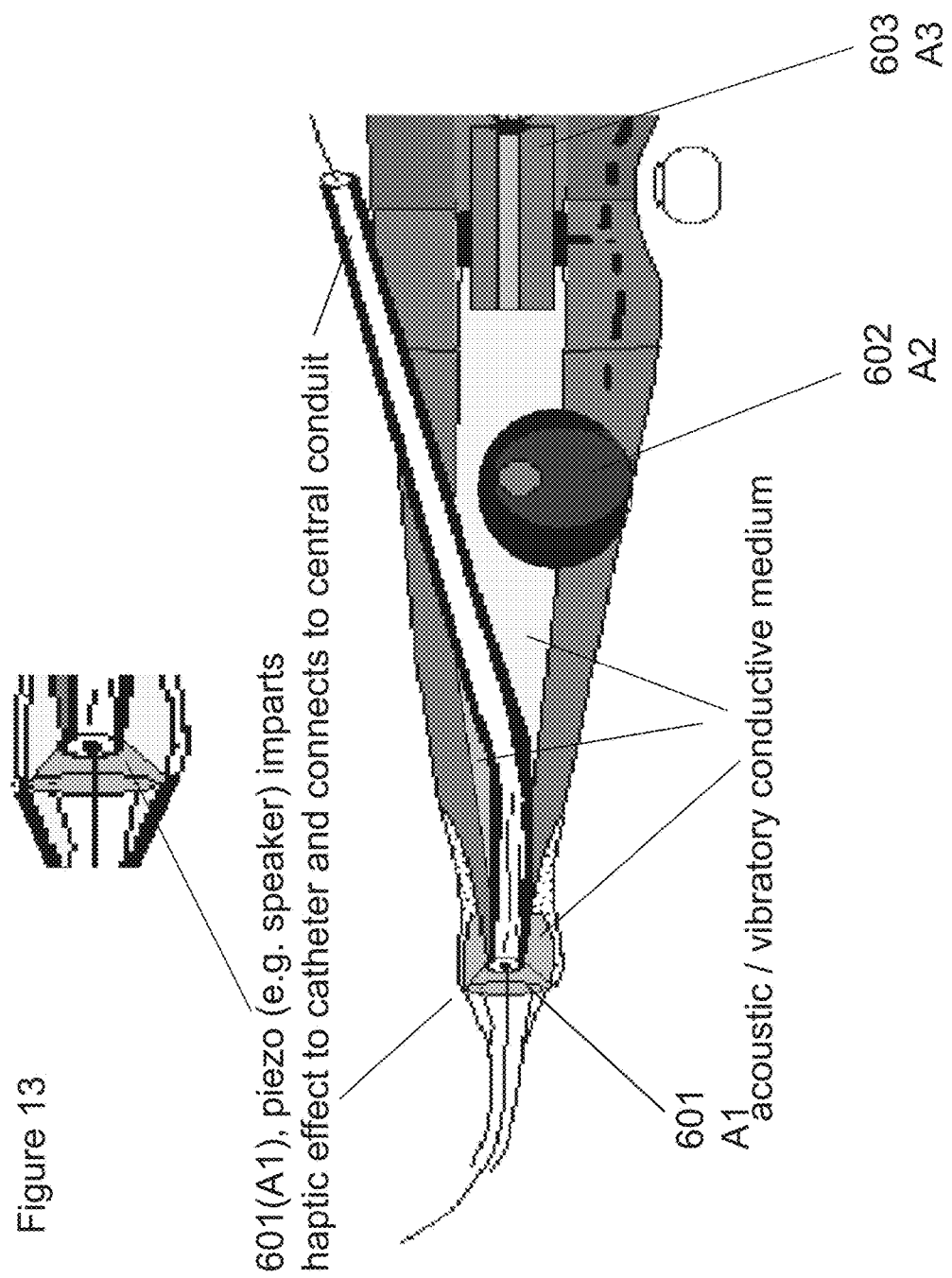
FIG. 13 presents a view of an end effector that can couple to an exemplary haptic-enabled handle, according to an embodiment of the invention.

An example of a GUHI Subsystem is shown in FIG. 4 and consists of a medical instrument such as a cardiac outer catheter 17 and sensor 16 that interconnects with a handle 15 composed of a disposable outer shell 19, as depicted in FIGS. 4 and 5. Components—15, 16 and 17 comprise subsystem I. The outer shell 19 is a rigid or semi-rigid material such as urethane or urethane composite that provides a scaffold support for the inner hardware (Subsystem II). The handle can be outfitted with a deflection mechanism 20, as known by those experienced in the art such as a collar that controls the shape of the sensorized catheter. In some embodiments, the handle 15 incorporates an inner conduit 25 that can house and guide placement of additional instrumentation 30 which can include but is not limited to wires, inner catheters, medication delivery systems, energy delivery systems, guide wires, stents, sensors and the like for positioning and introduction into a given anatomic location (e.g. coronary artery). In another embodiment, the haptic handle is constructed to provide haptic feedback and glide or be positioned along the body of an inserted catheter that is part of a completely separate apparatus, such as an ablation catheter. In this embodiment the operator might hold the haptic handle in his or her left hand and the ablation catheter handle in their right hand and the ablation catheter courses through a central or inner conduit within the haptic handle as illustrated in FIGS. 4 and 13.

Inner conduit 25 can be used as a means for attaching components without haptic technology to a handle which imparts tangible sensations created within the handle to any components or parts such as a catheter, wire, etc that course through the inner conduit, thereby extending the haptic display to include such attached components in addition to the hand held handle portion. In this fashion, haptic effects are displayed in multiple locations (e.g. hand held catheter in the left hand and hand held handle in the right hand).

Similarly, a miniaturized, microfabricated or nanotechnologically based haptic system 20h can be implemented as part of the hand held portion of any catheter (e.g. coronary sinus guide catheter) as shown in FIG. 4a. System 20h can also serve to deform, deflect or control one or more portions of such a catheter and functions as both an actuator and haptic display. In FIG. 4a, it is integrated into the spring based mechanism that enables placement of an inner catheter within an outer catheter by controlling the opening of a diaphragm to prevents backbleeding and secures the inner and outer catheter together. In one embodiment, 20h is a spring-loaded piezoactuator that provides haptic feedback and mechanical control of two interlocking catheters. Sensor 16 can provide the sensor-acquired data that assists the operator during manipulation and positioning of catheter 17 for diagnostics and therapeutic interventions.

Referring to FIG. 5 is a longitudinal cross section of the comfort control haptic handle 15 that is designed to be comfortable to hold. Conventional handles as understood by those experienced in the art often have gripping portions that impart flexibility and cushioning properties for comfort purposes similar to that disclosed by Schultz et al in U.S. Pat. No. 7,770,262, the disclosure of which is hereby incorporated by reference except for any definitions or claims. In some embodiments, handle 15 preferably has interchangeable inlays that consist of thermal plastic elastomer grips 35, ductile composite polymer structures or other medium (e.g. acoustically conductive), which effectively transmits and/or produces tangible sensations as a result of the motion of haptic elements contained inside the handle within subsystem II (described below) or haptic elements positioned within and/or underneath grips 35 (e.g. bender piezoactuators, patch transducers constructed of piezoceramic foils between conductive films (black rectangles in FIG. 5)) or from 35 itself. Windowed defects 40 in the scaffold support 45 can be used to reduce attenuation from motion related to the inner haptic elements rather than to minimize vibration as conventionally understood. These defects can be fabricated using elastic, pliable thin elastomer that may range between 0.5 and 5 mm in thickness or be devoid of any material. In one embodiment of the invention, a viscoelastic or liquid substance 50 (arrow) is sealed and contained within one or more cavities 55 that extend along the inner circumference of handle 15. This substance can be multi-purpose and either attenuate the inner haptic signals, serve to evenly distribute or focus the signals, or provide additional haptic feedback. Substance 50 can be composed of an inactive substance or active smart material or fluid such as electrorheologic or magnetorheologic fluid. Variable current or magnetic fields can be applied by the user to modify the properties of substance 50 enhancing the user's individual haptic experience. Alternatively or additionally, the user's hand can be encompassed by the smart fluid/material or be within a haptic glove and tangible sensations are provided about the entire hand or even the user's arm.

A subsystem comprised of the mechanics and electronics needed to impart the desired haptic effect can be integrated with other catheter based systems including the hand held portion of conventional catheters such as outer, inner, and guiding catheters and more sophisticated technologies for controlling catheters for diagnostic and therapeutic procedures (e.g., robotic based ablation technologies, deflectable catheter systems). The integration can be accomplished by physical contact with an inner or outer section, shell, inserted components or any other attachment. In the example detailed herein, an inner tube houses all the needed components for creating the desired haptic effects.

Any motors within this embodiment, as described in detail below, may interact with substance 50, via electromagnetic interaction. By way of example, linear motors that have ferrous properties or are ferromagnetic can affect the physical and haptic properties of substance 50 secondary to generated magnetic flux effects. Such haptic effects in subsystem I can be controlled in part or wholly based on analysis of sensor acquired data and be represented in the GUHI. Alternatively, such haptic effects are separately controlled by the operator, for example, as to control the intensity of the haptic effect (attenuate signal amplitudes). Such a simple control can be represented in the GUHI as a Boolean symbol or meter indicating if such an intensity control is on or off and what the value (of attenuation) of the affect is within a pre-specified range.

In an alternate embodiment, the surface outer shell 19 is in part or whole constructed of a haptic interface rather than a rigid supporting structure. The interface can consist of one or more haptic technologies as known by those experienced in the art. This includes but is not limited to actuators that function using traveling wave vibrotactile actuators, circular or linear resonators, haptic surfaces, piezoactuators, actuators that propagate lamb waves, and the like. This surface haptic interface can function via psychophysical haptic rendering and recreate physiological data simulating real time biomechanical events as if the haptic surface were actual cardiac tissue or fluid or convey temperature and texture information. In one mode, the surface haptic interface simulates conditions and renders the user's hand or other anatomic structures (e.g., wrist, arm) to feel like an actual inserted instrument and/or actual biological tissue. Visual and auditory inputs (multimodal feedback) can be provided to augment haptic feedback (e.g., three dimensional visual feedback, surround sound formats).

In still yet another embodiment, the haptic handle interface is shaped with hourglass contours with an elastic membrane or other deformable material that contacts the palm and transmits tangible sensations from underlying haptic elements/linear actuators, piezoactuators. Such a construct prevents the operator from exerting too much force upon the actuators and limits the affect of the operator on the motion of the haptic elements. By way of example, more rigid scaffold support is provided where the carpal-metacarpal junction lies and at the level of the intermediate phalanges thereby preventing compression of the underlying membrane and haptic components.

Figure 6:
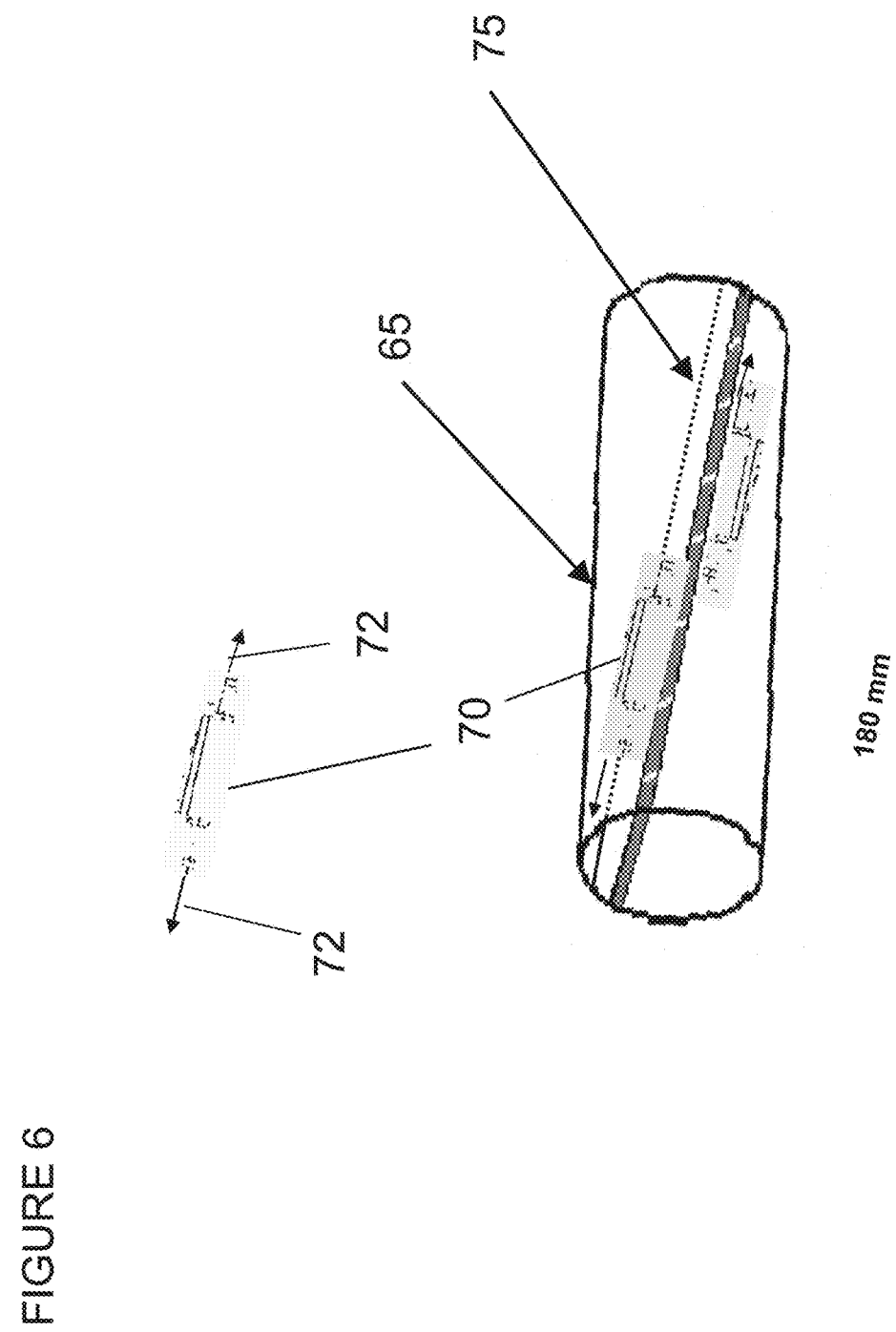
FIG. 6 illustrates the motion of a longitudinal actuator within a haptic-handle according to an exemplary embodiment, according to an embodiment of the invention.
Figure 7:
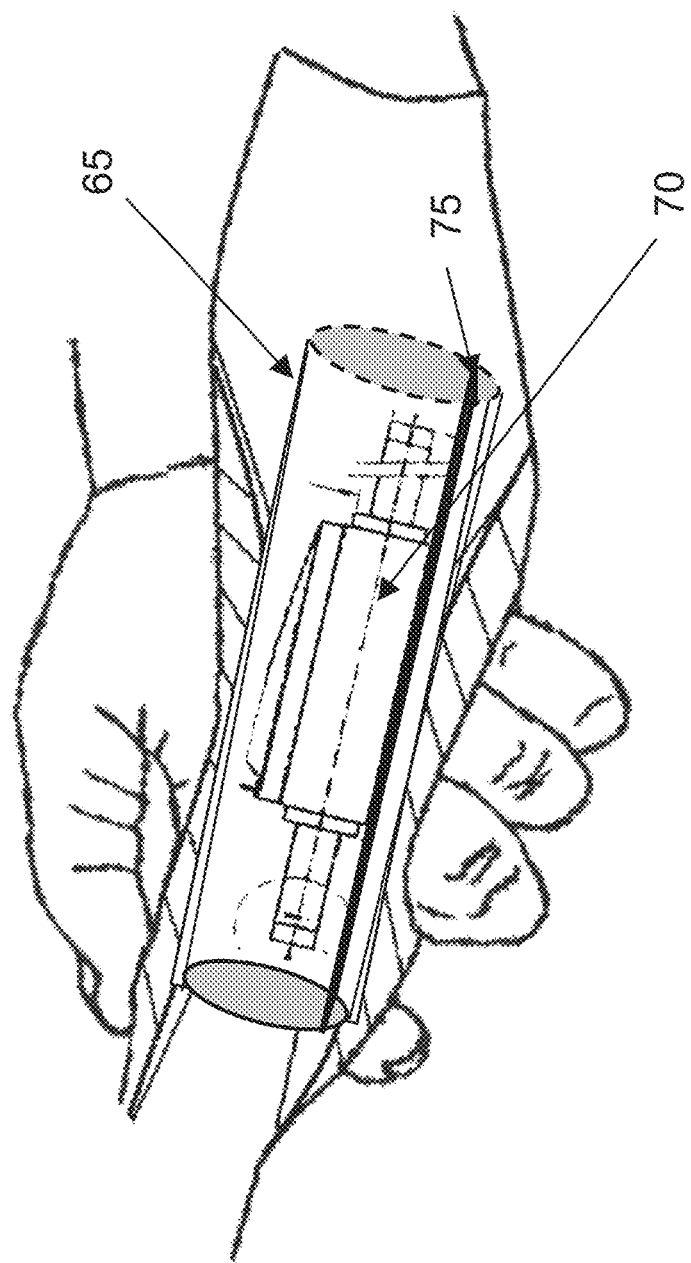
FIG. 7 depicts a view of an exemplary haptic-enabled handle having optionally deformable portions, according to an embodiment of the invention.

In another embodiment, the subsystem may be composed of an inner section (FIG. 6) that can be inserted and removed from an inner chamber 60 centrally located within outer subsystem I (FIG. 5). The former is re-usable and as it is more costly would be considered capital equipment, while the latter would be disposable as it is less expensive and in direct contact with body fluids and blood. This inner section can be manufactured in a variety of shapes and sizes and with varying materials, though the inventor believes an inner tube 65 composed of a rigid or semi-rigid shell mold (e.g. rubber and/or urethane composite) would be ideal for housing of inner actuators 70 and haptic elements as illustrated in FIG. 6 and FIG. 7. The tube can have an inner diameter, for example, between 30-40 mm and taper to a smaller diameter in the front end as to ease insertion within 60 as depicted in FIG. 7. It can be securely and reversibly positioned within 60 using a variety of mechanisms as known by those experienced in the art Inner actuators can include any type of actuator including but not limited to rotary motors, linear DC brushed or brushless motors, or other haptic actuators that are positioned upon or juxtaposed to the outer surface of the handle providing the user with tangible sensations.

By way of example, 70 is a DC brushless servomotor 80 mm in length, that has an inner rod 72 that can extend 10 mm in either front or rear portions of the motor imparting a to and fro tangible sensation either as a result of a direct effect on the housing of subsystem I or via a haptic element or interaction of haptic elements found in subsystem I and II. Motor 70 can be mounted on a shelf 75 of variable length (e.g. 180 mm) within tube 65. Shelf 75 can be coaxial within the central longitudinal axis of inner tube 65 or positioned obliquely as depicted in FIG. 6. Multiple motors can be positioned at variable (and programmable) angles with respect to the longitudinal and radial orientation of the handle. Such positioning will provide the user with tangible sensations representative of three dimensional motion and force such as torque, rotation, strain, compression, dilatation etc.

The inner tube can have one or more projections that insert into the outer handle's housing as to stabilize the two subsystems physically and generate tangible sensations more effectively. This is depicted in FIG. 6*a* where inwardly directed projections 19*p* extend centrally toward the outwardly directed projections, 65*p* that are both deformable and overlap to cause a brushing interaction that generates a characteristic tangible sensation to the user holding the handle. These projections can be composed of any combination of materials, urethane, rubber, silicon etc. and are situated on a haptic element fixated to rod 72. In this rendition, the forward facing rod contains the projections while the rear-facing rod is just a counter weight to balance the system and ensure smooth and durable operation of the linear motor.

Figure 8:
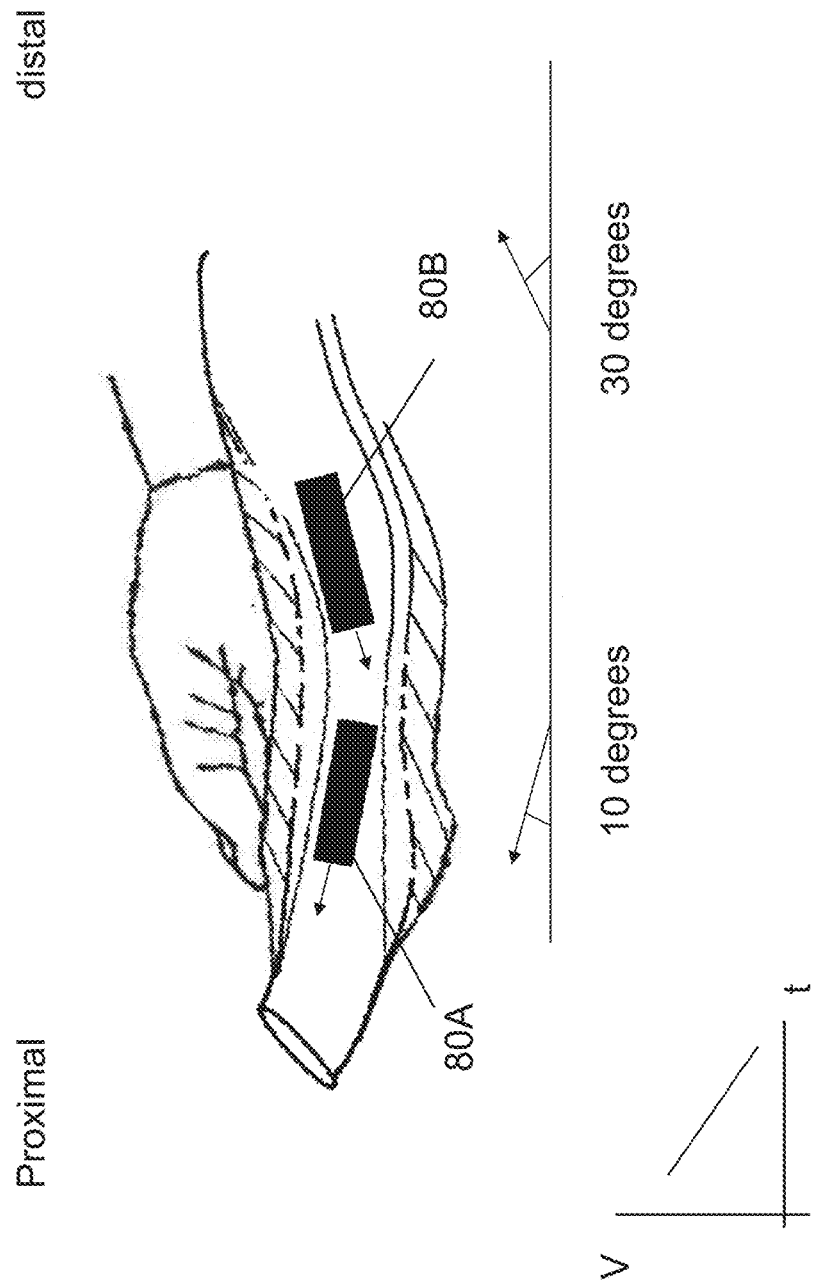
FIGS. 8 and 8a illustrate how a pair of haptic actuators disposed within a deformable haptic medical device handle can provide an operator with a sensory experience, according to an embodiment of the invention.
Figure 8A:
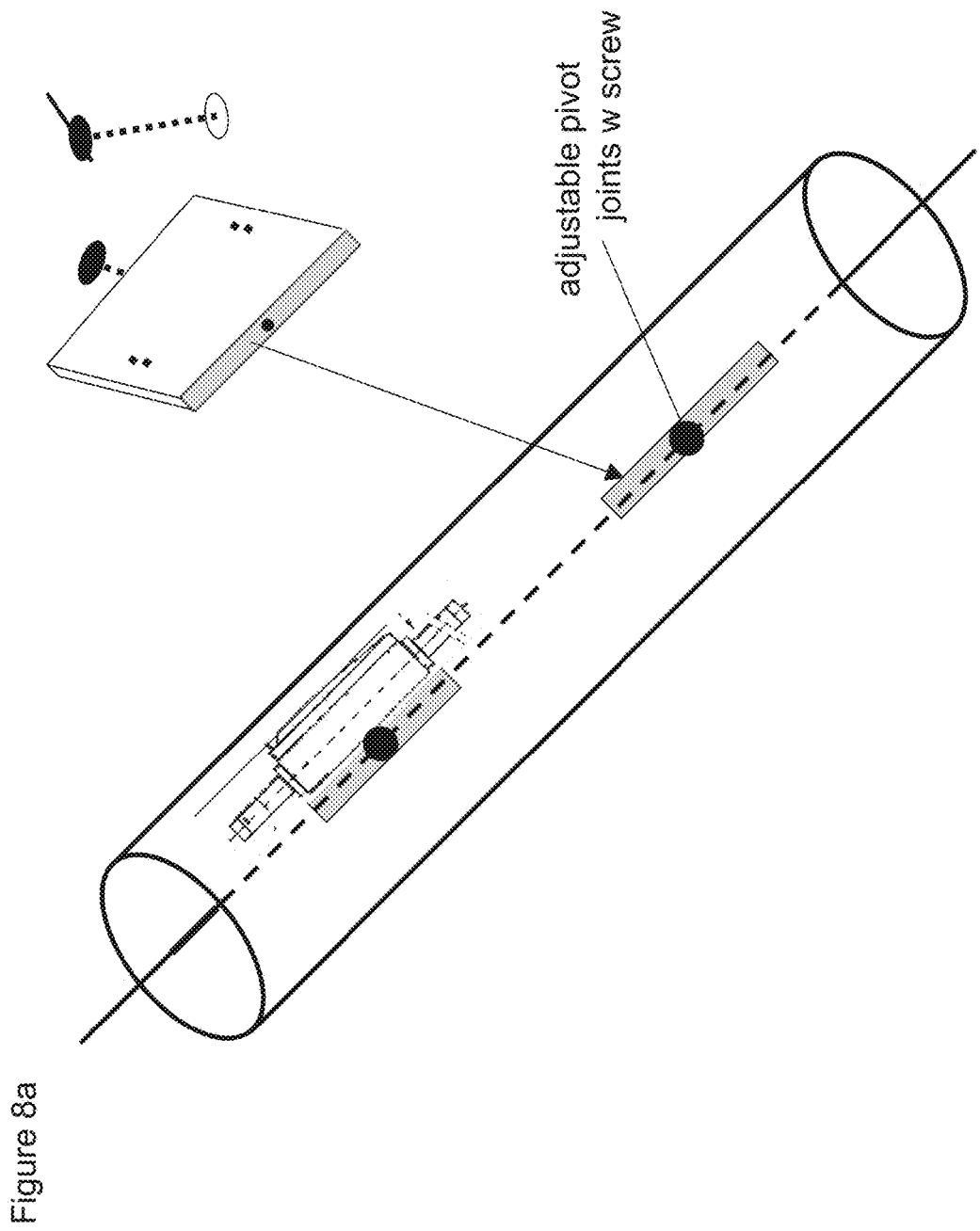

More than one motor can be used and positioned in a variety of configurations such as with minimal overlap (dashed arrow in FIG. 6) or with an overlap over some distance or a single motor can be used as in FIG. 7. In one mode of the invention, two or more motors in series are positioned at different and controllable angles within an angled deformable handle (FIG. 8). The motors are mounted upon shelves that can pivot, the angle able to be adjusted manually or electronically (FIG. 8*a*). The shape of the inner conduit of subsystem II would be manufactured accordingly. The orientation of the motors or other haptic actuator (e.g. embedded, deformable piezoceramic foil), in this embodiment is designed to impart tangible sensations that more effectively convey information related to larger segments of moving biological tissue. By way of example, strain information and torsion can be tactually communicated to the operator with such a design. The activation times of each of two or more motors would be delayed based on the velocity of the sensor-acquired data from one or more sensors. If one sensor is used to acquire motion data than the delay would be programmed based on a known relationship between the sensor acquired data and actual tissue velocity (graph insert in FIG. 8). This relationship would be inverse as the higher velocity signals would have a shorter time delay between activation of motor 80A and motor 80B in FIG. 8. Both the velocity of the shaft of each motor and the time delay between activation of motor 80A and 80B will relate to the sensor-acquired data. If two (or more sensors) are used to obtain the sensor acquired data (e.g. sensor A and B) then each sensors' signal would relate to the action of each representative motor (motor 80A and 80B). The GUHI would represent this accordingly as illustrated in FIG. 9 where the velocity of motors 80A and 80B (here represented as circles for simplicity purposes) reach their maximal levels 0.25 seconds apart. This value relates to tissue velocity and the location of the sensors and motors within the handle and does not require a calculation or delay constant as when only one sensor and two motors are utilized. Of note, the GUI or GUHI can display both the sensor acquired data and the action at the level of the haptic display (both not depicted for sake of simplicity). In this way, the operator can correlate sensor acquired data and the action of the motors within the haptic interface (e.g., handle) with a visual format thereby enabling the user to more closely correlate physiologically detected signals with the user's tangible sensations (multimodal feedback).

The benefit of having two sensors a distance apart and two actuators can be appreciated by looking at FIG. 10 where the curves on the top and bottom represent strain rate and strain. Strain rate is the spatial gradient of velocity. If sensors 100A and 100B are distance d apart and each is opposed to tissue having a different velocity, strain exists between these two segments of tissue. Strain rate can be derived and integrated to generate strain (occurs in the OS as described below). This strain information is then manifest as tangible sensations in the handle by using actuators that, by way of example, can deform the contour of the handle or other haptic display and impart strain to the user's tissue as if his or her hand were the anatomic tissue being sensed in real time. Both the sensor acquired data and tangible sensations can be displayed using the GUHI where the ordinate represents strain (rather than velocity or displacement). Likewise, having more than one sensor and actuator will facilitate the communication of other mechanical properties such as torsion or dysynchronous motion patterns as seen in patients with cardiomyopathy and congestive heart failure. Being able to appreciate these physiological signals during procedures will provide the operator with real time information that has both diagnostic value and can direct treatment (e.g. optimally locating pacing leads in patients receiving resynchronization pacing systems).

Figure 11A:
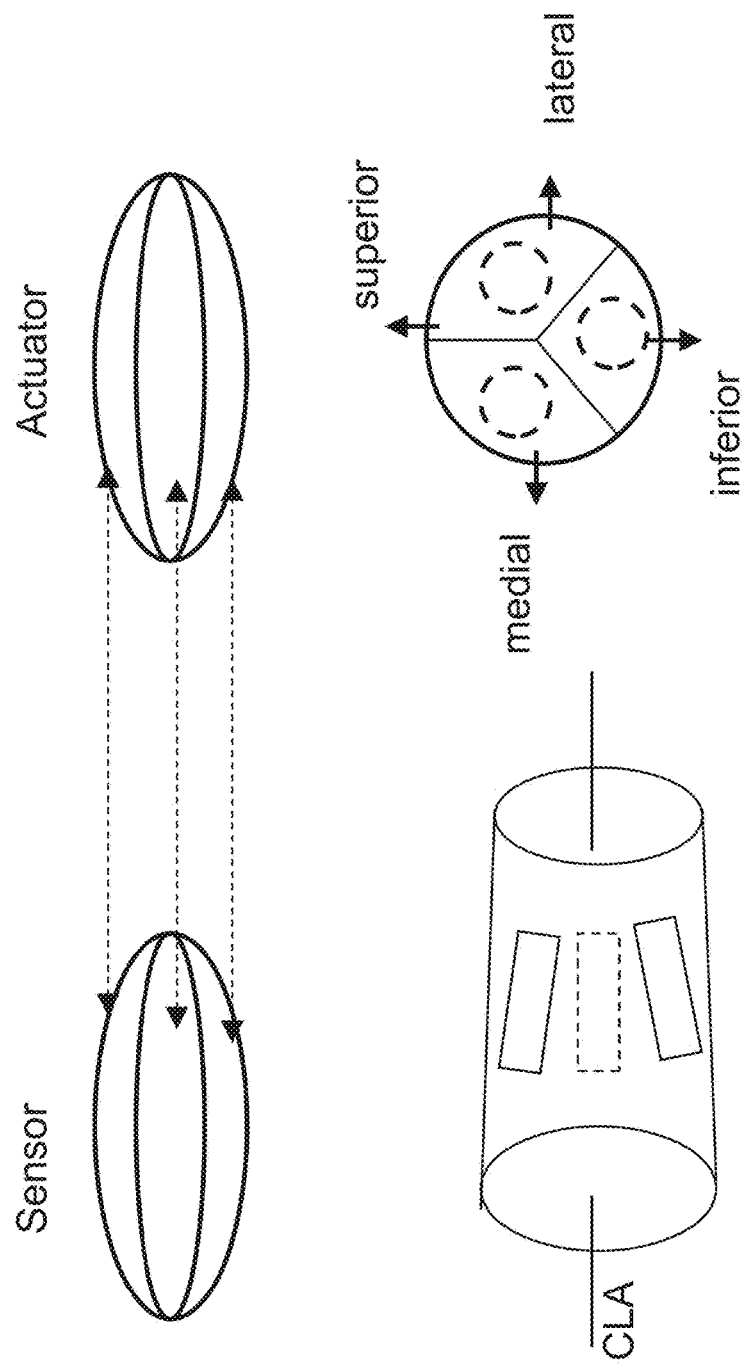
FIG. 11a is a compound illustration of the sensor-to-actuator relationship and a lumen having multiple lumens, according to an embodiment of the invention.

Alternatively or additionally, actuators can be positioned in a three dimensional arrangement and provide for a volumetric haptic display. By way of example, three linear actuators are located circumferentially about the inner aspect of the handle. Each of the three linear actuators is obliquely positioned relative to the central longitudinal axis (CLA) of the handle and attached catheter (e.g. 20 degrees), 120 degrees apart from each other and drive one or more haptic elements similarly oriented in three dimensions (FIG. 11*a*). The sensors (e.g. contact and/or non-contact) such as piezoelectric type technologies, piezoactuators, ultrasonic sensors, deformable tri-axial fiberoptic cables, magnetic, electromagnetic, resistive, capacitive, and impedance based sensing technologies, provide data representative of sensed signal vector (e.g. force, impedance, resistance, magnetic, acceleration, etc.) and which are processed to generate three dimensional information displayed at the GUHI and/or generated at the haptic handle interfaces, recreating real time events and providing the operator with information about the location of sensed signals and catheter-tissue contact uniformity (FIG. 11a bottom).

Figure 11B:
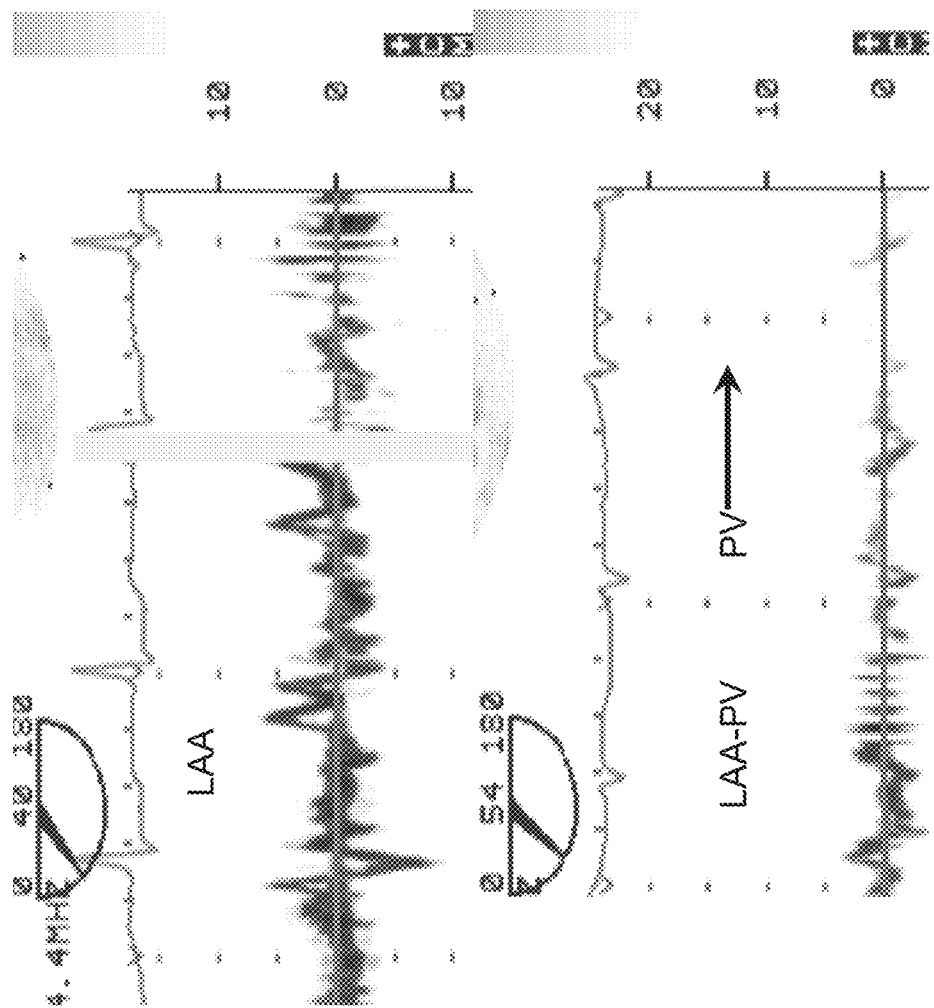
FIG. 11b represents the left atrial appendage (LAA) relation EGM activity relative to pulmonary valve (PV) activity in two temporal sequences having both EGM and haptic components, according to an embodiment of the invention.
Figure 11C:
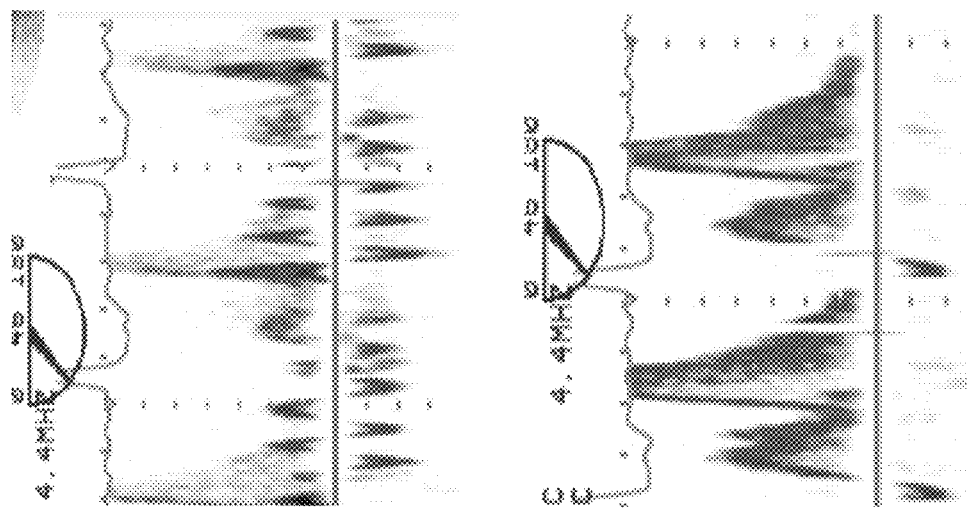
FIG. 11c represents the left atrial appendage (LAA) relation EGM activity similar to FIG. 11b, according to an embodiment of the invention.

Co-registration of anatomic position using externally located navigational systems enables the user to detect gradients in sensed physiological events (FIGS. 11b and 11c) enabling the operator to determine anatomic location (e.g. relationship between pulsatile blood flow originating from the left upper pulmonary vein (PV) and the fibrillatory motion of the left atrial appendage (LAA)). The combined effect of these signals is apparent in FIG. 11b where the high frequency signals associated with atrial arrhythmia fade away (top to bottom) and there is also overlap between pulmonary venous blood flow and LAA motion (bottom) as the sensorized catheter approaches the pulmonary vein (FIG. 11c top) and ultimately just pulmonary venous blood flow is palpable (FIG. 11c bottom). Thus, gradients in the amplitude and quality (e.g., temporal, frequency, spatial domains) of specific tangible sensations of physiological relevance provide anatomic information with haptic feedback.

Figure 11D:
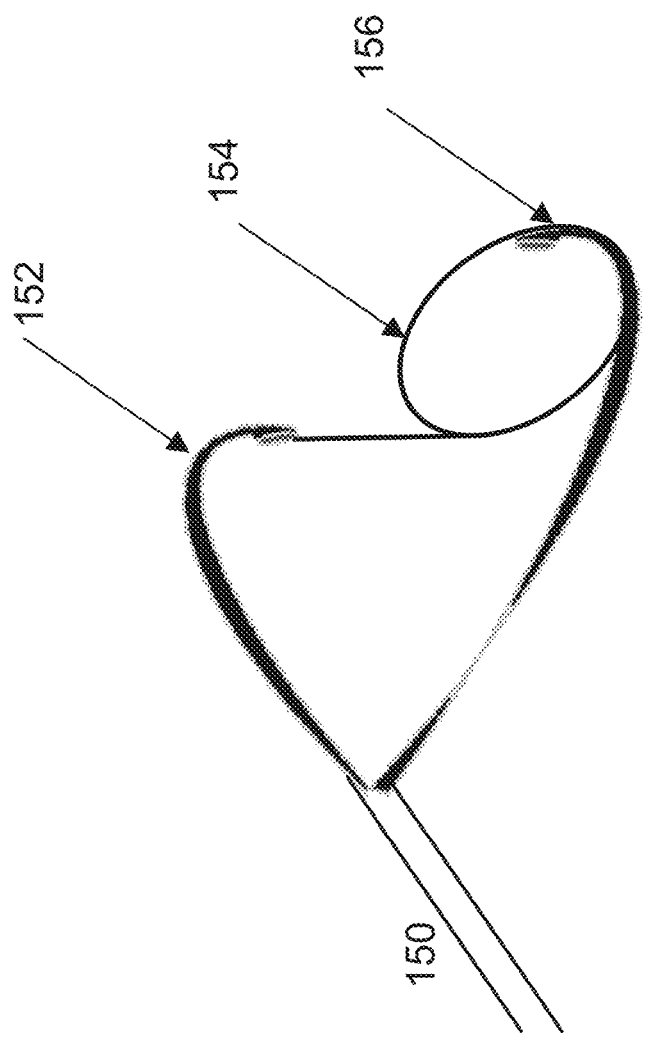
FIG. 11d shows a piezoactuator sensor material delivery arms and a wire with piezoactuator properties positioned using a deflectable sheath.

This will be particularly useful during percutaneous and minimally invasive surgical procedures during delivery of left atrial appendage (LAA) occlusion devices that require a snug fit that safely obliterate the LAA. By way of example, haptic feedback can guide the positioning of the LAA closure device after maneuvering the delivery catheters/system about the epicardial or endocardial space. In one embodiment, the sensor-acquired data is obtained from flexible piezoactuator wires (as opposed to the polyester suture/suture delivery device seen in available LAA closure devices such as the LARIAT Device; SentreHEART, Inc.) that can snare and permanently obliterate the LAA. Piezoactuator wire design is such that they the wires are flexible and responsive to: deformation during positioning within the thorax, body cavities, vasculature; contact forces along multiple points; tissue motion (e.g. LAA fibrillation); and turbulent blood flow (e.g., flow between the LAA and LA, paravalvular leaks). Referring to FIG. 11d, the top arrow 152 is a firm yet flexible piezoactuator sensor material delivery arm that is connected to a wire 154 with piezoactuator properties (middle arrow) and bottom piezoactuator delivery arm 156 all positioned using a deflectable sheath (e.g., 12-14 French) 150. Gradients in the quantity (i.e., amplitude) and quality of haptic feedback are palpably appreciated as the contacted anatomic structures change (e.g., free epicardial space—left atrium—LAA) during device delivery and as the LAA is obliterated from within the epicardial space. In one embodiment, haptic interfaces can include a haptic glove where opposing fingers (e.g., thumb-pointer) can be surrounded by similar piezoactuators as the snare wires and provide both actuation (i.e., control over the snare about the LAA) and haptic feedback in a reciprocating fashion. By way of example, each finger is representative of the two delivery arms and in one embodiment there is piezoactuator suture material that connects the two haptic fingers recreating the snaring of the LAA while recreating tangible sensations due to tissue contact and tissue motion (e.g., FIGS. 11b-11c). Knot tightening of the wire can be achieved with a tension-delivery device or other mechanism. Other materials/sensors can be used and are within the spirit and scope of this mode of the invention and the use of piezoactuators is purely exemplary.

Multiple sensors and actuators will be particularly beneficial and can also be realized in an additional embodiment, where enhancement of the user's tactile experience is provided by generating tangible sensations to the catheter proper (actuator 201), in addition to other actuators 202 and 203 (e.g. in series) that provide temporally relevant tactile data to the user from sensors 301-303 as depicted in FIG. 12. Each sensor can generate respective impulses to each actuator (i.e. 201 to 301) or combinations of sensed events can be appreciated at different actuators based on signal processing techniques (OS), the nature of sensed signals and actuator properties. A novel actuator can be positioned on the catheter using a haptic sleeve 201 that snugly fits around the body of the catheter (FIG. 12a) and has one or more conductors that run isodiametrically along the outer perimeter of the catheter to innervate the haptic sleeve and also acquire sensed data from actuator 201 (e.g. localization and distance from other actuators for calculation of timing of haptic signals relative to other actuators, sensing operator motion/force upon catheter for subtraction from sensor acquired data). The haptic sleeve is fabricated in part or wholly with material that provides a haptic response and can be also composed of sensing elements such as thin piezoelectric material (e.g., foil piezoactuators) that detect user contact. By way of example, an electroactive polymer (EAP) composed of an ionic polymer-metal composite or dielectric elastomer formed from two flexible and elastic electrodes sandwiching an electrically insulating elastomer is used for such an application. EAPs and dielectric elastomer actuators (Chiba S et al. Electroactive Polymer "Artificial Muscle" Operable in Ultra-High Hydrostatic Pressure Environment. IEEE Sensors Journal, Vol. 11, no. 1, January 2011, p. 3) exhibit a change in shape when electrically activated and can produce over 300% strain effects. As this is the most proximally located actuator (relative to the patient) it would be temporally the first activated haptic element and can provide impulses of haptic feedback to accentuate fiducial events or signals such as signals generated at the time of tissue contact (e.g. from the most distal sensor 301) and isovolumic contraction. These haptic signals are ideally representative of true physical and physiological events (recreated, non-virtual) rather than a surrogate or rendered signal. A haptic sleeve can be utilized and fitted to be part of instrumentation used in any minimally invasive procedures such as laparoscopic surgery tools, Da Vinci surgical arms and the like.

Figure 12A:
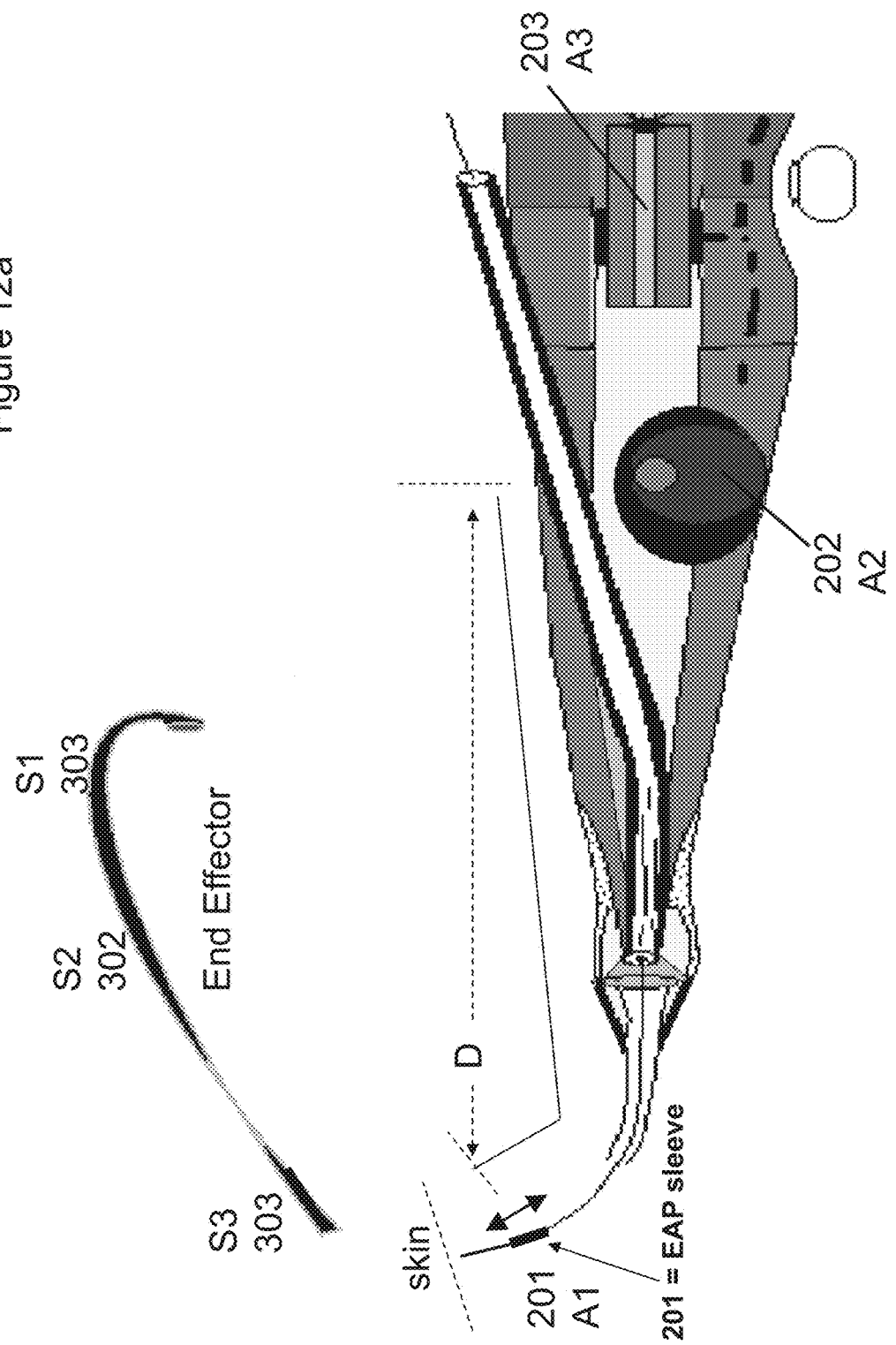
FIG. 12a is a view of an end effector that can couple to an exemplary haptic-enabled handle, according to an embodiment of the invention.
Figure 12B:
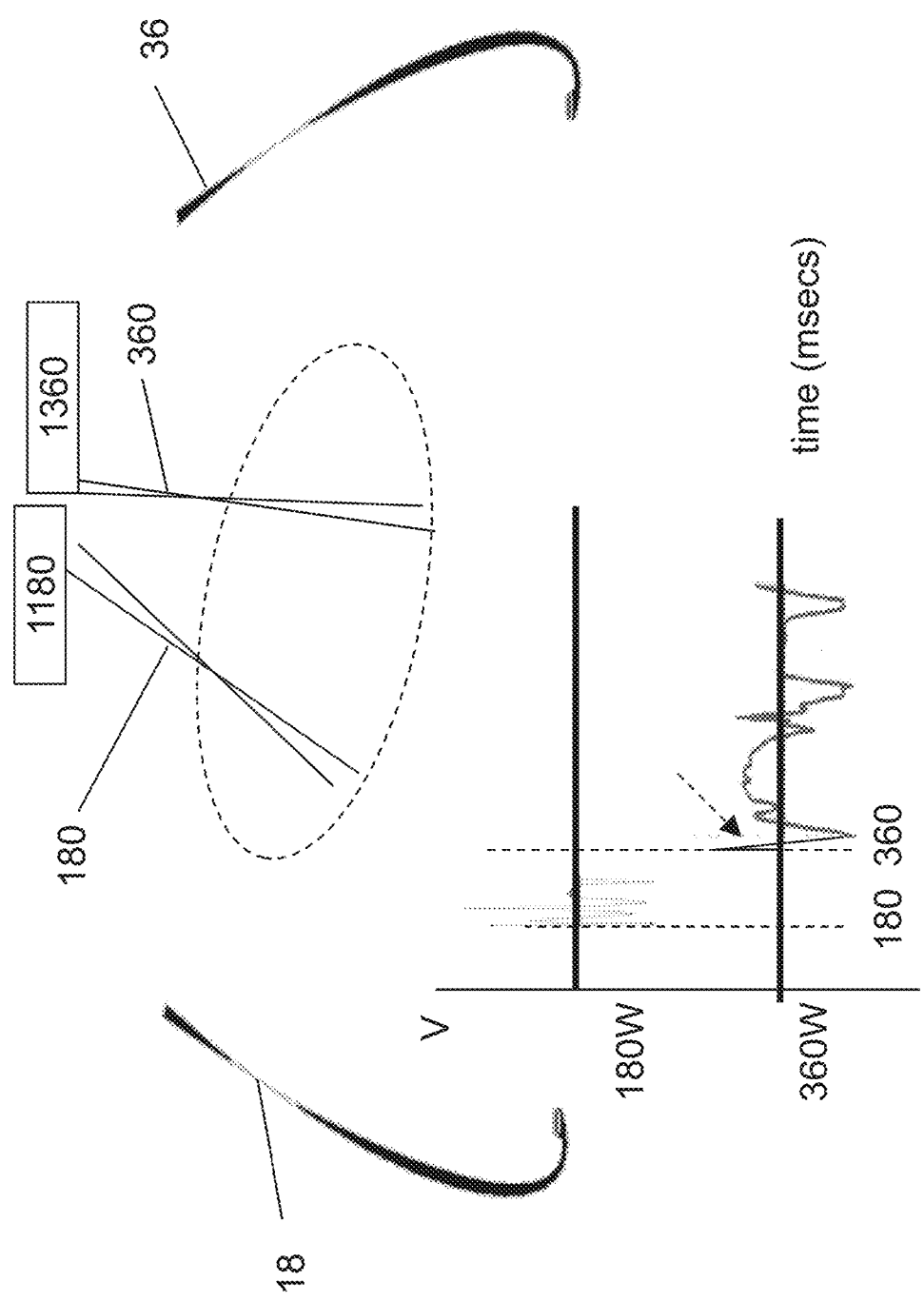
FIG. 12b is a view of minimally invasive operative tools and relationships, according to an embodiment of the invention.
Figure 12C:
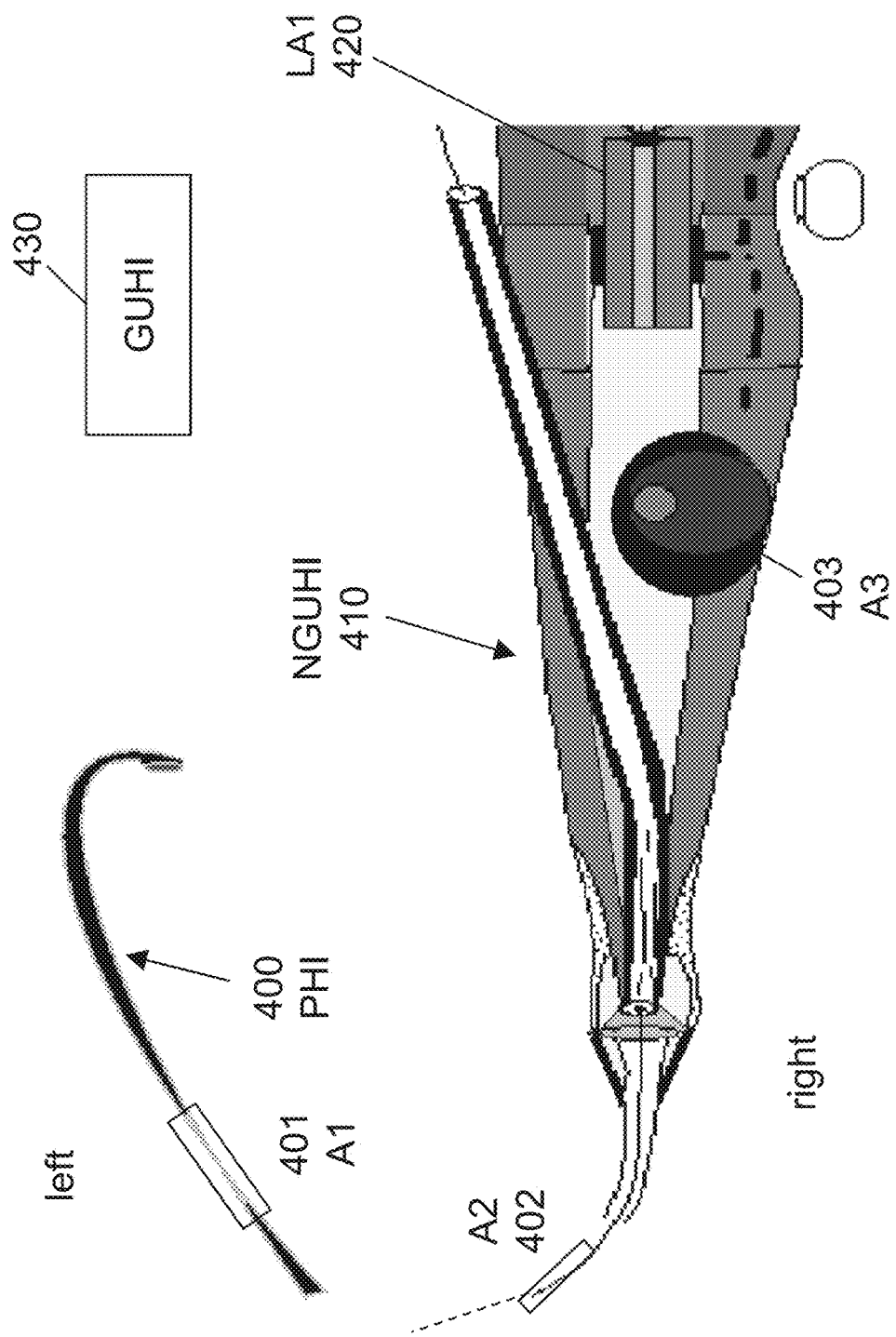
FIG. 12c is a view of an end effector that can couple to an exemplary haptic-enabled handle, according to an embodiment of the invention.

FIG. 12b depicts such an application. Minimally invasive operative tools 180 and 360 contact moving and non-moving biological tissue, 1180 and 1360, at times=t 180 msec and t=360 msec. The ordinate represents sensor acquired data and thus, sensed haptic element velocity. By way of example, moving biological tissue 1360 is muscle (e.g., skeletal, diaphragm, bladder) that is contracting at a cycle length of 1000 msecs, and 1180 is nearby non-contractile tissue. The surface of the skin (instrument entry point) is represented by the dotted ellipse. The properties of the skin and intervening anatomic structures and dampening effects of 180 and 360 attenuate any tactile signals related to 1180 and 1360 and their interface with 180 and 360. The hand held passive haptic interfaces 18 and 36 are used to manipulate and control 180 and 360, respectively and can be used at the bedside, or in other embodiments, remotely or robotically and thus can act as an active haptic interface in this mode of the invention both in the sense of controlling the actions of the inserted instrumentation and in one embodiment, by having controls that can modify the user experience as a non-graphical user haptic interface or NGUHI (FIG. 12c).

Surgical instruments 180 and 360 can be fitted with sensors of any type (not depicted) or be composed partially or entirely of contact sensor material such as piezoelectric composites, wurzite crystal, nanotechnology based materials such as Zinc Oxide composites, shape memory alloy, microfabricated sensors and/or function with non-contact sensor localization technology such as three dimensional navigational systems known by those experienced in the art. Preferably, 180 and 360 are at least in part composed of one or more deformable, malleable sensor materials (e.g., piezoactuators) that have material properties conducive to detecting relevant physical and physiological signals.

On bottom of FIG. 12b, waveforms 180W and 360W illustrate the workings of this invention. Waveform 180W represents sensed events at time of tissue contact between 180 and 1180. 1180 is a non-moving biological tissue or organ or anatomic structure being retracted (e.g., pericardium) so that 360 can access 1360 (e.g. heart) to perform a therapeutic intervention. When 360 contacts 1360, an impulse (dotted arrow) is sensed and palpable at time of instrument-tissue contact and then cardiac tissue motion is palpable. Mixed sensor technologies can be implemented (contact and non-contact) and gather information (i.e., sensor acquired data) about cardiac tissue motion, forces at the tissue-instrument interface etc. which is then displayed at one or more haptic interfaces. By way of example, in FIG. 12c, we see passive haptic interface 400 with haptic element, 401 (e.g. movable EAP haptic sleeve) that is held by the operator's left hand and directly or indirectly (e.g. telerobotically) controls the inserted instrumentation. Non-graphical user haptic interface (NGUHI) 410, is held with the operator's right hand and has haptic element 402, rotary motor 403 and linear actuator 420, all of which provide tangible sensations to the user as well. NGUHI can have one or more controls that can modify the haptic experience while the OS maintains the temporal relationships of fiducial events such as time of tissue contact or time of isovolumic contraction. A separate GUHI 430 that functions with OS and also provide for visual and/or haptic feedback can be implemented as well.

Figure 12D:
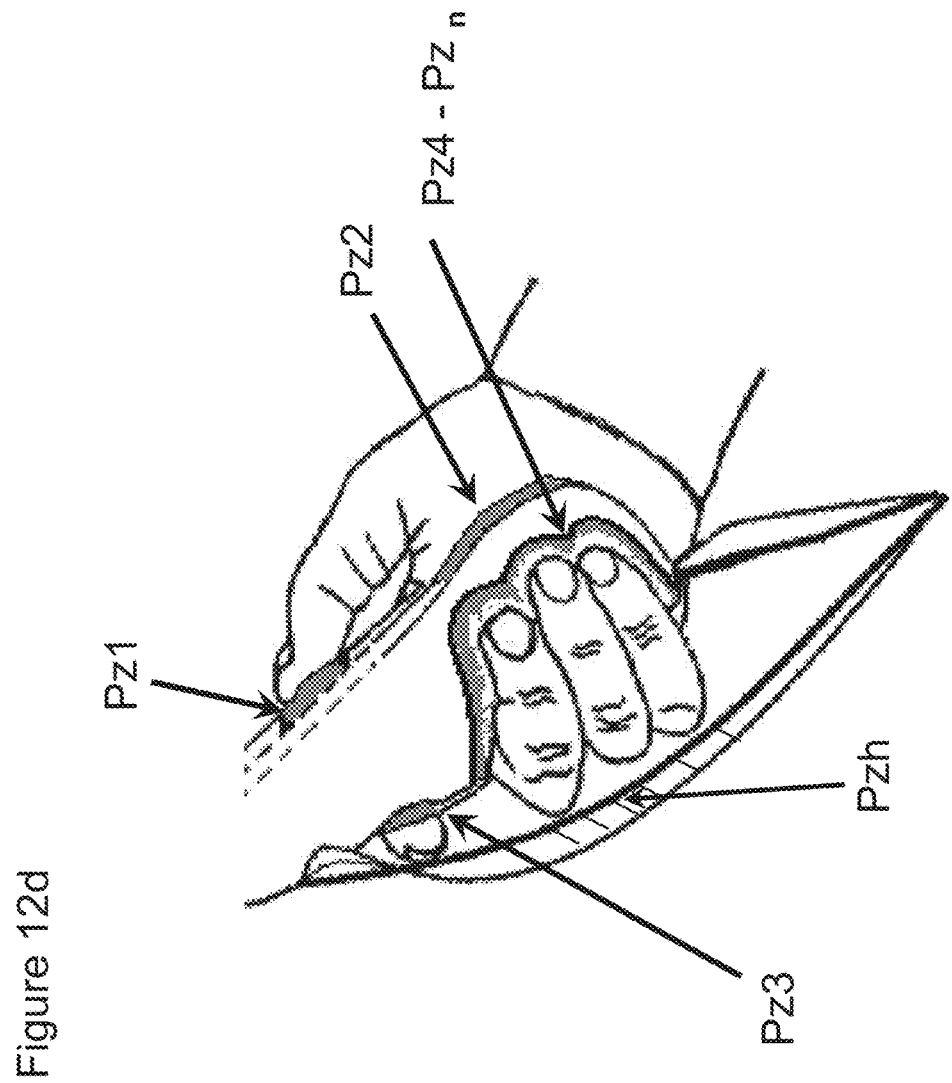
FIG. 12d is a view of a construct of a series/array of bendable piezoactuators, according to an embodiment of the invention.
Figure 14:
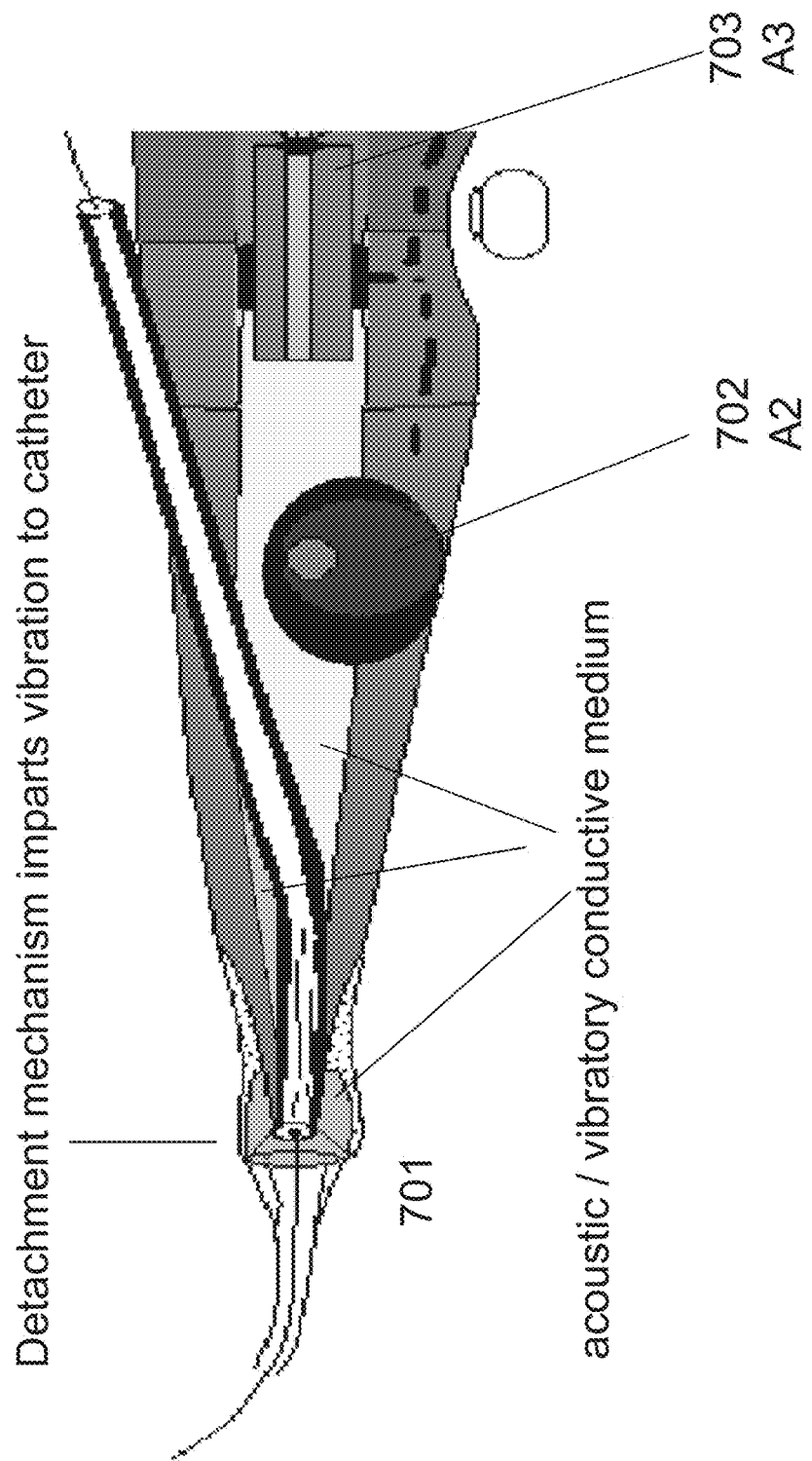
FIG. 14 presents a view of an end effector that can couple to an exemplary haptic-enabled handle according to the disclosure, according to an embodiment of the invention.

An additional and/or alternative means for transmitting tangible sensations to the catheter proper consists of a haptic element that imparts vibratory/motion signals to the catheter via a conductive medium, smart material/fluid, piezoelectric mechanism (e.g. speaker), or other means (FIG. 13). By way of example, an inverted speaker 601 is used to transmit vibratory signals to the catheter. Speaker 601 is configured to house an inner catheter as it courses through the conduit of the haptic handle leading and connecting with the central axis of Speaker 601 (inset FIG. 13, inverted speaker) which also secures the inner and outer guiding catheter by having elastic material properties that allow the catheter to slide to and fro but also be secured in position (FIG. 14) with the appropriate coefficient of friction. In one embodiment, this provides a detachment mechanism to separate the handle and internal actuators from the external guiding catheter and inner conduit. In this mode of the invention, it would be preferable for a first actuator A1 to be activated first and a second actuator A2 (rotary motor) and a third actuator A3 (linear actuator) to be activated in series thereafter to provide a surround "sound" effect as illustrated in FIG. 12-14 (data acquired respectively from sensors 301-303). Such a haptic response will be ideal for recreating the sensation of pulsatile blood flow. Implementation of a series or array of bendable piezoactuators similar to those manufactured by Physik Instrumente (DuraAct patch) may be utilized in accordance with one embodiment. FIG. 12d, depicts a specific construct of a series/array of bendable piezoactuators, Pzl-n, are arranged as to provide the all of the user's fingers, palm (thenar eminence) and via a strap, the dorsal aspect of the hand (Pzh), with tangible sensations which will provide a hand held volumetric haptic display in real time.

Any number or type of haptic interfaces that utilizes flat and deformable actuators (e.g. stack piezoactuators) can be utilized to provide tangible sensations including mechanisms for haptic rendering for the creation and recreation of the inertial and viscous forces (mass and viscosity) at the interface between human tissue and sensor. Such a design will serve to render the user's haptic experience in a novel fashion and create a virtual simulation of the operator's hand, wrist etc as one or more segments of biological tissue, vasculature and/or the actual inserted instrumentation.

The timing of sensed events at the sensors S1-S3 and haptic events at the actuators A1-A3 would be related or proportionate. Optimally, the time of the initial sensed and initial haptic event will have no detectable delay (e.g. time of tissue contact).

Such sophisticated coordination between sensed and haptic signals will require a sophisticated operating system (OS). Inert viscoelastic fluid, gel, or material and/or smart material, smart fluids/gels can be implemented to help smooth and diffuse the actions occurring at discrete locations (serial actuators), optimize the haptic experience, provide additional haptic effects or attenuate the amplitude of actuator signals without affecting the quality of or data contained within the haptic display. Any technologies can be implemented to create the desired haptic effects and the invention is not limited in scope or spirit to any specific type of haptic interface, actuator or haptic elements. The workings of the invention can be combined with robotic systems that modify the user's actions and improve dexterous control of inserted instrumentation (e.g. removal of tremor).

Multi-Sensor Compatibility OS

In various embodiments, the operating system is designed to be compatible with multiple technologies and a variety of applications. The OS operating environment will enable clinicians to use a multitude of sensors and actuators from different vendors and ensure quality control and an accurate temporal haptic representation of real time events.

Hardware is composed of actuators, motors, ERF, MRF and any equipment capable of generating a tangible sensation or haptic experience as well as associated microprocessors, embedded systems and the like. OS also consists of application programs structured to integrate input data acquired with different sensor technologies (sensor acquired data), and multiple motion control systems, drivers and software used to control the actuators response (output) to sensor acquired data and generate the Haptic Display Data (HDD). Control systems are used to correlate sensor-acquired data and HDD and fine tune the relationship (e.g. linearity and temporal relationships) between sensor acquired data and HDD. This is communicated using the GUHI (as stored data or in real time). Thus, the control systems serve to ensure that there is a faithful recreation of the sensor acquired data at the level of the HDD (true passivity or transparency) or alternatively, modify the user's tangible sensations or haptic experience (e.g. changes in signal amplitude, haptic rendering) to suit the preference of the user without affecting temporal relationships and at the same time maintaining linearity between sensed physiological signals and haptically displayed events.

The relationship between the sensor acquired data and HDD should not be temporally delayed. Thus, when haptic rendering techniques are applied, the timing of key changes in position, impulses of motion and acceleration/deceleration phases are maintained. By way of example, based on a user command at the GUHI, the operating system may initiate a decrease in the amplitude of the haptic signals (e.g. reduce degree of displacement, velocity and/or acceleration of a linear DC servomotor relative to true displacement of sensor) for a specified time period (e.g. to suit the needs of a particular user who is new to using embodiments of the invention). Reducing the amplitude of a linear motor's displacement, velocity and/or acceleration can do this, but timing is not altered and the time of palpation of the haptic effect is maintained and related to signals from moving biological tissue. Likewise, force feedback displayed in the haptic handle can be attenuated but force responses are linearly related to sensor acquired data (e.g. velocity) and signal processing (e.g., admittance haptic interface) cannot affect timing or signal quality. Likewise, when the sensor-acquired data is a velocity signal, acceleration signal or displacement signal, signal processing will not alter timing. Control systems are implemented to monitor the system in this regard.

Figure 15:
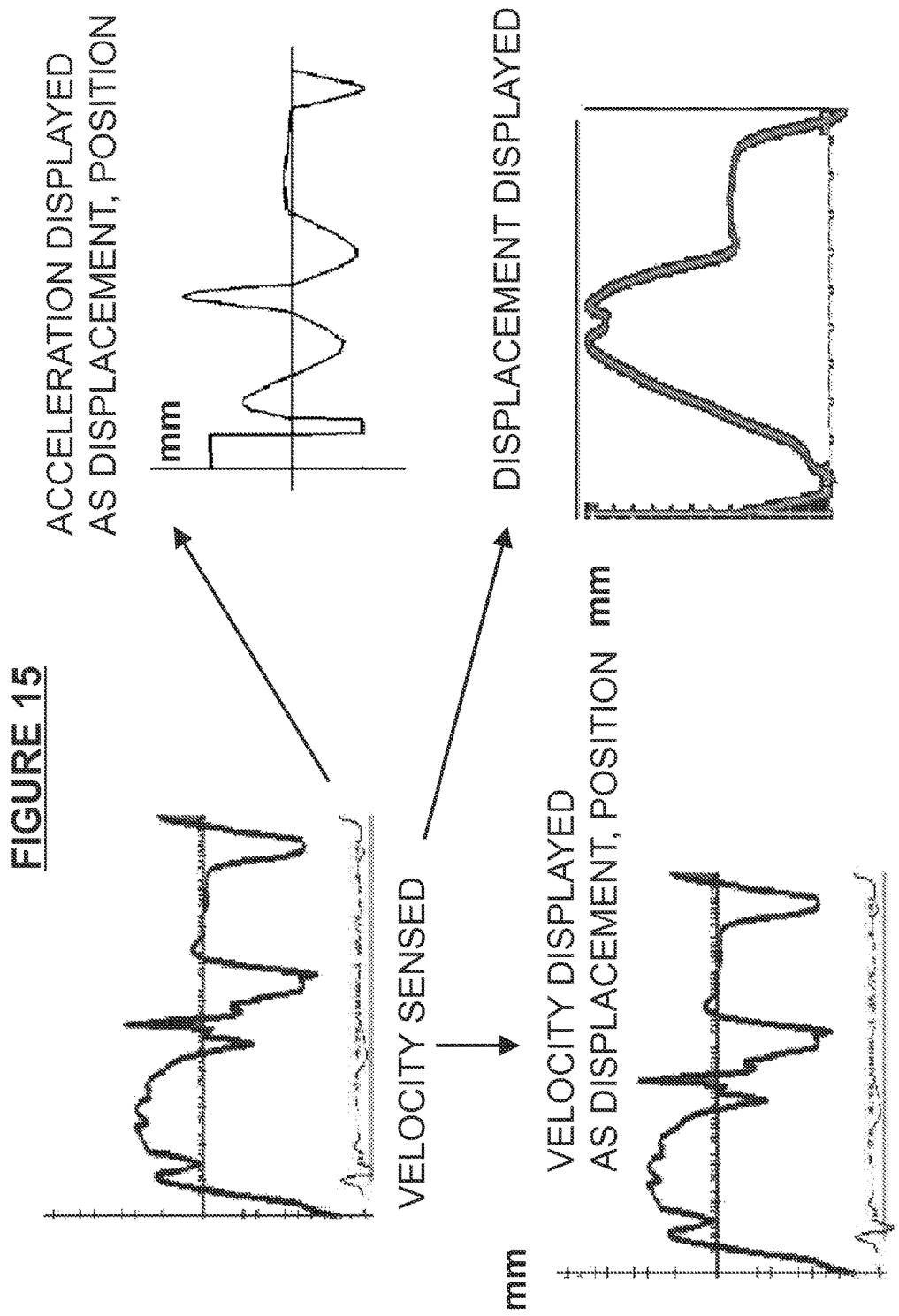
FIG. 15 is a compound temporal view of an optional control experience for an operator illustrating velocity-sensed, velocity-displayed and displacement/position, according to an embodiment of the invention.

Another example of how the control system maintains accuracy relates to using activation of ERF contained within a sealed cavity about the perimeter of the HH for attenuation of haptic signals (charged ERF will have greater viscosity and decrease the amplitude of conducted vibrations). The temporal relationship between the sensor acquired data and HDD is maintained, even if signal quality (e.g. amplitude and frequency information) is affected. Use of ERF may be desirable for some applications (and simpler to implement) rather than adjusting the scalar range of multiple indices (velocity, acceleration, displacement). For example, a modification in time dependent position of a haptic element designed to create a tangible sensation (e.g. displacement of a linear motor over a specified cardiac cycle length) will necessarily result in a change in velocity and acceleration, altering the accurate recreation of sensed signals, corrupting the acquired data and leading to a temporal offset of palpable events (e.g. time of catheter tissue contact, time of isovolumic contraction). The control system provides for signal processing as to eliminate data corruption regardless of sensor types or actuators and the scope and spirit of the invention is not limited to any specific type of hardware, firmware or software. Thus in one embodiment, the OS implements sensors within the HDD that correlate event timing. By way of example, similar sensors (e.g. piezoelectric) are present within the HH as at the sensor level (reciprocating). Quadrature and other encoders, hall sensors and the like can be used to monitor the relative position of the sensors/actuator's haptic elements and ensure that a linear temporal relationship exists at all times. In one mode of the invention, the sensor(s) within the HH are similarly situated upon a catheter segment or other instrumentation with similar properties as the actual sensorized catheter and contained within a similar milieu, as to replicate the conditions at the level of the sensor. This will be more important if the user modifies the sensor acquired data signals displayed properties significantly (which is reflected by the delta sign rather than the equivalent sign in the GUHI). By way of example, the user may choose to integrate or differentiate sensor-acquired data representative of tissue velocity in order to display (e.g. haptically) displacement or acceleration, respectively (FIG. 15). Event timing is maintained by the OS. Additionally, the OS can use prediction algorithms and pre-emptive software, filtering techniques, interpolation of dropped signals, Runge-Kutta integration, summation averaging, ensemble averaging and analysis of prior data loops, etc., to compensate for lags in processing time or signal noise. Visual (and haptic) representations of temporal events with the GUHI also provide feedback to the operator in this regard during any programming changes.

In a preferable embodiment, fiducial events will have characteristic signals such as high frequency, high amplitude waveforms of short duration. These can be identified in the operating system as signature events and as such are never temporally modified (e.g., differentiated) during signal processing and can even be amplified or modified to have characteristic palpable signatures when displayed at the haptic interface. Examples of such physiological and physical events include time of tissue-catheter contact, time of isovolumic myocardial contraction, peaks in pulmonary venous blood flow velocity, peaks in coronary sinus blood flow velocity. These signature haptic signals will serve to clearly notify the operator when they are proximate to cardiac tissue, near the pulmonary venous os (location of delivering ablative therapy), close to the coronary sinus os (location of delivering a pacing lead about the left ventricle). One or more of the actuators can display these haptic signals. Labeling sensed events as fiducial events can be done automatically by the operating system based on specific signal characteristics, programmed by a user based on template data acquired from one or more patients, or semi-automatically determined based on certain preset criteria that are default criteria or criteria entered by the user into the operating system.

Referring to FIG. 16, we see the workings of OS. Sensor signals (e.g. displacement, velocity and/or acceleration) from sensorized catheter, 705, are input into 710 as sensor acquired data, as well as force information (F) and auxiliary data (AUX) (e.g. those acquired with ultrasound, accelerometers, impedance data and auxiliary externally located equipment (non-contact sensors) such as three dimensional and four dimensional navigational systems known by those experienced in the art). Different application software will be needed to process the sensor acquired data at 710 and generate the appropriate haptic representation or HDD. Processor 10 receives the signals from 710 and if needed performs AD conversion, amplification, PID algorithms, filtering, signal conditioning etc. Processor 10 is part of OS. OS automatically recognizes which sensor acquired data should be processed with the appropriate application software in real time and drives the appropriate motor controllers/haptic actuators based on the characteristic properties of specific sensor acquired data and/or user programming. Microprocessors can be part of a CPU and/or embedded systems such as a field programmable gate array or FPGA, Xilinx, or as an integrated chip that can even be deployed within subsystem II.

By way of example, different motors require different drivers (11 in FIG. 16), motor controllers (12 in FIG. 16) and encoders/analog hall sensors. Different sensors will require different signal processing. Force sensing can implement software that implements an admittance haptic interface. Motion sensing (velocity, position, acceleration) will require a comprehensive development environment such as that offered by National Instruments. Three-dimensional navigational systems work with different software programs that may be proprietary to particular manufacturers. OS is designed to function with different vendors and apply their software and hardware to the acquisition of data representative of single or multi-dimensional cardiac tissue physical properties and communicate this to the operator using a real time, non-virtual display (e.g. haptic handle interface) that is tailored to user preference without corrupting the temporal relationship between physiological events at the sensor side and the user's appreciation of generated tangible sensations at the haptic display (e.g. Motor A in FIG. 16). Likewise, the OS can be applied to testing of various sensors and HDD in the laboratory setting as illustrated in FIG. 17 where Motor B is used to impart motion and force to a sensorized catheter using a set of stored testing motion profiles. Comparisons are made between Motor B and Motor A (the haptic display or haptic handle) for quality assurance. Careful monitoring of iterative technologies will be required to maintain quality control. The foregoing text-based descriptions and scenarios are intended as illustrative and not limiting as to the various implementations and configurations for the family of cardiac and organ support modalities taught herein and should be considered as merely a partial illumination thereof.

EXAMPLES

The following examples are also intended as illustrative and in no manner limiting as to the scope and breadth of the foregoing description and the accompanying drawings to those of skill in the art.

I) A user interface including:
  a haptic handle interface; as a hand held unit consisting of at least one of: actuator, linear motor, rotary motor, piezoactuator, piezoelectric foil, bender piezoactuator, smart fluid/material, electroactive polymer, or any means for providing tangible sensations which impart real time, adjustable tangible sensations to a user including but not limited to force, tactile, proprioceptive and kinesthetic feedback; where the haptic handle interface is attachable and detachable to an elongate member fit with distally located contact sensor(s) and/or functioning with non-contact sensors which acquire physical, physiological and/or anatomical data from biological tissue and;
  an active graphical user haptic interface that controls the tangible sensations delivered by the passive haptic interface based on the user's commands input into the active graphical user haptic interface.

II) The active graphical user haptic interface in example I which provides for a touch sensitive screen that imparts haptic effects of physiological significance to the user.

III) The active graphical user haptic interface in example I implementing a graphical format such as icons and visual indicators similar to that commonly seen with the notations and symbols used with musical scores to convey temporal and frequency dependent information to the user in real time or as stored data.

IV) Where said icons and visual indicators of the active graphical user interface in example III) provide the user with an interactive tool for programming and adjusting the quality and quantity of the tangible sensations palpable at the passive haptic interface via an operating system with programmable software/code.

V) Where said adjustable tangible sensations of example I maintain real time temporal relationships to physical and physiological fiducial events detected by said sensors regardless of programming changes made by the user.

VI) An operating system that provides for real time automatic determination of how to process a spectrum of input signals from the contact and/or non-contact sensors of example I with the appropriate software applications/processor(s), and output data to the respective motor controllers/drivers and actuators used for generating tangible sensations at the passive haptic interface.

VII) Where said elongate member in example I is a catheter inserted into one of a body cavity, cardiac structure, vascular structure.

VII) Where said elongate member in example I is used to deliver one or more of: an inner elongate member; inner catheter; pharmacologic agents; radiofrequency energy; electromagnetic energy; cryotherapy; thermal energy; acoustic energy; ultrasonic energy; electricity; mechanical force; suture material; ligature; and surgical instrumentation.

VIII) Where said elongate member of example I is able to be deformed or manipulated by a user inputting commands at the active graphical user haptic interface or haptic handle interface to control the location and position of the elongate member.

IX) Where said active graphical user haptic interface of example I is in format of a heads up display located upon a radiopaque glass enclosure designed to shield the user from ionizing radiation X) Where said haptic handle interface of example I is composed of more than one element for imparting tangible sensations to a user, where said tangible sensations provide one or more sensations representative of a gradient in the quality or quantity of sensed signals in spatial, amplitude, and frequency domains.

XI) Where said haptic handle interface providing for the tangible sensations in example VI is composed of a series/array of bendable piezoactuators positioned in a specific fashion as to contact one or more digits of the hand, thenar eminence of the palm, dorsal aspect of the hand/wrist or other anatomic site.

XII) Where said haptic handle interface of example I includes one of a mobile haptic element in form of a sleeve or separate haptic handle situated upon the elongated member, haptic transducer that imparts tangible sensations to the elongated member.

XII) Where said radiopaque glass enclosure of example IX) is curved and positioned with an instrument cluster containing one or more seats, controls and monitoring equipment along with passive and active user interfaces in a user friendly design similar in lay out to the front two seats of an automobile, where said passive haptic user interface is fit with one or more dexterous haptic glove(s) used to control the elongate member of example I.

XIII) The elongate member of example I where it is composed wholly or partially of sensor material including but not limited to piezoactuators, piezoelectric composite, wurzite crystal, zinc oxide nanosensors, or shape memory alloy.

XIV) The elongate member of example I where said elongate member is instrumentation used as part of a telerobotically operated surgical system.

XV) The haptic handle interface of example I, where the display is a hand-held handle structured such that the components for creating haptic effects are protected from excessive externally applied force from the user.

The invention claimed is:

1. An operating system providing user customization of a haptic apparatus, comprising:
  a computer processor operatively coupled to a non-transitory data storage medium containing instructions that when executed cause the computer processor to: receive a series of continuous real time sensor acquired data from a catheter or surgical instrument, the data having a temporal relationship with sensed physiological, and physical events related to moving biological organ, muscle, cardiac valve, vasculature tissue, or flowing blood; process the sensor acquired data to create a plurality of processed signals; output the plurality of processed signals to;
  hardware, configured to recreate tangible palpable sensations representative of three dimensional motion via at least one haptic apparatus; and a graphical user haptic interface configured in response to user customized programming; and modify the processed signals in real time based on the user customized programming received from the graphical user haptic interface without altering the temporal relationship of the real time sensor acquired data and the sensed physiological and physical events while enabling adjustments to the tangible palpable sensations recreated by the haptic apparatus that replicates sensed physiological, and physical events.

2. The operating system of claim 1, wherein the user customized programming may alter the amplitude of tangible palpable sensations recreated on the haptic apparatus.

3. The operating system of claim 1, wherein the user customized programming may alter the quality of tangible palpable sensations recreated on the haptic apparatus.

4. The operating system of claim 1, wherein the user customized programming may modify the tangible palpable sensations recreated by the haptic apparatus by modifying the properties of the processed signals by applying one or more algorithms during specific time frames to the baseline signal.

5. The operating system of claim 1, wherein the user customized programming may modify the tangible palpable sensations recreated by the haptic apparatus by modifying properties of the processed signals by adjusting the position of one or more actuators or haptic elements of the haptic apparatus.

6. The operating system of claim 1, wherein the operating system is automatically programmable in real time based on type of sensor acquired data.

7. The operating system of claim 1 wherein the sensor acquired data provided includes temporal and spatial information regarding a real time location of a catheter or medical instrument.

8. The operating system of claim 1, wherein the sensor acquired data includes at least one of: force, strain, strain rate, tissue displacement, velocity, acceleration, pressure, blood pressure, blood flow, blood flow velocity, blood flow acceleration, blood flow laminarity or turbulence, contact or non-contact sensor data, measurements of electrical or mechanical dysynchrony, torsion, and rotation.

9. The operating system of claim 1, wherein the sensor acquired data is obtained during at least one of the following cardiovascular procedures: transeptal puncture, ablation procedures, left atrial appendage closure, delivery and extraction of pacing and defibrillation electrodes and leads, repair and replacement of cardiac valves and tissue, delivery of therapeutic cardiac devices, and delivery of vascular devices.

10. The operating system of claim 1, wherein the sensor acquired data is displayed on the graphical user haptic interface in conjunction with a surround sound audio display that generates sound replicating sensed physiological and physical events emanating from moving biological tissue, as audible sensations occurring as a result of the elongate medical device's sensorized distal end sensing actual real time compression and rarefaction events emanating from moving biological tissue and presenting this as an audible field to the operator in three dimensional space thereby providing a perception that the operator is hearing sound as if from near or within the moving biological tissue.

11. The operating system of claim 10, wherein the surround sound audio display:
generates sounds that correlate with frequency and amplitude information sensed;
maintains a three dimensional spatial and temporal relationship to the sensor acquired data in real time;
modifies the audio display of the sensor acquired data qualitatively and quantitatively and without alteration of the temporal relationship or three dimensional spatial relationship.

12. The operating system of claim 1, wherein the acquired data is based on measurements of at least one of: electromagnetic, magnetic, thermal, electric, ultrasonic, piezoelectric, piezotronic, capacitive, impedance, complex impedance, admittance, resistive, strain, mechanical deformation, compliance, resistance, elasticity, tissue damage, positioning or navigational system based sensors, contact and non-contact sensors.

13. The operating system of claim 1, wherein the graphical user haptic interface provides a graphical format similar to a musical score which displays notations and symbols that describe and communicate one or more of:
haptic signals that replicate sensed physiological and physical events as if the haptic signals were occurring as a result of actual real time palpation of moving biological tissue, the action of the actuators, and sensor acquired data in the frequency and time domains.

14. The operating system of claim 1, wherein the data having a temporal relationship with sensed physiological and physical events is representative of different kinds of biological tissues.

15. The operating system of claim 14, wherein the plurality of processed signals that are created provide realistic feel haptic feedback indicative of the different kinds of biological tissues.

16. The operating system of claim 15, wherein the graphical user haptic interface enables manual or automatic control over the processed signals according to operator preference and procedure type.

17. The operating system of claim 1, wherein the series of continuous real time sensor acquired data is obtained during a transeptal puncture procedure.

18. A method for operating a system including a haptic apparatus that generates palpable sensations based on haptic signals that feel as if the sensations are occurring as a result of actual real time palpation of moving biological tissue, an elongate medical device with sensorized distal end, and a graphical user haptic interlace, comprising:
receiving a series of continuous sensor acquired data with the elongate medical device, the data having a temporal relationship with associated physiological and physical events related to moving biological organ, muscle, cardiac valve, vasculature tissue, or flowing blood;
processing the sensor acquired data to create a plurality of processed signals;
outputting the plurality of processed signals to:
hardware that communicates recreated realistic tangible palpable sensations representative of three dimensional motion to an operator via one or more haptic apparatus; and
a graphical user haptic interface; and
implementing customized programming changes received from the graphical user haptic interlace that do not alter the temporal relationship of sensor acquired data and associated physiological and physical events.

19. A method for operating a system including a haptic apparatus with a user customizable graphical user interface coupled to an elongate member, comprising:
obtaining a series of continuous sensor data from distally located sensors on the elongate member, the data having a temporal relationship with associated physiological and physical events related to moving biological organ, muscle, cardiac valve, vasculature tissue, or lowing blood;

utilizing the sensor data to provide a haptic recreation of sensed information with a haptic apparatus;

using a graphical user interface to customize palpable sensations representative of three dimensional motion generated by the haptic apparatus that replicate sensed physiological and physical events as if haptic signals were occurring as a result of actual realtime palpation of moving biological tissue by permitting adjustment to one or more of the: amplitude of the tangible sensations; quality of the tangible sensations; and subjective haptic preferences of a user; without altering the temporal relationship of the sensor data with associated physiological and physical events.

20. A user interface, comprising:

a haptic apparatus, that is configured to couple with an elongate member having distally located sensors which acquire a series of continuous data from moving biological organ, muscle, cardiac valve, vasculature tissue, or flowing blood, the data having a temporal relationship with associated physiological and physical events related to moving biological organ, muscle, cardiac valve, vasculature tissue, or flowing blood, the haptic apparatus including at least one component providing real time tangible sensations representative of three dimensional motion that supply haptic recreations of physical, physiological, and anatomical data that replicate sensed physiological and physical events as if haptic signals were occurring as a result of actual real time palpation of moving biological tissue; and a graphical user haptic interface that permits user customization of the real time tangible sensations of the haptic apparatus without altering the temporal relationship of the sensor data with associated physiological and physical events.

* * * * *

UNITED STATES PATENT AND TRADEMARK OFFICE
CERTIFICATE OF CORRECTION

PATENT NO. : 10,013,082 B2
APPLICATION NO. : 13/837132
DATED : July 3, 2018
INVENTOR(S) : Stuart O. Schecter Page 1 of 1

It is certified that error appears in the above-identified patent and that said Letters Patent is hereby corrected as shown below:

In the Claims

Column 30, Line 44, please delete "interlace" and insert in its place --interface--.

Column 30, Line 59, please delete "interlace" and insert in its place --interface--.

Column 31, Line 3, please delete "lowing" and insert in its place --flowing--.

Signed and Sealed this
Second Day of October, 2018

Andrei Iancu
*Director of the United States Patent and Trademark Office*